US012709638B2

(12) United States Patent
Zhang

(10) Patent No.: US 12,709,638 B2
(45) Date of Patent: Aug. 18, 2026

(54) PROTEIN HETERODIMER AND USE THEREOF

(71) Applicant: NINGBO INNOVATIVE MECHANISM BIOSCIENCE LLC, Ningbo City (CN)

(72) Inventor: Jinyu Zhang, Chongqing (CN)

(73) Assignee: NINGBO INNOVATIVE MECHANISM BIOSCIENCE LLC, Ningbo City (CN)

( * ) Notice: Subject to any disclaimer, the term of this patent is extended or adjusted under 35 U.S.C. 154(b) by 1331 days.

(21) Appl. No.: 17/606,846

(22) PCT Filed: Apr. 24, 2020

(86) PCT No.: PCT/CN2020/086755
§ 371 (c)(1),
(2) Date: Oct. 27, 2021

(87) PCT Pub. No.: WO2020/221136
PCT Pub. Date: Nov. 5, 2020

(65) Prior Publication Data

US 2022/0213160 A1 Jul. 7, 2022

(30) Foreign Application Priority Data

Apr. 27, 2019 (CN) ......................... 201910351987.4

(51) Int. Cl.

| | |
|---|---|
| ***C07K 14/54*** | (2006.01) |
| ***A61P 35/00*** | (2006.01) |
| ***C07K 14/535*** | (2006.01) |
| ***C07K 14/55*** | (2006.01) |
| ***C07K 16/18*** | (2006.01) |
| *A61K 38/00* | (2006.01) |
| *C07K 16/36* | (2006.01) |

(52) U.S. Cl.
CPC .......... *C07K 14/5434* (2013.01); *A61P 35/00* (2018.01); *C07K 14/535* (2013.01); *C07K 14/55* (2013.01); *C07K 16/18* (2013.01); *A61K 38/00* (2013.01); *C07K 16/36* (2013.01); *C07K 2317/622* (2013.01); *C07K 2319/01* (2013.01)

(58) Field of Classification Search
None
See application file for complete search history.

(56) References Cited

U.S. PATENT DOCUMENTS

| | | | | |
|---|---|---|---|---|
| 6,617,135 | B1 | 9/2003 | Gillies et al. | |
| 6,838,260 | B2 * | 1/2005 | Gillies | C07K 14/54 435/69.51 |
| 7,141,651 | B2 | 11/2006 | Gillies et al. | |
| 7,582,288 | B2 | 9/2009 | Gillies et al. | |
| 11,795,203 | B2 * | 10/2023 | Zhang | A61P 35/00 |
| 2004/0072299 | A1 * | 4/2004 | Gillies | C07K 14/535 530/391.1 |
| 2009/0035255 | A1 | 2/2009 | Neri et al. | |
| 2019/0194283 | A1 | 6/2019 | Hauskins et al. | |
| 2020/0199189 | A1 | 6/2020 | Zhang | |

FOREIGN PATENT DOCUMENTS

| | | | | |
|---|---|---|---|---|
| CN | 1382158 | A | 11/2002 | |
| WO | WO 2006/119897 | A2 | 11/2006 | |
| WO | WO 2018/023093 | A1 | 2/2018 | |
| WO | WO 2018/184484 | A1 | 10/2018 | |
| WO | WO-2020221135 | A1 * | 11/2020 | A61K 38/16 |

OTHER PUBLICATIONS

Spangler et al (Annu Rev Immunol. Mar. 21, 2015; 33: 139-167) (Year: 2015).*
Miosge et al (Proc Natl Acad Sci U S A. Sep. 15, 2015;112(37):E5189-98) (Year: 2015).*
Lee et al (Nat Rev Mol Cell Biol. Dec. 2007;8(12):995-1005) (Year: 2007).*
Bowie et al. (Science, 1990, 247:1306-1310) (Year: 1990).*
Lazar et al. (Mol. Cell. Biol., 8:1247-1252, 1988) (Year: 1988).*
Bork (Genome Research, 2000, 10:398-400) (Year: 2000).*
Brombacher et al. (Trends Immunol. 24:207-212 (2003)) (Year: 2003).*
Wen et al. (J Transl Med 14:41, pp. 1-13 (2016)) (Year: 2016).*
International Search Report issued on Jul. 30, 2020 in PCT/CN2020/086755 filed on Apr. 24, 2020, 3 pages.
Wen, Q. et al., "Fusion cytokine IL-2-GMCSF enhances anticancer immune responses through promoting cell-cell interactions," Journal of Translational Medicine, vol. 14, No. 41, 2016, pp. 1-13.

* cited by examiner

*Primary Examiner* — Brian Gangle
*Assistant Examiner* — Andrea K Mccollum
(74) *Attorney, Agent, or Firm* — Merchant & Gould P.C.; Daniel J. Pereira

(57) ABSTRACT

The present application provides a protein heterodimer and use thereof. The protein heterodimer comprises a first polypeptide chain and a second polypeptide chain different from the first polypeptide chain, wherein the first polypeptide chain comprises IL12a, and the second polypeptide chain comprises interleukin-12b (IL12b). The protein heterodimer also comprises interleukin-2 (IL2) or its functional fragments, granulocyte macrophage colony stimulating factor (GMCSF) or its functional fragments, and one or more targeting moieties. The protein heterodimer can be used for the treatment of tumors.

3 Claims, 4 Drawing Sheets

Specification includes a Sequence Listing.

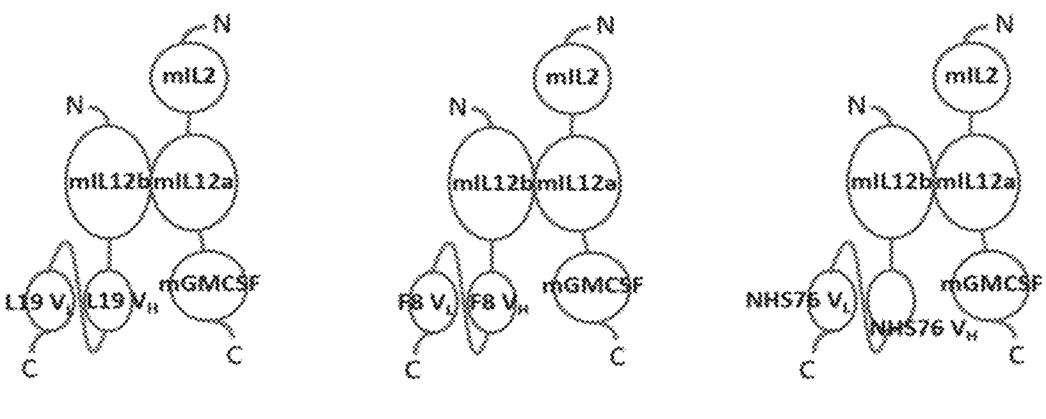
FIG. 3
FIG. 4
FIG. 5
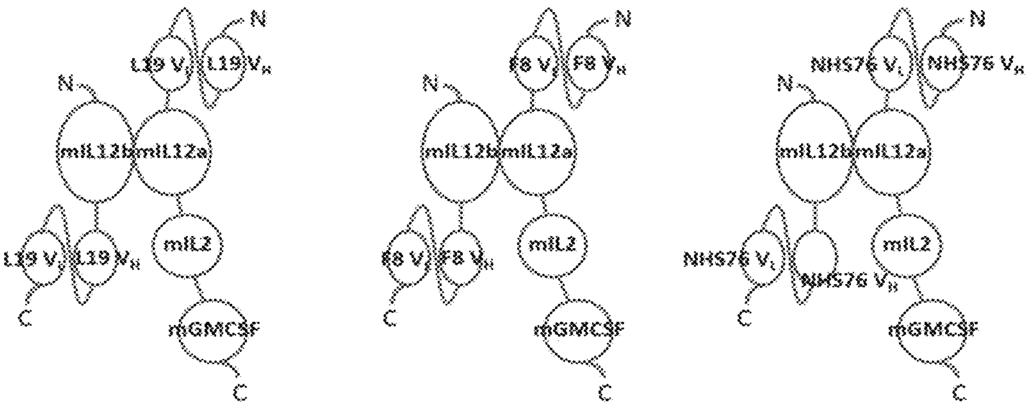
FIG. 6
FIG. 7
FIG. 8
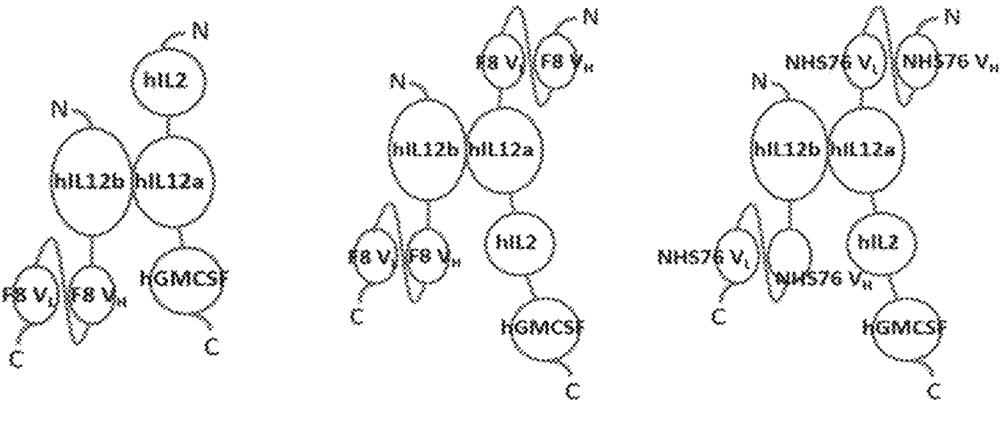
FIG. 9
FIG. 10
FIG. 11

SEQUENCE LISTING

```
<160> NUMBER OF SEQ ID NOS: 41

<210> SEQ ID NO 1
<211> LENGTH: 236
<212> TYPE: PRT
<213> ORGANISM: Artificial Sequence
```

```
<220> FEATURE:
<223> OTHER INFORMATION: targeting moiety scL19

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys
225                 230                 235


<210> SEQ ID NO 2
<211> LENGTH: 240
<212> TYPE: PRT
<213> ORGANISM: Artificial Sequence
<220> FEATURE:
<223> OTHER INFORMATION: targeting moiety scF8

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
```

```
            100                 105                 110

Leu Val Thr Val Ser Ser Ser Ser Gly Asp Gly Ser Ser Gly Gly Ser
        115                 120                 125

Gly Gly Ala Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Ser Met Pro Phe Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
        195                 200                 205

Ser Arg Leu Glu Pro Glu Asp Phe Ala Val Tyr Tyr Cys Gln Gln Met
    210                 215                 220

Arg Gly Arg Pro Pro Thr Phe Gly Gln Gly Thr Lys Val Glu Ile Lys
225                 230                 235                 240


<210> SEQ ID NO 3
<211> LENGTH: 239
<212> TYPE: PRT
<213> ORGANISM: Artificial Sequence
<220> FEATURE:
<223> OTHER INFORMATION: targeting moiety scNHS76

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Lys Trp Ser Lys Phe Asp Tyr Trp Gly Gln Gly Thr Leu
            100                 105                 110

Val Thr Val Ser Ser Ser Ser Gly Asp Gly Ser Ser Gly Gly Ser Gly
        115                 120                 125

Gly Ala Ser Ser Ser Glu Leu Thr Gln Asp Pro Ala Val Ser Val Ala
    130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Val Leu
                165                 170                 175

Val Ile Tyr Gly Lys Asn Asn Arg Pro Ser Gly Ile Pro Asp Arg Phe
            180                 185                 190

Ser Gly Ser Ser Ser Gly Asn Thr Ala Ser Leu Thr Ile Thr Gly Ala
        195                 200                 205

Gln Ala Glu Asp Glu Ala Asp Tyr Tyr Cys Asn Ser Arg Asp Ser Ser
    210                 215                 220

Gly Asn His Val Val Phe Gly Gly Gly Thr Lys Leu Thr Val Leu
```

```
225                 230                 235


<210> SEQ ID NO 4
<211> LENGTH: 193
<212> TYPE: PRT
<213> ORGANISM: Homo sapiens

<400> SEQUENCE: 4

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
    130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala


<210> SEQ ID NO 5
<211> LENGTH: 313
<212> TYPE: PRT
<213> ORGANISM: Homo sapiens

<400> SEQUENCE: 5

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125
```

```
Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser
305                 310


<210> SEQ ID NO 6
<211> LENGTH: 197
<212> TYPE: PRT
<213> ORGANISM: Homo sapiens

<400> SEQUENCE: 6

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
```

```
            180                 185                 190

Tyr Leu Asn Ala Ser
        195


<210> SEQ ID NO 7
<211> LENGTH: 306
<212> TYPE: PRT
<213> ORGANISM: Homo sapiens

<400> SEQUENCE: 7

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 8
<211> LENGTH: 149
<212> TYPE: PRT
<213> ORGANISM: Homo sapiens
```

<400> SEQUENCE: 8

```
Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 9
<211> LENGTH: 133
<212> TYPE: PRT
<213> ORGANISM: Homo sapiens

<400> SEQUENCE: 9

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 10
<211> LENGTH: 124
<212> TYPE: PRT
<213> ORGANISM: Homo sapiens

<400> SEQUENCE: 10

```
Ala Pro Thr Arg Ser Pro Ile Thr Val Thr Arg Pro Trp Lys His Val
1               5                   10                  15

Glu Ala Ile Lys Glu Ala Leu Asn Leu Leu Asp Asp Met Pro Val Thr
```

```
            20                  25                  30

Leu Asn Glu Glu Val Glu Val Val Ser Asn Glu Phe Ser Phe Lys Lys
        35                  40                  45

Leu Thr Cys Val Gln Thr Arg Leu Lys Ile Phe Glu Gln Gly Leu Arg
    50                  55                  60

Gly Asn Phe Thr Lys Leu Lys Gly Ala Leu Asn Met Thr Ala Ser Tyr
65                  70                  75                  80

Tyr Gln Thr Tyr Cys Pro Pro Thr Pro Glu Thr Asp Cys Glu Thr Gln
                85                  90                  95

Val Thr Thr Tyr Ala Asp Phe Ile Asp Ser Leu Lys Thr Phe Leu Thr
            100                 105                 110

Asp Ile Pro Phe Glu Cys Lys Lys Pro Gly Gln Lys
        115                 120


<210> SEQ ID NO 11
<211> LENGTH: 127
<212> TYPE: PRT
<213> ORGANISM: Homo sapiens

<400> SEQUENCE: 11

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125


<210> SEQ ID NO 12
<211> LENGTH: 555
<212> TYPE: PRT
<213> ORGANISM: Artificial Sequence
<220> FEATURE:
<223> OTHER INFORMATION: second polypeptide chain (mouse mIL12bscL19
      chain)

<400> SEQUENCE: 12

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
```

-continued

```
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Ser Ala Asp Gly Gly Glu
305                 310                 315                 320

Val Gln Leu Leu Glu Ser Gly Gly Gly Leu Val Gln Pro Gly Gly Ser
                325                 330                 335

Leu Arg Leu Ser Cys Ala Ala Ser Gly Phe Thr Phe Ser Ser Phe Ser
            340                 345                 350

Met Ser Trp Val Arg Gln Ala Pro Gly Lys Gly Leu Glu Trp Val Ser
        355                 360                 365

Ser Ile Ser Gly Ser Ser Gly Thr Thr Tyr Tyr Ala Asp Ser Val Lys
    370                 375                 380

Gly Arg Phe Thr Ile Ser Arg Asp Asn Ser Lys Asn Thr Leu Tyr Leu
385                 390                 395                 400

Gln Met Asn Ser Leu Arg Ala Glu Asp Thr Ala Val Tyr Tyr Cys Ala
                405                 410                 415

Lys Pro Phe Pro Tyr Phe Asp Tyr Trp Gly Gln Gly Thr Leu Val Thr
            420                 425                 430

Val Ser Ser Gly Asp Gly Ser Ser Gly Gly Ser Gly Gly Ala Ser Glu
        435                 440                 445

Ile Val Leu Thr Gln Ser Pro Gly Thr Leu Ser Leu Ser Pro Gly Glu
    450                 455                 460

Arg Ala Thr Leu Ser Cys Arg Ala Ser Gln Ser Val Ser Ser Ser Phe
465                 470                 475                 480

Leu Ala Trp Tyr Gln Gln Lys Pro Gly Gln Ala Pro Arg Leu Leu Ile
                485                 490                 495

Tyr Tyr Ala Ser Ser Arg Ala Thr Gly Ile Pro Asp Arg Phe Ser Gly
            500                 505                 510
```

```
Ser Gly Ser Gly Thr Asp Phe Thr Leu Thr Ile Ser Arg Leu Glu Pro
        515                 520                 525

Glu Asp Phe Ala Val Tyr Tyr Cys Gln Gln Thr Gly Arg Ile Pro Pro
    530                 535                 540

Thr Phe Gly Gln Gly Thr Lys Val Glu Ile Lys
545                 550                 555


<210> SEQ ID NO 13
<211> LENGTH: 559
<212> TYPE: PRT
<213> ORGANISM: Artificial Sequence
<220> FEATURE:
<223> OTHER INFORMATION: second polypeptide chain (mouse mIL12bscF8
      chain)

<400> SEQUENCE: 13

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Ser Ala Asp Gly Gly Glu
```

```
305                 310                 315                 320

Val Gln Leu Leu Glu Ser Gly Gly Gly Leu Val Gln Pro Gly Gly Ser
                325                 330                 335

Leu Arg Leu Ser Cys Ala Ala Ser Gly Phe Thr Phe Ser Leu Phe Thr
            340                 345                 350

Met Ser Trp Val Arg Gln Ala Pro Gly Lys Gly Leu Glu Trp Val Ser
        355                 360                 365

Ala Ile Ser Gly Ser Gly Gly Ser Thr Tyr Tyr Ala Asp Ser Val Lys
    370                 375                 380

Gly Arg Phe Thr Ile Ser Arg Asp Asn Ser Lys Asn Thr Leu Tyr Leu
385                 390                 395                 400

Gln Met Asn Ser Leu Arg Ala Glu Asp Thr Ala Val Tyr Tyr Cys Ala
                405                 410                 415

Lys Ser Thr His Leu Tyr Leu Phe Asp Tyr Trp Gly Gln Gly Thr Leu
            420                 425                 430

Val Thr Val Ser Ser Ser Ser Gly Asp Gly Ser Ser Gly Gly Ser Gly
        435                 440                 445

Gly Ala Ser Glu Ile Val Leu Thr Gln Ser Pro Gly Thr Leu Ser Leu
    450                 455                 460

Ser Pro Gly Glu Arg Ala Thr Leu Ser Cys Arg Ala Ser Gln Ser Val
465                 470                 475                 480

Ser Met Pro Phe Leu Ala Trp Tyr Gln Gln Lys Pro Gly Gln Ala Pro
                485                 490                 495

Arg Leu Leu Ile Tyr Gly Ala Ser Ser Arg Ala Thr Gly Ile Pro Asp
            500                 505                 510

Arg Phe Ser Gly Ser Gly Ser Gly Thr Asp Phe Thr Leu Thr Ile Ser
        515                 520                 525

Arg Leu Glu Pro Glu Asp Phe Ala Val Tyr Tyr Cys Gln Gln Met Arg
    530                 535                 540

Gly Arg Pro Pro Thr Phe Gly Gln Gly Thr Lys Val Glu Ile Lys
545                 550                 555


<210> SEQ ID NO 14
<211> LENGTH: 558
<212> TYPE: PRT
<213> ORGANISM: Artificial Sequence
<220> FEATURE:
<223> OTHER INFORMATION: second polypeptide chain (mouse mIL12bscNHS76
      chain)

<400> SEQUENCE: 14

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110
```

-continued

```
Gly Arg Phe Thr Cys Ser Trp Leu Val Gln Arg Asn Met Asp Leu Lys
        115                 120                 125

Phe Asn Ile Lys Ser Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300

Ala Cys Val Pro Cys Arg Val Arg Ser Gly Ser Ala Asp Gly Gly Gln
305                 310                 315                 320

Val Gln Leu Gln Glu Ser Gly Pro Gly Leu Val Lys Pro Ser Glu Thr
                325                 330                 335

Leu Ser Leu Thr Cys Ala Val Ser Gly Tyr Ser Ile Ser Ser Gly Tyr
            340                 345                 350

Tyr Trp Gly Trp Ile Arg Gln Pro Pro Gly Lys Gly Leu Glu Trp Ile
        355                 360                 365

Gly Ser Ile Tyr His Ser Gly Ser Thr Tyr Tyr Asn Pro Ser Leu Lys
    370                 375                 380

Ser Arg Val Thr Ile Ser Val Asp Thr Ser Lys Asn Gln Phe Ser Leu
385                 390                 395                 400

Lys Leu Ser Ser Val Thr Ala Ala Asp Thr Ala Val Tyr Tyr Cys Ala
                405                 410                 415

Arg Gly Lys Trp Ser Lys Phe Asp Tyr Trp Gly Gln Gly Thr Leu Val
            420                 425                 430

Thr Val Ser Ser Ser Ser Gly Asp Gly Ser Ser Gly Gly Ser Gly Gly
        435                 440                 445

Ala Ser Ser Ser Glu Leu Thr Gln Asp Pro Ala Val Ser Val Ala Leu
    450                 455                 460

Gly Gln Thr Val Arg Ile Thr Cys Gln Gly Asp Ser Leu Arg Ser Tyr
465                 470                 475                 480

Tyr Ala Ser Trp Tyr Gln Gln Lys Pro Gly Gln Ala Pro Val Leu Val
                485                 490                 495

Ile Tyr Gly Lys Asn Asn Arg Pro Ser Gly Ile Pro Asp Arg Phe Ser
            500                 505                 510

Gly Ser Ser Ser Gly Asn Thr Ala Ser Leu Thr Ile Thr Gly Ala Gln
        515                 520                 525

Ala Glu Asp Glu Ala Asp Tyr Tyr Cys Asn Ser Arg Asp Ser Ser Gly
```

```
    530                 535                 540

Asn His Val Val Phe Gly Gly Gly Thr Lys Leu Thr Val Leu
545                 550                 555


<210> SEQ ID NO 15
<211> LENGTH: 552
<212> TYPE: PRT
<213> ORGANISM: Artificial Sequence
<220> FEATURE:
<223> OTHER INFORMATION: second polypeptide chain (human hIL12bscF8
      chain)

<400> SEQUENCE: 15

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Ala Asp Gly Gly Glu Val Gln Leu Leu Glu Ser Gly
305                 310                 315                 320

Gly Gly Leu Val Gln Pro Gly Gly Ser Leu Arg Leu Ser Cys Ala Ala
                325                 330                 335
```

```
Ser Gly Phe Thr Phe Ser Leu Phe Thr Met Ser Trp Val Arg Gln Ala
            340                 345                 350

Pro Gly Lys Gly Leu Glu Trp Val Ser Ala Ile Ser Gly Ser Gly Gly
        355                 360                 365

Ser Thr Tyr Tyr Ala Asp Ser Val Lys Gly Arg Phe Thr Ile Ser Arg
    370                 375                 380

Asp Asn Ser Lys Asn Thr Leu Tyr Leu Gln Met Asn Ser Leu Arg Ala
385                 390                 395                 400

Glu Asp Thr Ala Val Tyr Tyr Cys Ala Lys Ser Thr His Leu Tyr Leu
                405                 410                 415

Phe Asp Tyr Trp Gly Gln Gly Thr Leu Val Thr Val Ser Ser Ser Ser
            420                 425                 430

Gly Asp Gly Ser Ser Gly Gly Ser Gly Gly Ala Ser Glu Ile Val Leu
        435                 440                 445

Thr Gln Ser Pro Gly Thr Leu Ser Leu Ser Pro Gly Glu Arg Ala Thr
    450                 455                 460

Leu Ser Cys Arg Ala Ser Gln Ser Val Ser Met Pro Phe Leu Ala Trp
465                 470                 475                 480

Tyr Gln Gln Lys Pro Gly Gln Ala Pro Arg Leu Leu Ile Tyr Gly Ala
                485                 490                 495

Ser Ser Arg Ala Thr Gly Ile Pro Asp Arg Phe Ser Gly Ser Gly Ser
            500                 505                 510

Gly Thr Asp Phe Thr Leu Thr Ile Ser Arg Leu Glu Pro Glu Asp Phe
        515                 520                 525

Ala Val Tyr Tyr Cys Gln Gln Met Arg Gly Arg Pro Pro Thr Phe Gly
    530                 535                 540

Gln Gly Thr Lys Val Glu Ile Lys
545                 550


<210> SEQ ID NO 16
<211> LENGTH: 551
<212> TYPE: PRT
<213> ORGANISM: Artificial Sequence
<220> FEATURE:
<223> OTHER INFORMATION: second polypeptide chain (human hIL12bscNHS76
      chain)

<400> SEQUENCE: 16

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140
```

```
Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Ser Ala Asp Gly Gly Gln Val Gln Leu Gln Glu Ser Gly
305                 310                 315                 320

Pro Gly Leu Val Lys Pro Ser Glu Thr Leu Ser Leu Thr Cys Ala Val
                325                 330                 335

Ser Gly Tyr Ser Ile Ser Ser Gly Tyr Tyr Trp Gly Trp Ile Arg Gln
            340                 345                 350

Pro Pro Gly Lys Gly Leu Glu Trp Ile Gly Ser Ile Tyr His Ser Gly
        355                 360                 365

Ser Thr Tyr Tyr Asn Pro Ser Leu Lys Ser Arg Val Thr Ile Ser Val
    370                 375                 380

Asp Thr Ser Lys Asn Gln Phe Ser Leu Lys Leu Ser Ser Val Thr Ala
385                 390                 395                 400

Ala Asp Thr Ala Val Tyr Tyr Cys Ala Arg Gly Lys Trp Ser Lys Phe
                405                 410                 415

Asp Tyr Trp Gly Gln Gly Thr Leu Val Thr Val Ser Ser Ser Ser Gly
            420                 425                 430

Asp Gly Ser Ser Gly Gly Ser Gly Gly Ala Ser Ser Ser Glu Leu Thr
        435                 440                 445

Gln Asp Pro Ala Val Ser Val Ala Leu Gly Gln Thr Val Arg Ile Thr
    450                 455                 460

Cys Gln Gly Asp Ser Leu Arg Ser Tyr Tyr Ala Ser Trp Tyr Gln Gln
465                 470                 475                 480

Lys Pro Gly Gln Ala Pro Val Leu Val Ile Tyr Gly Lys Asn Asn Arg
                485                 490                 495

Pro Ser Gly Ile Pro Asp Arg Phe Ser Gly Ser Ser Ser Gly Asn Thr
            500                 505                 510

Ala Ser Leu Thr Ile Thr Gly Ala Gln Ala Glu Asp Glu Ala Asp Tyr
        515                 520                 525

Tyr Cys Asn Ser Arg Asp Ser Ser Gly Asn His Val Val Phe Gly Gly
    530                 535                 540

Gly Thr Lys Leu Thr Val Leu
545                 550
```

```
<210> SEQ ID NO 17
<211> LENGTH: 496
<212> TYPE: PRT
<213> ORGANISM: Artificial Sequence
<220> FEATURE:
<223> OTHER INFORMATION: first polypeptide chain (mouse mIL2IL12aGMCSF
      chain)

<400> SEQUENCE: 17

Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln Gly Gly Gly Gly Ser Gly Gly Gly Gly Ser Gly
145                 150                 155                 160

Gly Gly Gly Ser Arg Val Ile Pro Val Ser Gly Pro Ala Arg Cys Leu
                165                 170                 175

Ser Gln Ser Arg Asn Leu Leu Lys Thr Thr Asp Asp Met Val Lys Thr
            180                 185                 190

Ala Arg Glu Lys Leu Lys His Tyr Ser Cys Thr Ala Glu Asp Ile Asp
        195                 200                 205

His Glu Asp Ile Thr Arg Asp Gln Thr Ser Thr Leu Lys Thr Cys Leu
    210                 215                 220

Pro Leu Glu Leu His Lys Asn Glu Ser Cys Leu Ala Thr Arg Glu Thr
225                 230                 235                 240

Ser Ser Thr Thr Arg Gly Ser Cys Leu Pro Pro Gln Lys Thr Ser Leu
                245                 250                 255

Met Met Thr Leu Cys Leu Gly Ser Ile Tyr Glu Asp Leu Lys Met Tyr
            260                 265                 270

Gln Thr Glu Phe Gln Ala Ile Asn Ala Ala Leu Gln Asn His Asn His
        275                 280                 285

Gln Gln Ile Ile Leu Asp Lys Gly Met Leu Val Ala Ile Asp Glu Leu
    290                 295                 300

Met Gln Ser Leu Asn His Asn Gly Glu Thr Leu Arg Gln Lys Pro Pro
305                 310                 315                 320

Val Gly Glu Ala Asp Pro Tyr Arg Val Lys Met Lys Leu Cys Ile Leu
                325                 330                 335

Leu His Ala Phe Ser Thr Arg Val Val Thr Ile Asn Arg Val Met Gly
            340                 345                 350

Tyr Leu Ser Ser Ala Gly Gly Gly Gly Ser Gly Gly Gly Gly Ser Gly
        355                 360                 365
```

```
Gly Gly Gly Ser Ala Pro Thr Arg Ser Pro Ile Thr Val Thr Arg Pro
    370                 375                 380

Trp Lys His Val Glu Ala Ile Lys Glu Ala Leu Asn Leu Leu Asp Asp
385                 390                 395                 400

Met Pro Val Thr Leu Asn Glu Glu Val Glu Val Val Ser Asn Glu Phe
                405                 410                 415

Ser Phe Lys Lys Leu Thr Cys Val Gln Thr Arg Leu Lys Ile Phe Glu
            420                 425                 430

Gln Gly Leu Arg Gly Asn Phe Thr Lys Leu Lys Gly Ala Leu Asn Met
        435                 440                 445

Thr Ala Ser Tyr Tyr Gln Thr Tyr Cys Pro Pro Thr Pro Glu Thr Asp
    450                 455                 460

Cys Glu Thr Gln Val Thr Thr Tyr Ala Asp Phe Ile Asp Ser Leu Lys
465                 470                 475                 480

Thr Phe Leu Thr Asp Ile Pro Phe Glu Cys Lys Lys Pro Gly Gln Lys
                485                 490                 495
```

<210> SEQ ID NO 18
<211> LENGTH: 738
<212> TYPE: PRT
<213> ORGANISM: Artificial Sequence
<220> FEATURE:
<223> OTHER INFORMATION: first polypeptide chain (mouse mscL19IL12aIL2GMCSF chain)

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
        115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys Gly Ser Ala Asp
```

-continued

```
225                 230                 235                 240

Gly Gly Arg Val Ile Pro Val Ser Gly Pro Ala Arg Cys Leu Ser Gln
                245                 250                 255

Ser Arg Asn Leu Leu Lys Thr Thr Asp Asp Met Val Lys Thr Ala Arg
            260                 265                 270

Glu Lys Leu Lys His Tyr Ser Cys Thr Ala Glu Asp Ile Asp His Glu
        275                 280                 285

Asp Ile Thr Arg Asp Gln Thr Ser Thr Leu Lys Thr Cys Leu Pro Leu
    290                 295                 300

Glu Leu His Lys Asn Glu Ser Cys Leu Ala Thr Arg Glu Thr Ser Ser
305                 310                 315                 320

Thr Thr Arg Gly Ser Cys Leu Pro Pro Gln Lys Thr Ser Leu Met Met
                325                 330                 335

Thr Leu Cys Leu Gly Ser Ile Tyr Glu Asp Leu Lys Met Tyr Gln Thr
            340                 345                 350

Glu Phe Gln Ala Ile Asn Ala Ala Leu Gln Asn His Asn His Gln Gln
        355                 360                 365

Ile Ile Leu Asp Lys Gly Met Leu Val Ala Ile Asp Glu Leu Met Gln
    370                 375                 380

Ser Leu Asn His Asn Gly Glu Thr Leu Arg Gln Lys Pro Pro Val Gly
385                 390                 395                 400

Glu Ala Asp Pro Tyr Arg Val Lys Met Lys Leu Cys Ile Leu Leu His
                405                 410                 415

Ala Phe Ser Thr Arg Val Val Thr Ile Asn Arg Val Met Gly Tyr Leu
            420                 425                 430

Ser Ser Ala Gly Gly Gly Gly Ser Gly Gly Gly Gly Ser Gly Gly Gly
        435                 440                 445

Gly Ser Ala Pro Thr Ser Ser Ser Thr Ser Ser Ser Thr Ala Glu Ala
    450                 455                 460

Gln Gln Gln Gln Gln Gln Gln Gln Gln Gln Gln Gln His Leu Glu Gln
465                 470                 475                 480

Leu Leu Met Asp Leu Gln Glu Leu Leu Ser Arg Met Glu Asn Tyr Arg
                485                 490                 495

Asn Leu Lys Leu Pro Arg Met Leu Thr Phe Lys Phe Tyr Leu Pro Lys
            500                 505                 510

Gln Ala Thr Glu Leu Lys Asp Leu Gln Cys Leu Glu Asp Glu Leu Gly
        515                 520                 525

Pro Leu Arg His Val Leu Asp Leu Thr Gln Ser Lys Ser Phe Gln Leu
    530                 535                 540

Glu Asp Ala Glu Asn Phe Ile Ser Asn Ile Arg Val Thr Val Val Lys
545                 550                 555                 560

Leu Lys Gly Ser Asp Asn Thr Phe Glu Cys Gln Phe Asp Asp Glu Ser
                565                 570                 575

Ala Thr Val Val Asp Phe Leu Arg Arg Trp Ile Ala Phe Cys Gln Ser
            580                 585                 590

Ile Ile Ser Thr Ser Pro Gln Gly Gly Gly Gly Ser Gly Gly Gly Gly
        595                 600                 605

Ser Gly Gly Gly Gly Ser Ala Pro Thr Arg Ser Pro Ile Thr Val Thr
    610                 615                 620

Arg Pro Trp Lys His Val Glu Ala Ile Lys Glu Ala Leu Asn Leu Leu
625                 630                 635                 640

Asp Asp Met Pro Val Thr Leu Asn Glu Glu Val Glu Val Val Ser Asn
                645                 650                 655
```

```
Glu Phe Ser Phe Lys Lys Leu Thr Cys Val Gln Thr Arg Leu Lys Ile
            660                 665                 670

Phe Glu Gln Gly Leu Arg Gly Asn Phe Thr Lys Leu Lys Gly Ala Leu
        675                 680                 685

Asn Met Thr Ala Ser Tyr Tyr Gln Thr Tyr Cys Pro Pro Thr Pro Glu
    690                 695                 700

Thr Asp Cys Glu Thr Gln Val Thr Thr Tyr Ala Asp Phe Ile Asp Ser
705                 710                 715                 720

Leu Lys Thr Phe Leu Thr Asp Ile Pro Phe Glu Cys Lys Lys Pro Gly
                725                 730                 735

Gln Lys


<210> SEQ ID NO 19
<211> LENGTH: 742
<212> TYPE: PRT
<213> ORGANISM: Artificial Sequence
<220> FEATURE:
<223> OTHER INFORMATION: first polypeptide chain (mouse
      mscF8IL12aIL2GMCSF chain)

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Ser Ser Gly Asp Gly Ser Ser Gly Gly Ser
        115                 120                 125

Gly Gly Ala Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Ser Met Pro Phe Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
        195                 200                 205

Ser Arg Leu Glu Pro Glu Asp Phe Ala Val Tyr Tyr Cys Gln Gln Met
    210                 215                 220

Arg Gly Arg Pro Pro Thr Phe Gly Gln Gly Thr Lys Val Glu Ile Lys
225                 230                 235                 240

Gly Ser Ala Asp Gly Gly Arg Val Ile Pro Val Ser Gly Pro Ala Arg
                245                 250                 255

Cys Leu Ser Gln Ser Arg Asn Leu Leu Lys Thr Thr Asp Asp Met Val
            260                 265                 270
```

```
Lys Thr Ala Arg Glu Lys Leu Lys His Tyr Ser Cys Thr Ala Glu Asp
        275                 280                 285

Ile Asp His Glu Asp Ile Thr Arg Asp Gln Thr Ser Thr Leu Lys Thr
    290                 295                 300

Cys Leu Pro Leu Glu Leu His Lys Asn Glu Ser Cys Leu Ala Thr Arg
305                 310                 315                 320

Glu Thr Ser Ser Thr Thr Arg Gly Ser Cys Leu Pro Pro Gln Lys Thr
                325                 330                 335

Ser Leu Met Met Thr Leu Cys Leu Gly Ser Ile Tyr Glu Asp Leu Lys
            340                 345                 350

Met Tyr Gln Thr Glu Phe Gln Ala Ile Asn Ala Ala Leu Gln Asn His
        355                 360                 365

Asn His Gln Gln Ile Ile Leu Asp Lys Gly Met Leu Val Ala Ile Asp
    370                 375                 380

Glu Leu Met Gln Ser Leu Asn His Asn Gly Glu Thr Leu Arg Gln Lys
385                 390                 395                 400

Pro Pro Val Gly Glu Ala Asp Pro Tyr Arg Val Lys Met Lys Leu Cys
                405                 410                 415

Ile Leu Leu His Ala Phe Ser Thr Arg Val Val Thr Ile Asn Arg Val
            420                 425                 430

Met Gly Tyr Leu Ser Ser Ala Gly Gly Gly Gly Ser Gly Gly Gly Gly
        435                 440                 445

Ser Gly Gly Gly Gly Ser Ala Pro Thr Ser Ser Ser Thr Ser Ser Ser
    450                 455                 460

Thr Ala Glu Ala Gln Gln Gln Gln Gln Gln Gln Gln Gln Gln Gln Gln
465                 470                 475                 480

His Leu Glu Gln Leu Leu Met Asp Leu Gln Glu Leu Leu Ser Arg Met
                485                 490                 495

Glu Asn Tyr Arg Asn Leu Lys Leu Pro Arg Met Leu Thr Phe Lys Phe
            500                 505                 510

Tyr Leu Pro Lys Gln Ala Thr Glu Leu Lys Asp Leu Gln Cys Leu Glu
        515                 520                 525

Asp Glu Leu Gly Pro Leu Arg His Val Leu Asp Leu Thr Gln Ser Lys
    530                 535                 540

Ser Phe Gln Leu Glu Asp Ala Glu Asn Phe Ile Ser Asn Ile Arg Val
545                 550                 555                 560

Thr Val Val Lys Leu Lys Gly Ser Asp Asn Thr Phe Glu Cys Gln Phe
                565                 570                 575

Asp Asp Glu Ser Ala Thr Val Val Asp Phe Leu Arg Arg Trp Ile Ala
            580                 585                 590

Phe Cys Gln Ser Ile Ile Ser Thr Ser Pro Gln Gly Gly Gly Gly Ser
        595                 600                 605

Gly Gly Gly Gly Ser Gly Gly Gly Gly Ser Ala Pro Thr Arg Ser Pro
    610                 615                 620

Ile Thr Val Thr Arg Pro Trp Lys His Val Glu Ala Ile Lys Glu Ala
625                 630                 635                 640

Leu Asn Leu Leu Asp Asp Met Pro Val Thr Leu Asn Glu Glu Val Glu
                645                 650                 655

Val Val Ser Asn Glu Phe Ser Phe Lys Lys Leu Thr Cys Val Gln Thr
            660                 665                 670

Arg Leu Lys Ile Phe Glu Gln Gly Leu Arg Gly Asn Phe Thr Lys Leu
        675                 680                 685
```

```
Lys Gly Ala Leu Asn Met Thr Ala Ser Tyr Tyr Gln Thr Tyr Cys Pro
    690                 695                 700

Pro Thr Pro Glu Thr Asp Cys Glu Thr Gln Val Thr Thr Tyr Ala Asp
705                 710                 715                 720

Phe Ile Asp Ser Leu Lys Thr Phe Leu Thr Asp Ile Pro Phe Glu Cys
                725                 730                 735

Lys Lys Pro Gly Gln Lys
            740


<210> SEQ ID NO 20
<211> LENGTH: 741
<212> TYPE: PRT
<213> ORGANISM: Artificial Sequence
<220> FEATURE:
<223> OTHER INFORMATION: first polypeptide chain (mouse
      mscNHS76IL12aIL2GMCSF chain)

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Lys Trp Ser Lys Phe Asp Tyr Trp Gly Gln Gly Thr Leu
            100                 105                 110

Val Thr Val Ser Ser Ser Ser Gly Asp Gly Ser Ser Gly Gly Ser Gly
        115                 120                 125

Gly Ala Ser Ser Ser Glu Leu Thr Gln Asp Pro Ala Val Ser Val Ala
    130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Val Leu
                165                 170                 175

Val Ile Tyr Gly Lys Asn Asn Arg Pro Ser Gly Ile Pro Asp Arg Phe
            180                 185                 190

Ser Gly Ser Ser Ser Gly Asn Thr Ala Ser Leu Thr Ile Thr Gly Ala
        195                 200                 205

Gln Ala Glu Asp Glu Ala Asp Tyr Tyr Cys Asn Ser Arg Asp Ser Ser
    210                 215                 220

Gly Asn His Val Val Phe Gly Gly Gly Thr Lys Leu Thr Val Leu Gly
225                 230                 235                 240

Ser Ala Asp Gly Gly Arg Val Ile Pro Val Ser Gly Pro Ala Arg Cys
                245                 250                 255

Leu Ser Gln Ser Arg Asn Leu Leu Lys Thr Thr Asp Asp Met Val Lys
            260                 265                 270

Thr Ala Arg Glu Lys Leu Lys His Tyr Ser Cys Thr Ala Glu Asp Ile
        275                 280                 285

Asp His Glu Asp Ile Thr Arg Asp Gln Thr Ser Thr Leu Lys Thr Cys
    290                 295                 300
```

```
Leu Pro Leu Glu Leu His Lys Asn Glu Ser Cys Leu Ala Thr Arg Glu
305                 310                 315                 320

Thr Ser Ser Thr Thr Arg Gly Ser Cys Leu Pro Pro Gln Lys Thr Ser
                325                 330                 335

Leu Met Met Thr Leu Cys Leu Gly Ser Ile Tyr Glu Asp Leu Lys Met
            340                 345                 350

Tyr Gln Thr Glu Phe Gln Ala Ile Asn Ala Ala Leu Gln Asn His Asn
        355                 360                 365

His Gln Gln Ile Ile Leu Asp Lys Gly Met Leu Val Ala Ile Asp Glu
    370                 375                 380

Leu Met Gln Ser Leu Asn His Asn Gly Glu Thr Leu Arg Gln Lys Pro
385                 390                 395                 400

Pro Val Gly Glu Ala Asp Pro Tyr Arg Val Lys Met Lys Leu Cys Ile
                405                 410                 415

Leu Leu His Ala Phe Ser Thr Arg Val Val Thr Ile Asn Arg Val Met
            420                 425                 430

Gly Tyr Leu Ser Ser Ala Gly Gly Gly Gly Ser Gly Gly Gly Gly Ser
        435                 440                 445

Gly Gly Gly Gly Ser Ala Pro Thr Ser Ser Ser Thr Ser Ser Ser Thr
    450                 455                 460

Ala Glu Ala Gln Gln Gln Gln Gln Gln Gln Gln Gln Gln Gln Gln His
465                 470                 475                 480

Leu Glu Gln Leu Leu Met Asp Leu Gln Glu Leu Leu Ser Arg Met Glu
                485                 490                 495

Asn Tyr Arg Asn Leu Lys Leu Pro Arg Met Leu Thr Phe Lys Phe Tyr
            500                 505                 510

Leu Pro Lys Gln Ala Thr Glu Leu Lys Asp Leu Gln Cys Leu Glu Asp
        515                 520                 525

Glu Leu Gly Pro Leu Arg His Val Leu Asp Leu Thr Gln Ser Lys Ser
    530                 535                 540

Phe Gln Leu Glu Asp Ala Glu Asn Phe Ile Ser Asn Ile Arg Val Thr
545                 550                 555                 560

Val Val Lys Leu Lys Gly Ser Asp Asn Thr Phe Glu Cys Gln Phe Asp
                565                 570                 575

Asp Glu Ser Ala Thr Val Val Asp Phe Leu Arg Arg Trp Ile Ala Phe
            580                 585                 590

Cys Gln Ser Ile Ile Ser Thr Ser Pro Gln Gly Gly Gly Gly Ser Gly
        595                 600                 605

Gly Gly Gly Ser Gly Gly Gly Gly Ser Ala Pro Thr Arg Ser Pro Ile
    610                 615                 620

Thr Val Thr Arg Pro Trp Lys His Val Glu Ala Ile Lys Glu Ala Leu
625                 630                 635                 640

Asn Leu Leu Asp Asp Met Pro Val Thr Leu Asn Glu Glu Val Glu Val
                645                 650                 655

Val Ser Asn Glu Phe Ser Phe Lys Lys Leu Thr Cys Val Gln Thr Arg
            660                 665                 670

Leu Lys Ile Phe Glu Gln Gly Leu Arg Gly Asn Phe Thr Lys Leu Lys
        675                 680                 685

Gly Ala Leu Asn Met Thr Ala Ser Tyr Tyr Gln Thr Tyr Cys Pro Pro
    690                 695                 700

Thr Pro Glu Thr Asp Cys Glu Thr Gln Val Thr Thr Tyr Ala Asp Phe
705                 710                 715                 720
```

```
Ile Asp Ser Leu Lys Thr Phe Leu Thr Asp Ile Pro Phe Glu Cys Lys
                725                 730                 735

Lys Pro Gly Gln Lys
            740


<210> SEQ ID NO 21
<211> LENGTH: 487
<212> TYPE: PRT
<213> ORGANISM: Artificial Sequence
<220> FEATURE:
<223> OTHER INFORMATION: first polypeptide chain (human hIL2IL12aGMCSF
      chain)

<400> SEQUENCE: 21

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
    130                 135                 140

Gly Gly Gly Ser Arg Asn Leu Pro Val Ala Thr Pro Asp Pro Gly Met
145                 150                 155                 160

Phe Pro Cys Leu His His Ser Gln Asn Leu Leu Arg Ala Val Ser Asn
                165                 170                 175

Met Leu Gln Lys Ala Arg Gln Thr Leu Glu Phe Tyr Pro Cys Thr Ser
            180                 185                 190

Glu Glu Ile Asp His Glu Asp Ile Thr Lys Asp Lys Thr Ser Thr Val
        195                 200                 205

Glu Ala Cys Leu Pro Leu Glu Leu Thr Lys Asn Glu Ser Cys Leu Asn
    210                 215                 220

Ser Arg Glu Thr Ser Phe Ile Thr Asn Gly Ser Cys Leu Ala Ser Arg
225                 230                 235                 240

Lys Thr Ser Phe Met Met Ala Leu Cys Leu Ser Ser Ile Tyr Glu Asp
                245                 250                 255

Leu Lys Met Tyr Gln Val Glu Phe Lys Thr Met Asn Ala Lys Leu Leu
            260                 265                 270

Met Asp Pro Lys Arg Gln Ile Phe Leu Asp Gln Asn Met Leu Ala Val
        275                 280                 285

Ile Asp Glu Leu Met Gln Ala Leu Asn Phe Asn Ser Glu Thr Val Pro
    290                 295                 300

Gln Lys Ser Ser Leu Glu Glu Pro Asp Phe Tyr Lys Thr Lys Ile Lys
305                 310                 315                 320

Leu Cys Ile Leu Leu His Ala Phe Arg Ile Arg Ala Val Thr Ile Asp
                325                 330                 335
```

```
Arg Val Met Ser Tyr Leu Asn Ala Ser Gly Gly Gly Gly Ser Gly Gly
            340                 345                 350

Gly Gly Ser Gly Gly Gly Gly Ser Ala Pro Ala Arg Ser Pro Ser Pro
        355                 360                 365

Ser Thr Gln Pro Trp Glu His Val Asn Ala Ile Gln Glu Ala Arg Arg
    370                 375                 380

Leu Leu Asn Leu Ser Arg Asp Thr Ala Ala Glu Met Asn Glu Thr Val
385                 390                 395                 400

Glu Val Ile Ser Glu Met Phe Asp Leu Gln Glu Pro Thr Cys Leu Gln
                405                 410                 415

Thr Arg Leu Glu Leu Tyr Lys Gln Gly Leu Arg Gly Ser Leu Thr Lys
            420                 425                 430

Leu Lys Gly Pro Leu Thr Met Met Ala Ser His Tyr Lys Gln His Cys
        435                 440                 445

Pro Pro Thr Pro Glu Thr Ser Cys Ala Thr Gln Ile Ile Thr Phe Glu
    450                 455                 460

Ser Phe Lys Glu Asn Leu Lys Asp Phe Leu Leu Val Ile Pro Phe Asp
465                 470                 475                 480

Cys Trp Glu Pro Val Gln Glu
                485


<210> SEQ ID NO 22
<211> LENGTH: 733
<212> TYPE: PRT
<213> ORGANISM: Artificial Sequence
<220> FEATURE:
<223> OTHER INFORMATION: first polypeptide chain
      (humanhscF8IL12aIL2GMCSF chain)

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Ser Ser Gly Asp Gly Ser Ser Gly Gly Ser
        115                 120                 125

Gly Gly Ala Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Ser Met Pro Phe Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
```

```
        195                 200                 205

Ser Arg Leu Glu Pro Glu Asp Phe Ala Val Tyr Tyr Cys Gln Gln Met
    210                 215                 220

Arg Gly Arg Pro Pro Thr Phe Gly Gln Gly Thr Lys Val Glu Ile Lys
225                 230                 235                 240

Gly Ser Ala Asp Gly Gly Arg Asn Leu Pro Val Ala Thr Pro Asp Pro
                245                 250                 255

Gly Met Phe Pro Cys Leu His His Ser Gln Asn Leu Leu Arg Ala Val
            260                 265                 270

Ser Asn Met Leu Gln Lys Ala Arg Gln Thr Leu Glu Phe Tyr Pro Cys
        275                 280                 285

Thr Ser Glu Glu Ile Asp His Glu Asp Ile Thr Lys Asp Lys Thr Ser
    290                 295                 300

Thr Val Glu Ala Cys Leu Pro Leu Glu Leu Thr Lys Asn Glu Ser Cys
305                 310                 315                 320

Leu Asn Ser Arg Glu Thr Ser Phe Ile Thr Asn Gly Ser Cys Leu Ala
                325                 330                 335

Ser Arg Lys Thr Ser Phe Met Met Ala Leu Cys Leu Ser Ser Ile Tyr
            340                 345                 350

Glu Asp Leu Lys Met Tyr Gln Val Glu Phe Lys Thr Met Asn Ala Lys
        355                 360                 365

Leu Leu Met Asp Pro Lys Arg Gln Ile Phe Leu Asp Gln Asn Met Leu
    370                 375                 380

Ala Val Ile Asp Glu Leu Met Gln Ala Leu Asn Phe Asn Ser Glu Thr
385                 390                 395                 400

Val Pro Gln Lys Ser Ser Leu Glu Glu Pro Asp Phe Tyr Lys Thr Lys
                405                 410                 415

Ile Lys Leu Cys Ile Leu Leu His Ala Phe Arg Ile Arg Ala Val Thr
            420                 425                 430

Ile Asp Arg Val Met Ser Tyr Leu Asn Ala Ser Gly Gly Gly Gly Ser
        435                 440                 445

Gly Gly Gly Gly Ser Gly Gly Gly Gly Ser Ala Pro Thr Ser Ser Ser
    450                 455                 460

Thr Lys Lys Thr Gln Leu Gln Leu Glu His Leu Leu Leu Asp Leu Gln
465                 470                 475                 480

Met Ile Leu Asn Gly Ile Asn Asn Tyr Lys Asn Pro Lys Leu Thr Arg
                485                 490                 495

Met Leu Thr Phe Lys Phe Tyr Met Pro Lys Lys Ala Thr Glu Leu Lys
            500                 505                 510

His Leu Gln Cys Leu Glu Glu Glu Leu Lys Pro Leu Glu Glu Val Leu
        515                 520                 525

Asn Leu Ala Gln Ser Lys Asn Phe His Leu Arg Pro Arg Asp Leu Ile
    530                 535                 540

Ser Asn Ile Asn Val Ile Val Leu Glu Leu Lys Gly Ser Glu Thr Thr
545                 550                 555                 560

Phe Met Cys Glu Tyr Ala Asp Glu Thr Ala Thr Ile Val Glu Phe Leu
                565                 570                 575

Asn Arg Trp Ile Thr Phe Cys Gln Ser Ile Ile Ser Thr Leu Thr Gly
            580                 585                 590

Gly Gly Gly Ser Gly Gly Gly Gly Ser Gly Gly Gly Gly Ser Ala Pro
        595                 600                 605

Ala Arg Ser Pro Ser Pro Ser Thr Gln Pro Trp Glu His Val Asn Ala
    610                 615                 620
```

```
Ile Gln Glu Ala Arg Arg Leu Leu Asn Leu Ser Arg Asp Thr Ala Ala
625                 630                 635                 640

Glu Met Asn Glu Thr Val Glu Val Ile Ser Glu Met Phe Asp Leu Gln
                645                 650                 655

Glu Pro Thr Cys Leu Gln Thr Arg Leu Glu Leu Tyr Lys Gln Gly Leu
            660                 665                 670

Arg Gly Ser Leu Thr Lys Leu Lys Gly Pro Leu Thr Met Met Ala Ser
        675                 680                 685

His Tyr Lys Gln His Cys Pro Pro Thr Pro Glu Thr Ser Cys Ala Thr
    690                 695                 700

Gln Ile Ile Thr Phe Glu Ser Phe Lys Glu Asn Leu Lys Asp Phe Leu
705                 710                 715                 720

Leu Val Ile Pro Phe Asp Cys Trp Glu Pro Val Gln Glu
                725                 730


<210> SEQ ID NO 23
<211> LENGTH: 732
<212> TYPE: PRT
<213> ORGANISM: Artificial Sequence
<220> FEATURE:
<223> OTHER INFORMATION: first polypeptide chain (human
      hscNHS76IL12aIL2GMCSF chain)

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Lys Trp Ser Lys Phe Asp Tyr Trp Gly Gln Gly Thr Leu
            100                 105                 110

Val Thr Val Ser Ser Ser Ser Gly Asp Gly Ser Ser Gly Gly Ser Gly
        115                 120                 125

Gly Ala Ser Ser Ser Glu Leu Thr Gln Asp Pro Ala Val Ser Val Ala
    130                 135                 140

Leu Gly Gln Thr Val Arg Ile Thr Cys Gln Gly Asp Ser Leu Arg Ser
145                 150                 155                 160

Tyr Tyr Ala Ser Trp Tyr Gln Gln Lys Pro Gly Gln Ala Pro Val Leu
                165                 170                 175

Val Ile Tyr Gly Lys Asn Asn Arg Pro Ser Gly Ile Pro Asp Arg Phe
            180                 185                 190

Ser Gly Ser Ser Ser Gly Asn Thr Ala Ser Leu Thr Ile Thr Gly Ala
        195                 200                 205

Gln Ala Glu Asp Glu Ala Asp Tyr Tyr Cys Asn Ser Arg Asp Ser Ser
    210                 215                 220

Gly Asn His Val Val Phe Gly Gly Gly Thr Lys Leu Thr Val Leu Gly
225                 230                 235                 240

Ser Ala Asp Gly Gly Arg Asn Leu Pro Val Ala Thr Pro Asp Pro Gly
```

```
                245                 250                 255

Met Phe Pro Cys Leu His His Ser Gln Asn Leu Leu Arg Ala Val Ser
            260                 265                 270

Asn Met Leu Gln Lys Ala Arg Gln Thr Leu Glu Phe Tyr Pro Cys Thr
        275                 280                 285

Ser Glu Glu Ile Asp His Glu Asp Ile Thr Lys Asp Lys Thr Ser Thr
    290                 295                 300

Val Glu Ala Cys Leu Pro Leu Glu Leu Thr Lys Asn Glu Ser Cys Leu
305                 310                 315                 320

Asn Ser Arg Glu Thr Ser Phe Ile Thr Asn Gly Ser Cys Leu Ala Ser
                325                 330                 335

Arg Lys Thr Ser Phe Met Met Ala Leu Cys Leu Ser Ser Ile Tyr Glu
            340                 345                 350

Asp Leu Lys Met Tyr Gln Val Glu Phe Lys Thr Met Asn Ala Lys Leu
        355                 360                 365

Leu Met Asp Pro Lys Arg Gln Ile Phe Leu Asp Gln Asn Met Leu Ala
    370                 375                 380

Val Ile Asp Glu Leu Met Gln Ala Leu Asn Phe Asn Ser Glu Thr Val
385                 390                 395                 400

Pro Gln Lys Ser Ser Leu Glu Glu Pro Asp Phe Tyr Lys Thr Lys Ile
                405                 410                 415

Lys Leu Cys Ile Leu Leu His Ala Phe Arg Ile Arg Ala Val Thr Ile
            420                 425                 430

Asp Arg Val Met Ser Tyr Leu Asn Ala Ser Gly Gly Gly Gly Ser Gly
        435                 440                 445

Gly Gly Gly Ser Gly Gly Gly Gly Ser Ala Pro Thr Ser Ser Ser Thr
    450                 455                 460

Lys Lys Thr Gln Leu Gln Leu Glu His Leu Leu Leu Asp Leu Gln Met
465                 470                 475                 480

Ile Leu Asn Gly Ile Asn Asn Tyr Lys Asn Pro Lys Leu Thr Arg Met
                485                 490                 495

Leu Thr Phe Lys Phe Tyr Met Pro Lys Lys Ala Thr Glu Leu Lys His
            500                 505                 510

Leu Gln Cys Leu Glu Glu Glu Leu Lys Pro Leu Glu Glu Val Leu Asn
        515                 520                 525

Leu Ala Gln Ser Lys Asn Phe His Leu Arg Pro Arg Asp Leu Ile Ser
    530                 535                 540

Asn Ile Asn Val Ile Val Leu Glu Leu Lys Gly Ser Glu Thr Thr Phe
545                 550                 555                 560

Met Cys Glu Tyr Ala Asp Glu Thr Ala Thr Ile Val Glu Phe Leu Asn
                565                 570                 575

Arg Trp Ile Thr Phe Cys Gln Ser Ile Ile Ser Thr Leu Thr Gly Gly
            580                 585                 590

Gly Gly Ser Gly Gly Gly Gly Ser Gly Gly Gly Gly Ser Ala Pro Ala
        595                 600                 605

Arg Ser Pro Ser Pro Ser Thr Gln Pro Trp Glu His Val Asn Ala Ile
    610                 615                 620

Gln Glu Ala Arg Arg Leu Leu Asn Leu Ser Arg Asp Thr Ala Ala Glu
625                 630                 635                 640

Met Asn Glu Thr Val Glu Val Ile Ser Glu Met Phe Asp Leu Gln Glu
                645                 650                 655

Pro Thr Cys Leu Gln Thr Arg Leu Glu Leu Tyr Lys Gln Gly Leu Arg
            660                 665                 670
```

```
Gly Ser Leu Thr Lys Leu Lys Gly Pro Leu Thr Met Met Ala Ser His
        675                 680                 685

Tyr Lys Gln His Cys Pro Pro Thr Pro Glu Thr Ser Cys Ala Thr Gln
    690                 695                 700

Ile Ile Thr Phe Glu Ser Phe Lys Glu Asn Leu Lys Asp Phe Leu Leu
705                 710                 715                 720

Val Ile Pro Phe Asp Cys Trp Glu Pro Val Gln Glu
                725                 730


<210> SEQ ID NO 24
<211> LENGTH: 3267
<212> TYPE: DNA
<213> ORGANISM: Artificial Sequence
<220> FEATURE:
<223> OTHER INFORMATION: nucleic acid encoding mIL12bscL19-IL2IL12aGMCSF

<400> SEQUENCE: 24

atgtgggagc tggagaaaga cgtttatgtt gtagaggtgg actggactcc cgatgcccct      60

ggagaaacag tgaacctcac ctgtgacacg cctgaagaag atgacatcac ctggacctca     120

gaccagagac atggagtcat aggctctgga aagaccctga ccatcactgt caaagagttt     180

ctagatgctg gccagtacac ctgccacaaa ggaggcgaga ctctgagcca ctcacatctg     240

ctgctccaca agaaggaaaa tggaatttgg tccactgaaa ttttaaaaaa tttcaaaaac     300

aagactttcc tgaagtgtga agcaccaaat tactccggac ggttcacgtg ctcatggctg     360

gtgcaaagaa acatggactt gaagttcaac atcaagagca gtagcagttc ccctgactct     420

cgggcagtga catgtggaat ggcgtctctg tctgcagaga aggtcacact ggaccaaagg     480

gactatgaga agtattcagt gtcctgccag gaggatgtca cctgcccaac tgccgaggag     540

accctgccca ttgaactggc gttggaagca cggcagcaga ataaatatga gaactacagc     600

accagcttct tcatcaggga catcatcaaa ccagacccgc ccaagaactt gcagatgaag     660

cctttgaaga actcacaggt ggaggtcagc tgggagtacc ctgactcctg gagcactccc     720

cattcctact tctccctcaa gttctttgtt cgaatccagc gcaagaaaga aaagatgaag     780

gagacagagg aggggtgtaa ccagaaaggt gcgttcctcg tagagaagac atctaccgaa     840

gtccaatgca aaggcgggaa tgtctgcgtg caagctcagg atcgctatta caattcctcg     900

tgcagcaagt gggcatgtgt tccctgcagg gtccgatccg gatcagccga tggcggtgag     960

gtgcagctgt tggagtctgg gggaggcttg gtacagcctg gggggtccct gagactctcc    1020

tgtgcagcct ctggattcac ctttagcagt ttttcgatga gctgggtccg ccaggctcca    1080

gggaaggggc tggagtgggt ctcatctatt agtggtagtt cgggtaccac atactacgca    1140

gactccgtga agggccggtt caccatctcc agagacaatt ccaagaacac gctgtatctg    1200

caaatgaaca gcctgagagc cgaagacacg gccgtatatt actgtgcgaa accgtttccg    1260

tattttgact actggggcca gggaaccctg gtcaccgtct cgagtggcga tgggtccagt    1320

ggcggtagcg gggcgcgtc cgaaattgtg ttgacgcagt ctccaggcac cctgtctttg    1380

tctccagggg aaagagccac cctctcctgc agggccagtc agagtgttag cagcagcttt    1440

ttagcctggt accagcagaa acctggccag gctcccaggc tcctcatcta ttatgcatcc    1500

agcagggcca ctggcatccc agacaggttc agtggcagtg ggtctgggac agacttcact    1560

ctcaccatca gcagactgga gcctgaagat tttgcagtgt attactgtca gcagacgggt    1620

cgtattccgc cgacgttcgg ccaagggacc aaggtggaaa tcaaagaggg cagaggaagt    1680
```

```
cttctaacat gcggtgacgt ggaggagaat cccggcccta tgtacagcat gcagctcgca   1740

tcctgtgtca cattgacact tgtgctcctt gtcaacagcg cacccacttc aagctccact   1800

tcaagctcta cagcggaagc acagcagcag cagcagcagc agcagcagca gcagcagcac   1860

ctggagcagc tgttgatgga cctacaggag ctcctgagca ggatggagaa ttacaggaac   1920

ctgaaactcc ccaggatgct caccttcaaa ttttacttgc ccaagcaggc cacagaattg   1980

aaagatcttc agtgcctaga agatgaactt ggacctctgc ggcatgttct ggatttgact   2040

caaagcaaaa gctttcaatt ggaagatgct gagaatttca tcagcaatat cagagtaact   2100

gttgtaaaac taaagggctc tgacaacaca tttgagtgcc aattcgatga tgagtcagca   2160

actgtggtgg actttctgag gagatggata gccttctgtc aaagcatcat ctcaacaagc   2220

cctcaaggtg gaggaggttc tggaggcggt ggaagtggtg gcggaggtag cagggtcatt   2280

ccagtctctg gacctgccag gtgtcttagc cagtcccgaa acctgctgaa gaccacagat   2340

gacatggtga agacggccag agaaaaactg aaacattatt cctgcactgc tgaagacatc   2400

gatcatgaag acatcacacg ggaccaaacc agcacattga agacctgttt accactggaa   2460

ctacacaaga acgagagttg cctggctact agagagactt cttccacaac aagagggagc   2520

tgcctgcccc cacagaagac gtctttgatg atgaccctgt gccttggtag catctatgag   2580

gacttgaaga tgtaccagac agagttccag gccatcaacg cagcacttca gaatcacaac   2640

catcagcaga tcattctaga caagggcatg ctggtggcca tcgatgagct gatgcagtct   2700

ctgaatcata atggcgagac tctgcgccag aaacctcctg tgggagaagc agacccttac   2760

agagtgaaaa tgaagctctg catcctgctt cacgccttca gcacccgcgt cgtgaccatc   2820

aacagggtga tgggctatct gagctccgcc ggaggcggtg gaagtggcgg tggaggctct   2880

ggaggtggcg gaagcgcacc cacccgctca cccatcactg tcacccggcc ttggaagcat   2940

gtagaggcca tcaaagaagc cctgaacctc ctggatgaca tgcctgtcac gttgaatgaa   3000

gaggtagaag tcgtctctaa cgagttctcc ttcaagaagc taacatgtgt gcagacccgc   3060

ctgaagatat tcgagcaggg tctacggggc aatttcacca aactcaaggg cgccttgaac   3120

atgacagcca gctactacca gacatactgc cccccaactc cggaaacgga ctgtgaaaca   3180

caagttacca cctatgcgga tttcatagac agccttaaaa cctttctgac tgatatcccc   3240

tttgaatgca aaaaaccagg ccaaaaa                                       3267
```

<210> SEQ ID NO 25
<211> LENGTH: 3279
<212> TYPE: DNA
<213> ORGANISM: Artificial Sequence
<220> FEATURE:
<223> OTHER INFORMATION: nucleic acid encoding mIL12bscF8-IL2IL12aGMCSF

<400> SEQUENCE: 25

```
atgtgggagc tggagaaaga cgtttatgtt gtagaggtgg actggactcc cgatgcccct     60

ggagaaacag tgaacctcac ctgtgacacg cctgaagaag atgacatcac ctggacctca    120

gaccagagac atggagtcat aggctctgga aagaccctga ccatcactgt caaagagttt    180

ctagatgctg gccagtacac ctgccacaaa ggaggcgaga ctctgagcca ctcacatctg    240

ctgctccaca agaaggaaaa tggaatttgg tccactgaaa ttttaaaaaa tttcaaaaac    300

aagactttcc tgaagtgtga agcaccaaat tactccggac ggttcacgtg ctcatggctg    360

gtgcaaagaa acatggactt gaagttcaac atcaagagca gtagcagttc ccctgactct    420

cgggcagtga catgtggaat ggcgtctctg tctgcagaga aggtcacact ggaccaaagg    480
```

```
gactatgaga agtattcagt gtcctgccag gaggatgtca cctgcccaac tgccgaggag    540
accctgccca ttgaactggc gttggaagca cggcagcaga ataaatatga gaactacagc    600
accagcttct tcatcaggga catcatcaaa ccagacccgc ccaagaactt gcagatgaag    660
cctttgaaga actcacaggt ggaggtcagc tgggagtacc ctgactcctg gagcactccc    720
cattcctact tctccctcaa gttctttgtt cgaatccagc gcaagaaaga aaagatgaag    780
gagacagagg aggggtgtaa ccagaaaggt gcgttcctcg tagagaagac atctaccgaa    840
gtccaatgca aaggcgggaa tgtctgcgtg caagctcagg atcgctatta caattcctcg    900
tgcagcaagt gggcatgtgt tccctgcagg gtccgatccg gatcagccga tggcggtgag    960
gtgcagctgt tggagtctgg gggaggcttg gtacagcctg gggggtccct gagactctcc   1020
tgtgcagcct ctggattcac ctttagcctg tttacgatga gctgggtccg ccaggctcca   1080
gggaaggggc tggagtgggt ctcagctatt agtggtagtg gtggtagcac atactacgca   1140
gactccgtga agggccggtt caccatctcc agagacaatt ccaagaacac gctgtatctg   1200
caaatgaaca gcctgagagc cgaggacacg gccgtatatt actgtgcgaa aagtactcat   1260
ttgtatcttt ttgactactg gggccaggga accctggtca ccgtctcgag ttcgagtggc   1320
gatgggtcca gtggcggtag cgggggcgcg tccgaaattg tgttgacgca gtctccaggc   1380
accctgtctt tgtctccagg ggaaagagcc accctctcct gcagggccag tcagagtgtt   1440
agcatgccgt ttttagcctg gtaccagcag aaacctggcc aggctcccag gctcctcatc   1500
tatggtgcat ccagcagggc cactggcatc ccagacaggt tcagtggcag tgggtctggg   1560
acagacttca ctctcaccat cagcagactg gagcctgaag attttgcagt gtattactgt   1620
cagcagatgc gtggtcggcc gccgacgttc ggccaaggga ccaaggtgga aatcaaagag   1680
ggcagaggaa gtcttctaac atgcggtgac gtggaggaga atcccggccc tatgtacagc   1740
atgcagctcg catcctgtgt cacattgaca cttgtgctcc ttgtcaacag cgcacccact   1800
tcaagctcca cttcaagctc tacagcggaa gcacagcagc agcagcagca gcagcagcag   1860
cagcagcagc acctggagca gctgttgatg gacctacagg agctcctgag caggatggag   1920
aattacagga acctgaaact ccccaggatg ctcaccttca aattttactt gcccaagcag   1980
gccacagaat tgaaagatct tcagtgccta gaagatgaac ttggacctct gcggcatgtt   2040
ctggatttga ctcaaagcaa aagctttcaa ttggaagatg ctgagaattt catcagcaat   2100
atcagagtaa ctgttgtaaa actaaagggc tctgacaaca catttgagtg ccaattcgat   2160
gatgagtcag caactgtggt ggactttctg aggagatgga tagccttctg tcaaagcatc   2220
atctcaacaa gccctcaagg tggaggaggt tctggaggcg gtggaagtgg tggcggaggt   2280
agcagggtca ttccagtctc tggacctgcc aggtgtctta gccagtcccg aaacctgctg   2340
aagaccacag atgacatggt gaagacggcc agagaaaaac tgaaacatta ttcctgcact   2400
gctgaagaca tcgatcatga agacatcaca cgggaccaaa ccagcacatt gaagacctgt   2460
ttaccactgg aactacacaa gaacgagagt tgcctggcta ctagagagac ttcttccaca   2520
acaagaggga gctgcctgcc cccacagaag acgtctttga tgatgaccct gtgccttggt   2580
agcatctatg aggacttgaa gatgtaccag acagagttcc aggccatcaa cgcagcactt   2640
cagaatcaca accatcagca gatcattcta gacaagggca tgctggtggc catcgatgag   2700
ctgatgcagt ctctgaatca taatggcgag actctgcgcc agaaacctcc tgtgggagaa   2760
gcagaccctt acagagtgaa aatgaagctc tgcatcctgc ttcacgcctt cagcacccgc   2820
```

```
gtcgtgacca tcaacagggt gatgggctat ctgagctccg ccggaggcgg tggaagtggc   2880

ggtggaggct ctggaggtgg cggaagcgca cccacccgct cacccatcac tgtcacccgg   2940

ccttggaagc atgtagaggc catcaaagaa gccctgaacc tcctggatga catgcctgtc   3000

acgttgaatg aagaggtaga agtcgtctct aacgagttct ccttcaagaa gctaacatgt   3060

gtgcagaccc gcctgaagat attcgagcag ggtctacggg gcaatttcac caaactcaag   3120

ggcgccttga acatgacagc cagctactac cagacatact gcccccccaac tccggaaacg   3180

gactgtgaaa cacaagttac cacctatgcg gatttcatag acagccttaa aacctttctg   3240

actgatatcc cctttgaatg caaaaaacca ggccaaaaa                          3279
```

```
<210> SEQ ID NO 26
<211> LENGTH: 3276
<212> TYPE: DNA
<213> ORGANISM: Artificial Sequence
<220> FEATURE:
<223> OTHER INFORMATION: nucleic acid encoding mIL12bscNHS76-
      IL2IL12aGMCSF

<400> SEQUENCE: 26
```

```
atgtgggagc tggagaaaga cgtttatgtt gtagaggtgg actggactcc cgatgcccct     60

ggagaaacag tgaacctcac ctgtgacacg cctgaagaag atgacatcac ctggacctca    120

gaccagagac atggagtcat aggctctgga aagaccctga ccatcactgt caaagagttt    180

ctagatgctg gccagtacac ctgccacaaa ggaggcgaga ctctgagcca ctcacatctg    240

ctgctccaca agaaggaaaa tggaatttgg tccactgaaa ttttaaaaaa tttcaaaaac    300

aagactttcc tgaagtgtga agcaccaaat tactccggac ggttcacgtg ctcatggctg    360

gtgcaaagaa acatggactt gaagttcaac atcaagagca gtagcagttc ccctgactct    420

cgggcagtga catgtggaat ggcgtctctg tctgcagaga aggtcacact ggaccaaagg    480

gactatgaga agtattcagt gtcctgccag gaggatgtca cctgcccaac tgccgaggag    540

accctgccca ttgaactggc gttggaagca cggcagcaga ataaatatga gaactacagc    600

accagcttct tcatcaggga catcatcaaa ccagacccgc ccaagaactt gcagatgaag    660

cctttgaaga actcacaggt ggaggtcagc tgggagtacc ctgactcctg gagcactccc    720

cattcctact tctccctcaa gttctttgtt cgaatccagc gcaagaaaga aaagatgaag    780

gagacagagg aggggtgtaa ccagaaaggt gcgttcctcg tagagaagac atctaccgaa    840

gtccaatgca aaggcgggaa tgtctgcgtg caagctcagg atcgctatta caattcctcg    900

tgcagcaagt gggcatgtgt tccctgcagg gtccgatccg gatcagccga tggcggtcag    960

gtgcagctgc aggagagcgg ccccggcctg gtgaagccca gcgagaccct gagcctgacc   1020

tgcgccgtga gcggctacag catcagcagc ggctactact ggggctggat caggcagccc   1080

cccggcaagg gcctggagtg gatcggcagc atctaccaca gcggcagcac ctactacaac   1140

cccagcctga agagcagggt gaccatcagc gtggacacca gcaagaacca gttcagcctg   1200

aagctgagca gcgtgaccgc cgccgacacc gccgtgtact actgcgccag ggcaagtgg    1260

agcaagttcg actactgggg ccagggcacc ctggtgaccg tgagcagctc gagtggcgat   1320

gggtccagtg gcggtagcgg gggcgcgtcc agcagcgagc tgacccagga ccccgccgtg   1380

agcgtggccc tgggccagac cgtgaggatc acctgccagg gcgacagcct gaggagctac   1440

tacgccagct ggtaccagca gaagcccggc caggcccccg tgctggtgat ctacggcaag   1500

aacaacaggc ccagcggcat ccccgacagg ttcagcggca gcagcagcgg caacaccgcc   1560
```

agcctgacca tcaccggcgc ccaggccgag gacgaggccg actactactg caacagcagg 1620
gacagcagcg gcaaccacgt ggtgttcggc ggcggcacca agctgaccgt gctggagggc 1680
agaggaagtc ttctaacatg cggtgacgtg gaggagaatc ccggccctat gtacagcatg 1740
cagctcgcat cctgtgtcac attgacactt gtgctccttg tcaacagcgc acccacttca 1800
agctccactt caagctctac agcggaagca cagcagcagc agcagcagca gcagcagcag 1860
cagcagcacc tggagcagct gttgatggac ctacaggagc tcctgagcag gatggagaat 1920
tacaggaacc tgaaactccc caggatgctc accttcaaat tttacttgcc caagcaggcc 1980
acagaattga aagatcttca gtgcctagaa gatgaacttg gacctctgcg gcatgttctg 2040
gatttgactc aaagcaaaag ctttcaattg gaagatgctg agaatttcat cagcaatatc 2100
agagtaactg ttgtaaaact aaagggctct gacaacacat ttgagtgcca attcgatgat 2160
gagtcagcaa ctgtggtgga ctttctgagg agatggatag ccttctgtca aagcatcatc 2220
tcaacaagcc ctcaaggtgg aggaggttct ggaggcggtg gaagtggtgg cggaggtagc 2280
agggtcattc cagtctctgg acctgccagg tgtcttagcc agtcccgaaa cctgctgaag 2340
accacagatg acatggtgaa gacggccaga gaaaaactga aacattattc ctgcactgct 2400
gaagacatcg atcatgaaga catcacacgg gaccaaacca gcacattgaa gacctgttta 2460
ccactggaac tacacaagaa cgagagttgc ctggctacta gagagacttc ttccacaaca 2520
agagggagct gcctgccccc acagaagacg tctttgatga tgaccctgtg ccttggtagc 2580
atctatgagg acttgaagat gtaccagaca gagttccagg ccatcaacgc agcacttcag 2640
aatcacaacc atcagcagat cattctagac aagggcatgc tggtggccat cgatgagctg 2700
atgcagtctc tgaatcataa tggcgagact ctgcgccaga aacctcctgt gggagaagca 2760
gacccttaca gagtgaaaat gaagctctgc atcctgcttc acgccttcag cacccgcgtc 2820
gtgaccatca acagggtgat gggctatctg agctccgccg gaggcggtgg aagtggcggt 2880
ggaggctctg gaggtggcgg aagcgcaccc acccgctcac ccatcactgt cacccggcct 2940
tggaagcatg tagaggccat caaagaagcc ctgaacctcc tggatgacat gcctgtcacg 3000
ttgaatgaag aggtagaagt cgtctctaac gagttctcct tcaagaagct aacatgtgtg 3060
cagacccgcc tgaagatatt cgagcagggt ctacggggca atttcaccaa actcaagggc 3120
gccttgaaca tgacagccag ctactaccag acatactgcc ccccaactcc ggaaacggac 3180
tgtgaaacac aagttaccac ctatgcggat ttcatagaca gccttaaaac ctttctgact 3240
gatatcccct ttgaatgcaa aaaaccaggc caaaaa 3276

<210> SEQ ID NO 27
<211> LENGTH: 4050
<212> TYPE: DNA
<213> ORGANISM: Artificial Sequence
<220> FEATURE:
<223> OTHER INFORMATION: nucleic acid encoding mIL12bscL19-scL19IL12aIL2GMCSF

<400> SEQUENCE: 27
atgtgggagc tggagaaaga cgtttatgtt gtagaggtgg actggactcc cgatgcccct 60
ggagaaacag tgaacctcac ctgtgacacg cctgaagaag atgacatcac ctggacctca 120
gaccagagac atggagtcat aggctctgga aagaccctga ccatcactgt caaagagttt 180
ctagatgctg gccagtacac ctgccacaaa ggaggcgaga ctctgagcca ctcacatctg 240
ctgctccaca agaaggaaaa tggaatttgg tccactgaaa ttttaaaaaa tttcaaaaac 300

-continued

```
aagactttcc tgaagtgtga agcaccaaat tactccggac ggttcacgtg ctcatggctg    360
gtgcaaagaa acatggactt gaagttcaac atcaagagca gtagcagttc ccctgactct    420
cgggcagtga catgtggaat ggcgtctctg tctgcagaga aggtcacact ggaccaaagg    480
gactatgaga agtattcagt gtcctgccag gaggatgtca cctgcccaac tgccgaggag    540
accctgccca ttgaactggc gttggaagca cggcagcaga ataaatatga gaactacagc    600
accagcttct tcatcaggga catcatcaaa ccagacccgc ccaagaactt gcagatgaag    660
cctttgaaga actcacaggt ggaggtcagc tgggagtacc ctgactcctg gagcactccc    720
cattcctact tctccctcaa gttctttgtt cgaatccagc gcaagaaaga aaagatgaag    780
gagacagagg aggggtgtaa ccagaaaggt gcgttcctcg tagagaagac atctaccgaa    840
gtccaatgca aaggcgggaa tgtctgcgtg caagctcagg atcgctatta caattcctcg    900
tgcagcaagt gggcatgtgt tccctgcagg gtccgatccg gatcagccga tggcggtgag    960
gtgcagctgt tggagtctgg gggaggcttg gtacagcctg gggggtccct gagactctcc   1020
tgtgcagcct ctggattcac ctttagcagt ttttcgatga gctgggtccg ccaggctcca   1080
gggaaggggc tggagtgggt ctcatctatt agtggtagtt cgggtaccac atactacgca   1140
gactccgtga agggccggtt caccatctcc agagacaatt ccaagaacac gctgtatctg   1200
caaatgaaca gcctgagagc cgaagacacg gccgtatatt actgtgcgaa accgtttccg   1260
tattttgact actggggcca gggaaccctg gtcaccgtct cgagtggcga tgggtccagt   1320
ggcggtagcg gggcgcgtc cgaaattgtg ttgacgcagt ctccaggcac cctgtctttg   1380
tctccagggg aaagagccac cctctcctgc agggccagtc agagtgttag cagcagcttt   1440
ttagcctggt accagcagaa acctggccag gctcccaggc tcctcatcta ttatgcatcc   1500
agcagggcca ctggcatccc agacaggttc agtggcagtg ggtctgggac agacttcact   1560
ctcaccatca gcagactgga gcctgaagat tttgcagtgt attactgtca gcagacgggt   1620
cgtattccgc cgacgttcgg ccaagggacc aaggtggaaa tcaaagaggg cagaggaagt   1680
cttctaacat gcggtgacgt ggaggagaat cccggcccta tgggctggag cctgatcctc   1740
ctgttcctcg tcgctgtggc tacaggtgtg cactcggagg tgcagctgtt ggagtctggg   1800
ggaggcttgg tacagcctgg ggggtccctg agactctcct gtgcagcctc tggattcacc   1860
tttagcagtt tttcgatgag ctgggtccgc caggctccag ggaaggggct ggagtgggtc   1920
tcatctatta gtggtagttc gggtaccaca tactacgcag actccgtgaa gggccggttc   1980
accatctcca gagacaattc caagaacacg ctgtatctgc aaatgaacag cctgagagcc   2040
gaagacacgg ccgtatatta ctgtgcgaaa ccgtttccgt attttgacta ctggggccag   2100
ggaaccctgg tcaccgtctc gagtggcgat gggtccagtg gcggtagcgg gggcgcgtcc   2160
gaaattgtgt tgacgcagtc tccaggcacc ctgtctttgt ctccagggga aagagccacc   2220
ctctcctgca gggccagtca gagtgttagc agcagctttt tagcctggta ccagcagaaa   2280
cctggccagg ctcccaggct cctcatctat tatgcatcca gcagggccac tggcatccca   2340
gacaggttca gtggcagtgg gtctgggaca gacttcactc tcaccatcag cagactggag   2400
cctgaagatt ttgcagtgta ttactgtcag cagacgggtc gtattccgcc gacgttcggc   2460
caagggacca aggtggaaat caaaggatca gccgatggcg gtagggtcat tccagtctct   2520
ggacctgcca ggtgtcttag ccagtcccga aacctgctga agaccacaga tgacatggtg   2580
aagacggcca gagaaaaact gaaacattat tcctgcactg ctgaagacat cgatcatgaa   2640
gacatcacac gggaccaaac cagcacattg aagacctgtt taccactgga actacacaag   2700
```

```
aacgagagtt gcctggctac tagagagact tcttccacaa caagagggag ctgcctgccc   2760

ccacagaaga cgtctttgat gatgaccctg tgccttggta gcatctatga ggacttgaag   2820

atgtaccaga cagagttcca ggccatcaac gcagcacttc agaatcacaa ccatcagcag   2880

atcattctag acaagggcat gctggtggcc atcgatgagc tgatgcagtc tctgaatcat   2940

aatggcgaga ctctgcgcca gaaacctcct gtgggagaag cagaccctta cagagtgaaa   3000

atgaagctct gcatcctgct tcacgccttc agcacccgcg tcgtgaccat caacagggtg   3060

atgggctatc tgagctccgc cggtggagga ggttctggag gcggtggaag tggtggcgga   3120

ggtagcatgt acagcatgca gctcgcatcc tgtgtcacat tgacacttgt gctccttgtc   3180

aacagcgcac ccacttcaag ctccacttca agctctacag cggaagcaca gcagcagcag   3240

cagcagcagc agcagcagca gcagcacctg gagcagctgt tgatggacct acaggagctc   3300

ctgagcagga tggagaatta caggaacctg aaactcccca ggatgctcac cttcaaattt   3360

tacttgccca agcaggccac agaattgaaa gatcttcagt gcctagaaga tgaacttgga   3420

cctctgcggc atgttctgga tttgactcaa agcaaaagct ttcaattgga agatgctgag   3480

aatttcatca gcaatatcag agtaactgtt gtaaaactaa agggctctga caacacattt   3540

gagtgccaat tcgatgatga gtcagcaact gtggtggact ttctgaggag atggatagcc   3600

ttctgtcaaa gcatcatctc aacaagccct caaggaggcg gtggaagtgg cggtggaggc   3660

tctggaggtg gcggaagcgc acccacccgc tcacccatca ctgtcacccg gccttggaag   3720

catgtagagg ccatcaaaga agccctgaac ctcctggatg acatgcctgt cacgttgaat   3780

gaagaggtag aagtcgtctc taacgagttc tccttcaaga agctaacatg tgtgcagacc   3840

cgcctgaaga tattcgagca gggtctacgg ggcaatttca ccaaactcaa gggcgccttg   3900

aacatgacag ccagctacta ccagacatac tgccccccaa ctccggaaac ggactgtgaa   3960

acacaagtta ccacctatgc ggatttcata gacagcctta aacctttct gactgatatc    4020

ccctttgaat gcaaaaaacc aggccaaaaa                                    4050
```

<210> SEQ ID NO 28
<211> LENGTH: 4074
<212> TYPE: DNA
<213> ORGANISM: Artificial Sequence
<220> FEATURE:
<223> OTHER INFORMATION: nucleic acid encoding mIL12bscF8-scF8IL12aIL2GMCSF

<400> SEQUENCE: 28

```
atgtgggagc tggagaaaga cgtttatgtt gtagaggtgg actggactcc cgatgcccct     60

ggagaaacag tgaacctcac ctgtgacacg cctgaagaag atgacatcac ctggacctca    120

gaccagagac atggagtcat aggctctgga aagaccctga ccatcactgt caaagagttt    180

ctagatgctg gccagtacac ctgccacaaa ggaggcgaga ctctgagcca ctcacatctg    240

ctgctccaca agaaggaaaa tggaatttgg tccactgaaa ttttaaaaaa tttcaaaaac    300

aagactttcc tgaagtgtga agcaccaaat tactccggac ggttcacgtg ctcatggctg    360

gtgcaaagaa acatggactt gaagttcaac atcaagagca gtagcagttc ccctgactct    420

cgggcagtga catgtggaat ggcgtctctg tctgcagaga aggtcacact ggaccaaagg    480

gactatgaga agtattcagt gtcctgccag gaggatgtca cctgcccaac tgccgaggag    540

accctgccca ttgaactggc gttggaagca cggcagcaga ataaatatga gaactacagc    600

accagcttct tcatcaggga catcatcaaa ccagacccgc ccaagaactt gcagatgaag    660
```

```
cctttgaaga actcacaggt ggaggtcagc tgggagtacc ctgactcctg gagcactccc    720
cattcctact tctccctcaa gttctttgtt cgaatccagc gcaagaaaga aaagatgaag    780
gagacagagg aggggtgtaa ccagaaaggt gcgttcctcg tagagaagac atctaccgaa    840
gtccaatgca aaggcgggaa tgtctgcgtg caagctcagg atcgctatta caattcctcg    900
tgcagcaagt gggcatgtgt tccctgcagg gtccgatccg gatcagccga tggcggtgag    960
gtgcagctgt tggagtctgg gggaggcttg gtacagcctg gggggtccct gagactctcc   1020
tgtgcagcct ctggattcac ctttagcctg tttacgatga gctgggtccg ccaggctcca   1080
gggaaggggc tggagtgggt ctcagctatt agtggtagtg gtggtagcac atactacgca   1140
gactccgtga agggccggtt caccatctcc agagacaatt ccaagaacac gctgtatctg   1200
caaatgaaca gcctgagagc cgaggacacg gccgtatatt actgtgcgaa aagtactcat   1260
ttgtatcttt ttgactactg gggccaggga accctggtca ccgtctcgag ttcgagtggc   1320
gatgggtcca gtggcggtag cgggggcgcg tccgaaattg tgttgacgca gtctccaggc   1380
accctgtctt tgtctccagg ggaaagagcc accctctcct gcagggccag tcagagtgtt   1440
agcatgccgt tttagcctg gtaccagcag aaacctggcc aggctcccag gctcctcatc   1500
tatggtgcat ccagcagggc cactggcatc ccagacaggt tcagtggcag tgggtctggg   1560
acagacttca ctctcaccat cagcagactg gagcctgaag attttgcagt gtattactgt   1620
cagcagatgc gtggtcggcc gccgacgttc ggccaaggga ccaaggtgga aatcaaagag   1680
ggcagaggaa gtcttctaac atgcggtgac gtggaggaga atcccggccc tatgggctgg   1740
agcctgatcc tcctgttcct cgtcgctgtg gctacaggtg tgcactcgga ggtgcagctg   1800
ttggagtctg gggggaggctt ggtacagcct ggggggtccc tgagactctc ctgtgcagcc   1860
tctggattca cctttagcct gtttacgatg agctgggtcc gccaggctcc agggaagggg   1920
ctggagtggg tctcagctat tagtggtagt ggtggtagca catactacgc agactccgtg   1980
aagggccggt tcaccatctc cagagacaat tccaagaaca cgctgtatct gcaaatgaac   2040
agcctgagag ccgaggacac ggccgtatat tactgtgcga aagtactca tttgtatctt   2100
tttgactact ggggccaggg aaccctggtc accgtctcga gttcgagtgg cgatgggtcc   2160
agtggcggta gcgggggcgc gtccgaaatt gtgttgacgc agtctccagg caccctgtct   2220
ttgtctccag gggaaagagc caccctctcc tgcagggcca gtcagagtgt tagcatgccg   2280
tttttagcct ggtaccagca gaaacctggc caggctccca ggctcctcat ctatggtgca   2340
tccagcaggg ccactggcat cccagacagg ttcagtggca gtgggtctgg gacagacttc   2400
actctcacca tcagcagact ggagcctgaa gattttgcag tgtattactg tcagcagatg   2460
cgtggtcggc cgccgacgtt cggccaaggg accaaggtgg aaatcaaagg atcagccgat   2520
ggcggtaggg tcattccagt ctctggacct gccaggtgtc ttagccagtc ccgaaacctg   2580
ctgaagacca cagatgacat ggtgaagacg gccagagaaa aactgaaaca ttattcctgc   2640
actgctgaag acatcgatca tgaagacatc acacgggacc aaaccagcac attgaagacc   2700
tgtttaccac tggaactaca caagaacgag agttgcctgg ctactagaga gacttcttcc   2760
acaacaagag ggagctgcct gcccccacag aagacgtctt tgatgatgac cctgtgcctt   2820
ggtagcatct atgaggactt gaagatgtac cagacagagt tccaggccat caacgcagca   2880
cttcagaatc acaaccatca gcagatcatt ctagacaagg gcatgctggt ggccatcgat   2940
gagctgatgc agtctctgaa tcataatggc gagactctgc gccagaaacc tcctgtggga   3000
```

-continued

```
gaagcagacc cttacagagt gaaaatgaag ctctgcatcc tgcttcacgc cttcagcacc   3060

cgcgtcgtga ccatcaacag ggtgatgggc tatctgagct ccgccggtgg aggaggttct   3120

ggaggcggtg gaagtggtgg cggaggtagc atgtacagca tgcagctcgc atcctgtgtc   3180

acattgacac ttgtgctcct tgtcaacagc gcacccactt caagctccac ttcaagctct   3240

acagcggaag cacagcagca gcagcagcag cagcagcagc agcagcagca cctggagcag   3300

ctgttgatgg acctacagga gctcctgagc aggatggaga attacaggaa cctgaaactc   3360

cccaggatgc tcaccttcaa attttacttg cccaagcagg ccacagaatt gaaagatctt   3420

cagtgcctag aagatgaact tggacctctg cggcatgttc tggatttgac tcaaagcaaa   3480

agctttcaat tggaagatgc tgagaatttc atcagcaata tcagagtaac tgttgtaaaa   3540

ctaaagggct ctgacaacac atttgagtgc caattcgatg atgagtcagc aactgtggtg   3600

gactttctga ggagatggat agccttctgt caaagcatca tctcaacaag ccctcaagga   3660

ggcggtggaa gtggcggtgg aggctctgga ggtggcggaa gcgcacccac ccgctcaccc   3720

atcactgtca cccggccttg gaagcatgta gaggccatca aagaagccct gaacctcctg   3780

gatgacatgc ctgtcacgtt gaatgaagag gtagaagtcg tctctaacga gttctccttc   3840

aagaagctaa catgtgtgca gacccgcctg aagatattcg agcagggtct acggggcaat   3900

ttcaccaaac tcaagggcgc cttgaacatg acagccagct actaccagac atactgcccc   3960

ccaactccgg aaacggactg tgaaacacaa gttaccacct atgcggattt catagacagc   4020

cttaaaacct ttctgactga tatccccttt gaatgcaaaa aaccaggcca aaaa         4074
```

<210> SEQ ID NO 29
<211> LENGTH: 4068
<212> TYPE: DNA
<213> ORGANISM: Artificial Sequence
<220> FEATURE:
<223> OTHER INFORMATION: nucleic acid encoding mIL12bscNHS76-
      scNHS76IL12aIL2GMCSF

<400> SEQUENCE: 29

```
atgtgggagc tggagaaaga cgtttatgtt gtagaggtgg actggactcc cgatgcccct     60

ggagaaacag tgaacctcac ctgtgacacg cctgaagaag atgacatcac ctggacctca    120

gaccagagac atggagtcat aggctctgga aagaccctga ccatcactgt caaagagttt    180

ctagatgctg gccagtacac ctgccacaaa ggaggcgaga ctctgagcca ctcacatctg    240

ctgctccaca agaaggaaaa tggaatttgg tccactgaaa ttttaaaaaa tttcaaaaac    300

aagactttcc tgaagtgtga agcaccaaat tactccggac ggttcacgtg ctcatggctg    360

gtgcaaagaa acatggactt gaagttcaac atcaagagca gtagcagttc ccctgactct    420

cgggcagtga catgtggaat ggcgtctctg tctgcagaga aggtcacact ggaccaaagg    480

gactatgaga agtattcagt gtcctgccag gaggatgtca cctgcccaac tgccgaggag    540

accctgccca ttgaactggc gttggaagca cggcagcaga ataaatatga gaactacagc    600

accagcttct tcatcaggga catcatcaaa ccagacccgc ccaagaactt gcagatgaag    660

cctttgaaga actcacaggt ggaggtcagc tgggagtacc ctgactcctg gagcactccc    720

cattcctact tctccctcaa gttctttgtt cgaatccagc gcaagaaaga aaagatgaag    780

gagacagagg aggggtgtaa ccagaaaggt gcgttcctcg tagagaagac atctaccgaa    840

gtccaatgca aaggcgggaa tgtctgcgtg caagctcagg atcgctatta caattcctcg    900

tgcagcaagt gggcatgtgt tccctgcagg gtccgatccg gatcagccga tggcggtcag    960
```

```
gtgcagctgc aggagagcgg ccccggcctg gtgaagccca gcgagaccct gagcctgacc   1020
tgcgccgtga gcggctacag catcagcagc ggctactact ggggctggat caggcagccc   1080
cccggcaagg gcctggagtg gatcggcagc atctaccaca gcggcagcac ctactacaac   1140
cccagcctga agagcagggt gaccatcagc gtggacacca gcaagaacca gttcagcctg   1200
aagctgagca gcgtgaccgc cgccgacacc gccgtgtact actgcgccag gggcaagtgg   1260
agcaagttcg actactgggg ccagggcacc ctggtgaccg tgagcagctc gagtggcgat   1320
gggtccagtg gcggtagcgg gggcgcgtcc agcagcgagc tgacccagga ccccgccgtg   1380
agcgtggccc tgggccagac cgtgaggatc acctgccagg gcgacagcct gaggagctac   1440
tacgccagct ggtaccagca gaagcccggc caggcccccg tgctggtgat ctacggcaag   1500
aacaacaggc ccagcggcat ccccgacagg ttcagcggca gcagcagcgg caacaccgcc   1560
agcctgacca tcaccggcgc ccaggccgag gacgaggccg actactactg caacagcagg   1620
gacagcagcg gcaaccacgt ggtgttcggc ggcggcacca agctgaccgt gctggagggc   1680
agaggaagtc ttctaacatg cggtgacgtg gaggagaatc ccggccctat gggctggagc   1740
ctgatcctcc tgttcctcgt cgctgtggct acaggtgtgc actcgcaggt gcagctgcag   1800
gagagcggcc ccggcctggt gaagcccagc gagaccctga gcctgacctg cgccgtgagc   1860
ggctacagca tcagcagcgg ctactactgg ggctggatca ggcagccccc cggcaagggc   1920
ctggagtgga tcggcagcat ctaccacagc ggcagcacct actacaaccc cagcctgaag   1980
agcagggtga ccatcagcgt ggacaccagc aagaaccagt tcagcctgaa gctgagcagc   2040
gtgaccgccg ccgacaccgc cgtgtactac tgcgccaggg gcaagtggag caagttcgac   2100
tactggggcc agggcaccct ggtgaccgtg agcagctcga gtggcgatgg gtccagtggc   2160
ggtagcgggg gcgcgtccag cagcgagctg acccaggacc ccgccgtgag cgtggccctg   2220
ggccagaccg tgaggatcac ctgccagggc gacagcctga ggagctacta cgccagctgg   2280
taccagcaga agcccggcca ggcccccgtg ctggtgatct acggcaagaa caacaggccc   2340
agcggcatcc ccgacaggtt cagcggcagc agcagcggca acaccgccag cctgaccatc   2400
accggcgccc aggccgagga cgaggccgac tactactgca acagcaggga cagcagcggc   2460
aaccacgtgg tgttcggcgg cggcaccaag ctgaccgtgc tgggatcagc cgatggcggt   2520
agggtcattc cagtctctgg acctgccagg tgtcttagcc agtcccgaaa cctgctgaag   2580
accacagatg acatggtgaa gacggccaga gaaaaactga aacattattc ctgcactgct   2640
gaagacatcg atcatgaaga catcacacgg gaccaaacca gcacattgaa gacctgttta   2700
ccactggaac tacacaagaa cgagagttgc ctggctacta gagagacttc ttccacaaca   2760
agagggagct gcctgccccc acagaagacg tctttgatga tgaccctgtg ccttggtagc   2820
atctatgagg acttgaagat gtaccagaca gagttccagg ccatcaacgc agcacttcag   2880
aatcacaacc atcagcagat cattctagac aagggcatgc tggtggccat cgatgagctg   2940
atgcagtctc tgaatcataa tggcgagact ctgcgccaga aacctcctgt gggagaagca   3000
gacccttaca gagtgaaaat gaagctctgc atcctgcttc acgccttcag cacccgcgtc   3060
gtgaccatca acagggtgat gggctatctg agctccgccg gtggaggagg ttctggaggc   3120
ggtggaagtg gtggcggagg tagcatgtac agcatgcagc tcgcatcctg tgtcacattg   3180
acacttgtgc tccttgtcaa cagcgcaccc acttcaagct ccacttcaag ctctacagcg   3240
gaagcacagc agcagcagca gcagcagcag cagcagcagc agcacctgga gcagctgttg   3300
atggacctac aggagctcct gagcaggatg gagaattaca ggaacctgaa actccccagg   3360
```

```
atgctcacct tcaaatttta cttgcccaag caggccacag aattgaaaga tcttcagtgc   3420

ctagaagatg aacttggacc tctgcggcat gttctggatt tgactcaaag caaaagcttt   3480

caattggaag atgctgagaa tttcatcagc aatatcagag taactgttgt aaaactaaag   3540

ggctctgaca acacatttga gtgccaattc gatgatgagt cagcaactgt ggtggacttt   3600

ctgaggagat ggatagcctt ctgtcaaagc atcatctcaa caagccctca aggaggcggt   3660

ggaagtggcg gtggaggctc tggaggtggc ggaagcgcac ccacccgctc acccatcact   3720

gtcacccggc cttggaagca tgtagaggcc atcaaagaag ccctgaacct cctggatgac   3780

atgcctgtca cgttgaatga agaggtagaa gtcgtctcta acgagttctc cttcaagaag   3840

ctaacatgtg tgcagacccg cctgaagata ttcgagcagg gtctacgggg caatttcacc   3900

aaactcaagg gcgccttgaa catgacagcc agctactacc agacatactg ccccccaact   3960

ccggaaacgg actgtgaaac acaagttacc acctatgcgg atttcataga cagccttaaa   4020

acctttctga ctgatatccc ctttgaatgc aaaaaaccag gccaaaaa                4068
```

<210> SEQ ID NO 30
<211> LENGTH: 3231
<212> TYPE: DNA
<213> ORGANISM: Artificial Sequence
<220> FEATURE:
<223> OTHER INFORMATION: nucleic acid encoding hIL12bscF8-IL2IL12aGMCSF

<400> SEQUENCE: 30

```
atatgggaac tgaagaaaga tgtttatgtc gtagaattgg attggtatcc ggatgcccct     60

ggagaaatgg tggtcctcac ctgtgacacc cctgaagaag atggtatcac ctggaccttg    120

gaccagagca gtgaggtctt aggctctggc aaaaccctga ccatccaagt caaagagttt    180

ggagatgctg gccagtacac ctgtcacaaa ggaggcgagg ttctaagcca ttcgctcctg    240

ctgcttcaca aaaaggaaga tggaatttgg tccactgata ttttaaagga ccagaaagaa    300

cccaaaaata agacctttct aagatgcgag gccaagaatt attctggacg tttcacctgc    360

tggtggctga cgacaatcag tactgatttg acattcagtg tcaaaagcag cagaggctct    420

tctgaccccc aaggggtgac gtgcggagct gctacactct ctgcagagag agtcagaggg    480

gacaacaagg agtatgagta ctcagtggag tgccaggagg acagtgcctg cccagctgct    540

gaggagagtc tgcccattga ggtcatggtg gatgccgttc acaagctcaa gtatgaaaac    600

tacaccagca gcttcttcat cagggacatc atcaaacctg acccacccaa gaacttgcag    660

ctgaagccat taaagaattc tcggcaggtg gaggtcagct gggagtaccc tgacacctgg    720

agtactccac attcctactt ctccctgaca ttctgcgttc aggtccaggg caagagcaag    780

agagaaaaga aagatagagt cttcacggac aagacctcag ccacggtcat ctgccgcaaa    840

aatgccagca ttagcgtgcg ggcccaggac cgctactata gctcatcttg gagcgaatgg    900

gcatctgtgc cctgcagtgg atcagccgat ggcggtgagg tgcagctgtt ggagtctggg    960

ggaggcttgg tacagcctgg ggggtccctg agactctcct gtgcagcctc tggattcacc   1020

tttagcctgt ttacgatgag ctgggtccgc caggctccag ggaaggggct ggagtgggtc   1080

tcagctatta gtggtagtgg tggtagcaca tactacgcag actccgtgaa gggccggttc   1140

accatctcca gagacaattc caagaacacg ctgtatctgc aaatgaacag cctgagagcc   1200

gaggacacgg ccgtatatta ctgtgcgaaa agtactcatt tgtatctttt tgactactgg   1260

ggccagggaa ccctggtcac cgtctcgagt tcgagtggcg atgggtccag tggcggtagc   1320
```

```
gggggcgcgt ccgaaattgt gttgacgcag tctccaggca ccctgtcttt gtctccaggg   1380
gaaagagcca ccctctcctg cagggccagt cagagtgtta gcatgccgtt tttagcctgg   1440
taccagcaga aacctggcca ggctcccagg ctcctcatct atggtgcatc cagcagggcc   1500
actggcatcc cagacaggtt cagtggcagt gggtctggga cagacttcac tctcaccatc   1560
agcagactgg agcctgaaga ttttgcagtg tattactgtc agcagatgcg tggtcggccg   1620
ccgacgttcg gccaagggac caaggtggaa atcaaagagg gcagaggaag tcttctaaca   1680
tgcggtgacg tggaggagaa tcccggccct atgtacagga tgcaactcct gtcttgcatt   1740
gcactaagtc ttgcacttgt cacaaacagt gcacctactt caagttctac aaagaaaaca   1800
cagctacaac tggagcattt actgctggat ttacagatga ttttgaatgg aattaataat   1860
tacaagaatc ccaaactcac caggatgctc acatttaagt tttacatgcc caagaaggcc   1920
acagaactga aacatcttca gtgtctagaa gaagaactca aacctctgga ggaagtgcta   1980
aatttagctc aaagcaaaaa ctttcactta agacccaggg acttaatcag caatatcaac   2040
gtaatagttc tggaactaaa gggatctgaa acaacattca tgtgtgaata tgctgatgag   2100
acagcaacca ttgtagaatt tctgaacaga tggattacct tttgtcaaag catcatctca   2160
acactgactg gtggaggagg ttctggaggc ggtggaagtg gtggcggagg tagcagaaac   2220
ctccccgtgg ccactccaga cccaggaatg ttcccatgcc ttcaccactc ccaaaacctg   2280
ctgagggccg tcagcaacat gctccagaag gccagacaaa ctctagaatt ttacccttgc   2340
acttctgaag agattgatca tgaagatatc acaaaagata aaaccagcac agtggaggcc   2400
tgtttaccat tggaattaac caagaatgag agttgcctaa attccagaga gacctctttc   2460
ataactaatg ggagttgcct ggcctccaga aagacctctt ttatgatggc cctgtgcctt   2520
agtagtattt atgaagactt gaagatgtac caggtggagt tcaagaccat gaatgcaaag   2580
cttctgatgg atcctaagag gcagatcttt ctagatcaaa acatgctggc agttattgat   2640
gagctgatgc aggccctgaa tttcaacagt gagactgtgc cacaaaaatc ctcccttgaa   2700
gaaccggatt tttataaaac taaaatcaag ctctgcatac ttcttcatgc tttcagaatt   2760
cgggcagtga ctattgatag agtgatgagc tatctgaatg cttccggagg cggtggaagt   2820
ggcggtggag gctctggagg tggcggaagc gcacccgccc gctcgcccag ccccagcacg   2880
cagccctggg agcatgtgaa tgccatccag gaggcccggc gtctcctgaa cctgagtaga   2940
gacactgctg ctgagatgaa tgaaacagta gaagtcatct cagaaatgtt tgacctccag   3000
gagccgacct gcctacagac ccgcctggag ctgtacaagc agggcctgcg gggcagcctc   3060
accaagctca agggcccctt gaccatgatg gccagccact acaagcagca ctgccctcca   3120
accccggaaa cttcctgtgc aacccagatt atcacctttg aaagtttcaa agagaacctg   3180
aaggactttc tgcttgtcat cccctttgac tgctgggagc cagtccagga g            3231
```

<210> SEQ ID NO 31
<211> LENGTH: 3966
<212> TYPE: DNA
<213> ORGANISM: Artificial Sequence
<220> FEATURE:
<223> OTHER INFORMATION: nucleic acid encoding hIL12bscF8-scF8IL12aIL2GMCSF

<400> SEQUENCE: 31

```
atatgggaac tgaagaaaga tgtttatgtc gtagaattgg attggtatcc ggatgcccct     60
ggagaaatgg tggtcctcac ctgtgacacc cctgaagaag atggtatcac ctggaccttg    120
```

```
gaccagagca gtgaggtctt aggctctggc aaaaccctga ccatccaagt caaagagttt    180
ggagatgctg gccagtacac ctgtcacaaa ggaggcgagg ttctaagcca ttcgctcctg    240
ctgcttcaca aaaaggaaga tggaatttgg tccactgata ttttaaagga ccagaaagaa    300
cccaaaaata agacctttct aagatgcgag gccaagaatt attctggacg tttcacctgc    360
tggtggctga cgacaatcag tactgatttg acattcagtg tcaaaagcag cagaggctct    420
tctgaccccc aaggggtgac gtgcggagct gctacactct ctgcagagag agtcagaggg    480
gacaacaagg agtatgagta ctcagtggag tgccaggagg acagtgcctg cccagctgct    540
gaggagagtc tgcccattga ggtcatggtg gatgccgttc acaagctcaa gtatgaaaac    600
tacaccagca gcttcttcat cagggacatc atcaaacctg acccacccaa gaacttgcag    660
ctgaagccat taaagaattc tcggcaggtg gaggtcagct gggagtaccc tgacacctgg    720
agtactccac attcctactt ctccctgaca ttctgcgttc aggtccaggg caagagcaag    780
agagaaaaga aagatagagt cttcacggac aagacctcag ccacggtcat ctgccgcaaa    840
aatgccagca ttagcgtgcg ggcccaggac cgctactata gctcatcttg gagcgaatgg    900
gcatctgtgc cctgcagtgg atcagccgat ggcggtgagg tgcagctgtt ggagtctggg    960
ggaggcttgg tacagcctgg ggggtccctg agactctcct gtgcagcctc tggattcacc   1020
tttagcctgt ttacgatgag ctgggtccgc caggctccag ggaaggggct ggagtgggtc   1080
tcagctatta gtggtagtgg tggtagcaca tactacgcag actccgtgaa gggccggttc   1140
accatctcca gagacaattc caagaacacg ctgtatctgc aaatgaacag cctgagagcc   1200
gaggacacgg ccgtatatta ctgtgcgaaa agtactcatt tgtatctttt tgactactgg   1260
ggccagggaa ccctggtcac cgtctcgagt tcgagtggcg atgggtccag tggcggtagc   1320
gggggcgcgt ccgaaattgt gttgacgcag tctccaggca ccctgtcttt gtctccaggg   1380
gaaagagcca ccctctcctg cagggccagt cagagtgtta gcatgccgtt tttagcctgg   1440
taccagcaga aacctggcca ggctcccagg ctcctcatct atggtgcatc cagcagggcc   1500
actggcatcc cagacaggtt cagtggcagt gggtctggga cagacttcac tctcaccatc   1560
agcagactgg agcctgaaga ttttgcagtg tattactgtc agcagatgcg tggtcggccg   1620
ccgacgttcg gccaagggac caaggtggaa atcaaagagg gcagaggaag tcttctaaca   1680
tgcggtgacg tggaggagaa tcccggccct atgggctgga gcctgatcct cctgttcctc   1740
gtcgctgtgg ctacaggtgt gcactcggag gtgcagctgt tggagtctgg gggaggcttg   1800
gtacagcctg gggggtccct gagactctcc tgtgcagcct ctggattcac ctttagcctg   1860
tttacgatga gctgggtccg ccaggctcca gggaaggggc tggagtgggt ctcagctatt   1920
agtggtagtg gtggtagcac atactacgca gactccgtga agggccggtt caccatctcc   1980
agagacaatt ccaagaacac gctgtatctg caaatgaaca gcctgagagc cgaggacacg   2040
gccgtatatt actgtgcgaa aagtactcat ttgtatcttt ttgactactg gggccaggga   2100
accctggtca ccgtctcgag ttcgagtggc gatgggtcca gtggcggtag cgggggcgcg   2160
tccgaaattg tgttgacgca gtctccaggc accctgtctt tgtctccagg ggaaagagcc   2220
accctctcct gcagggccag tcagagtgtt agcatgccgt ttttagcctg gtaccagcag   2280
aaacctggcc aggctcccag gctcctcatc tatggtgcat ccagcagggc cactggcatc   2340
ccagacaggt tcagtggcag tgggtctggg acagacttca ctctcaccat cagcagactg   2400
gagcctgaag attttgcagt gtattactgt cagcagatgc gtggtcggcc gccgacgttc   2460
ggccaaggga ccaaggtgga aatcaaagga tcagccgatg gcggtagaaa cctccccgtg   2520
```

```
gccactccag acccaggaat gttcccatgc cttcaccact cccaaaacct gctgagggcc   2580

gtcagcaaca tgctccagaa ggccagacaa actctagaat tttacccttg cacttctgaa   2640

gagattgatc atgaagatat cacaaaagat aaaaccagca cagtggaggc ctgtttacca   2700

ttggaattaa ccaagaatga gagttgccta aattccagag agacctcttt cataactaat   2760

gggagttgcc tggcctccag aaagacctct tttatgatgg ccctgtgcct tagtagtatt   2820

tatgaagact tgaagatgta ccaggtggag ttcaagacca tgaatgcaaa gcttctgatg   2880

gatcctaaga ggcagatctt tctagatcaa aacatgctgg cagttattga tgagctgatg   2940

caggccctga atttcaacag tgagactgtg ccacaaaaat cctcccttga agaaccggat   3000

ttttataaaa ctaaaatcaa gctctgcata cttcttcatg ctttcagaat tcgggcagtg   3060

actattgata gagtgatgag ctatctgaat gcttccggtg gaggaggttc tggaggcggt   3120

ggaagtggtg gcggaggtag cgcacctact tcaagttcta caaagaaaac acagctacaa   3180

ctggagcatt tactgctgga tttacagatg attttgaatg gaattaataa ttacaagaat   3240

cccaaactca ccaggatgct cacatttaag ttttacatgc ccaagaaggc cacagaactg   3300

aaacatcttc agtgtctaga agaagaactc aaacctctgg aggaagtgct aaatttagct   3360

caaagcaaaa actttcactt aagacccagg gacttaatca gcaatatcaa cgtaatagtt   3420

ctggaactaa agggatctga aacaacattc atgtgtgaat atgctgatga gacagcaacc   3480

attgtagaat ttctgaacag atggattacc ttttgtcaaa gcatcatctc aacactgact   3540

ggaggcggtg gaagtggcgg tggaggctct ggaggtggcg gaagcgcacc cgcccgctcg   3600

cccagcccca gcacgcagcc ctgggagcat gtgaatgcca tccaggaggc ccggcgtctc   3660

ctgaacctga gtagagacac tgctgctgag atgaatgaaa cagtagaagt catctcagaa   3720

atgtttgacc tccaggagcc gacctgccta cagacccgcc tggagctgta caagcagggc   3780

ctgcggggca gcctcaccaa gctcaagggc cccttgacca tgatggccag ccactacaag   3840

cagcactgcc ctccaacccc ggaaacttcc tgtgcaaccc agattatcac ctttgaaagt   3900

ttcaaagaga acctgaagga ctttctgctt gtcatcccct ttgactgctg ggagccagtc   3960

caggag                                                              3966
```

<210> SEQ ID NO 32
<211> LENGTH: 3960
<212> TYPE: DNA
<213> ORGANISM: Artificial Sequence
<220> FEATURE:
<223> OTHER INFORMATION: nucleic acid encoding hIL12bscNHS76-
scNHS76IL12aIL2GMCSF

<400> SEQUENCE: 32

```
atatgggaac tgaagaaaga tgtttatgtc gtagaattgg attggtatcc ggatgcccct     60

ggagaaatgg tggtcctcac ctgtgacacc cctgaagaag atggtatcac ctggaccttg    120

gaccagagca gtgaggtctt aggctctggc aaaaccctga ccatccaagt caaagagttt    180

ggagatgctg gccagtacac ctgtcacaaa ggaggcgagg ttctaagcca ttcgctcctg    240

ctgcttcaca aaaaggaaga tggaatttgg tccactgata ttttaaagga ccagaaagaa    300

cccaaaaata agacctttct aagatgcgag gccaagaatt attctggacg tttcacctgc    360

tggtggctga cgacaatcag tactgatttg acattcagtg tcaaaagcag cagaggctct    420

tctgaccccc aaggggtgac gtgcggagct gctacactct ctgcagagag agtcagaggg    480

gacaacaagg agtatgagta ctcagtggag tgccaggagg acagtgcctg cccagctgct    540
```

```
gaggagagtc tgcccattga ggtcatggtg gatgccgttc acaagctcaa gtatgaaaac    600
tacaccagca gcttcttcat cagggacatc atcaaacctg acccacccaa gaacttgcag    660
ctgaagccat taaagaattc tcggcaggtg gaggtcagct gggagtaccc tgacacctgg    720
agtactccac attcctactt ctccctgaca ttctgcgttc aggtccaggg caagagcaag    780
agagaaaaga aagatagagt cttcacggac aagacctcag ccacggtcat ctgccgcaaa    840
aatgccagca ttagcgtgcg ggcccaggac cgctactata gctcatcttg gagcgaatgg    900
gcatctgtgc cctgcagtgg atcagccgat ggcggtcagg tgcagctgca ggagagcggc    960
cccggcctgg tgaagcccag cgagaccctg agcctgacct gcgccgtgag cggctacagc   1020
atcagcagcg gctactactg ggctggatc aggcagcccc ccggcaaggg cctggagtgg    1080
atcggcagca tctaccacag cggcagcacc tactacaacc ccagcctgaa gagcagggtg   1140
accatcagcg tggacaccag caagaaccag ttcagcctga agctgagcag cgtgaccgcc   1200
gccgacaccg ccgtgtacta ctgcgccagg ggcaagtgga gcaagttcga ctactggggc   1260
cagggcaccc tggtgaccgt gagcagctcg agtggcgatg ggtccagtgg cggtagcggg   1320
ggcgcgtcca gcagcgagct gacccaggac cccgccgtga gcgtggccct gggccagacc   1380
gtgaggatca cctgccaggg cgacagcctg aggagctact acgccagctg gtaccagcag   1440
aagcccggcc aggcccccgt gctggtgatc tacggcaaga acaacaggcc cagcggcatc   1500
cccgacaggt tcagcggcag cagcagcggc aacaccgcca gcctgaccat caccggcgcc   1560
caggccgagg acgaggccga ctactactgc aacagcaggg acagcagcgg caaccacgtg   1620
gtgttcggcg gcggcaccaa gctgaccgtg ctggagggca gaggaagtct tctaacatgc   1680
ggtgacgtgg aggagaatcc cggccctatg ggctggagcc tgatcctcct gttcctcgtc   1740
gctgtggcta caggtgtgca ctcgcaggtg cagctgcagg agagcggccc cggcctggtg   1800
aagcccagcg agaccctgag cctgacctgc gccgtgagcg gctacagcat cagcagcggc   1860
tactactggg gctggatcag gcagcccccc ggcaagggcc tggagtggat cggcagcatc   1920
taccacagcg gcagcaccta ctacaacccc agcctgaaga gcagggtgac catcagcgtg   1980
gacaccagca agaaccagtt cagcctgaag ctgagcagcg tgaccgccgc cgacaccgcc   2040
gtgtactact gcgccagggg caagtggagc aagttcgact actggggcca gggcaccctg   2100
gtgaccgtga gcagctcgag tggcgatggg tccagtggcg gtagcggggg cgcgtccagc   2160
agcgagctga cccaggaccc cgccgtgagc gtggccctgg gccagaccgt gaggatcacc   2220
tgccagggcg acagcctgag gagctactac gccagctggt accagcagaa gcccggccag   2280
gcccccgtgc tggtgatcta cggcaagaac aacaggccca gcggcatccc cgacaggttc   2340
agcggcagca gcagcggcaa caccgccagc ctgaccatca ccggcgccca ggccgaggac   2400
gaggccgact actactgcaa cagcagggac agcagcggca accacgtggt gttcggcggc   2460
ggcaccaagc tgaccgtgct gggatcagcc gatggcggta gaaacctccc cgtggccact   2520
ccagacccag gaatgttccc atgccttcac cactcccaaa acctgctgag ggccgtcagc   2580
aacatgctcc agaaggccag acaaactcta gaattttacc cttgcacttc tgaagagatt   2640
gatcatgaag atatcacaaa agataaaacc agcacagtgg aggcctgttt accattggaa   2700
ttaaccaaga atgagagttg cctaaattcc agagagacct ctttcataac taatgggagt   2760
tgcctggcct ccagaaagac ctcttttatg atggccctgt gccttagtag tatttatgaa   2820
gacttgaaga tgtaccaggt ggagttcaag accatgaatg caaagcttct gatggatcct   2880
```

```
aagaggcaga tctttctaga tcaaaacatg ctggcagtta ttgatgagct gatgcaggcc   2940

ctgaatttca acagtgagac tgtgccacaa aaatcctccc ttgaagaacc ggatttttat   3000

aaaactaaaa tcaagctctg catacttctt catgctttca gaattcgggc agtgactatt   3060

gatagagtga tgagctatct gaatgcttcc ggtggaggag gttctggagg cggtggaagt   3120

ggtggcggag gtagcgcacc tacttcaagt tctacaaaga aaacacagct acaactggag   3180

catttactgc tggatttaca gatgattttg aatggaatta ataattacaa gaatcccaaa   3240

ctcaccagga tgctcacatt taagttttac atgcccaaga aggccacaga actgaaacat   3300

cttcagtgtc tagaagaaga actcaaacct ctggaggaag tgctaaattt agctcaaagc   3360

aaaaactttc acttaagacc cagggactta atcagcaata tcaacgtaat agttctggaa   3420

ctaaagggat ctgaaacaac attcatgtgt gaatatgctg atgagacagc aaccattgta   3480

gaatttctga acagatggat taccttttgt caaagcatca tctcaacact gactggaggc   3540

ggtggaagtg gcggtggagg ctctggaggt ggcggaagcg cacccgcccg ctcgcccagc   3600

cccagcacgc agccctggga gcatgtgaat gccatccagg aggcccggcg tctcctgaac   3660

ctgagtagag acactgctgc tgagatgaat gaaacagtag aagtcatctc agaaatgttt   3720

gacctccagg agccgacctg cctacagacc cgcctggagc tgtacaagca gggcctgcgg   3780

ggcagcctca ccaagctcaa gggccccttg accatgatgg ccagccacta caagcagcac   3840

tgccctccaa ccccggaaac ttcctgtgca acccagatta tcacctttga aagtttcaaa   3900

gagaacctga aggactttct gcttgtcatc ccctttgact gctgggagcc agtccaggag   3960
```

```
<210> SEQ ID NO 33
<211> LENGTH: 6
<212> TYPE: PRT
<213> ORGANISM: Artificial Sequence
<220> FEATURE:
<223> OTHER INFORMATION: linker 1-linker between scFv and cytokine

<400> SEQUENCE: 33

Gly Ser Ala Asp Gly Gly
1               5


<210> SEQ ID NO 34
<211> LENGTH: 15
<212> TYPE: PRT
<213> ORGANISM: Artificial Sequence
<220> FEATURE:
<223> OTHER INFORMATION: linker 2-(linker between cytokines) or (linker
      between scFv and cytokine)

<400> SEQUENCE: 34

Gly Gly Gly Gly Ser Gly Gly Gly Gly Ser Gly Gly Gly Gly Ser
1               5                   10                  15


<210> SEQ ID NO 35
<211> LENGTH: 15
<212> TYPE: PRT
<213> ORGANISM: Artificial Sequence
<220> FEATURE:
<223> OTHER INFORMATION: linker 3-(linker between cytokines) or (linker
      between scFv and cytokine)

<400> SEQUENCE: 35

Ser Ser Ser Ser Gly Ser Ser Ser Ser Gly Ser Ser Ser Ser Gly
1               5                   10                  15


<210> SEQ ID NO 36
```

```
<211> LENGTH: 108
<212> TYPE: PRT
<213> ORGANISM: Artificial Sequence
<220> FEATURE:
<223> OTHER INFORMATION: targeting moiety L19VL

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105


<210> SEQ ID NO 37
<211> LENGTH: 114
<212> TYPE: PRT
<213> ORGANISM: Artificial Sequence
<220> FEATURE:
<223> OTHER INFORMATION: targeting moiety L19VH

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val


<210> SEQ ID NO 38
<211> LENGTH: 108
<212> TYPE: PRT
<213> ORGANISM: Artificial Sequence
<220> FEATURE:
<223> OTHER INFORMATION: targeting moiety F8VL

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Met Pro
            20                  25                  30

Phe Leu Ala Trp Tyr Gln Gln Lys Pro Gly Gln Ala Pro Arg Leu Leu
```

```
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105


<210> SEQ ID NO 39
<211> LENGTH: 118
<212> TYPE: PRT
<213> ORGANISM: Artificial Sequence
<220> FEATURE:
<223> OTHER INFORMATION: targeting moiety F8VH

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115


<210> SEQ ID NO 40
<211> LENGTH: 108
<212> TYPE: PRT
<213> ORGANISM: Artificial Sequence
<220> FEATURE:
<223> OTHER INFORMATION: targeting moiety NHS76VL

<400> SEQUENCE: 40

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105
```

```
<210> SEQ ID NO 41
<211> LENGTH: 117
<212> TYPE: PRT
<213> ORGANISM: Artificial Sequence
<220> FEATURE:
<223> OTHER INFORMATION: targeting moiety NHS76VH

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Lys Trp Ser Lys Phe Asp Tyr Trp Gly Gln Gly Thr Leu
            100                 105                 110

Val Thr Val Ser Ser
        115
```

PROTEIN HETERODIMER AND USE THEREOF

This application is a National Stage Application and claims priority under 35 U.S.C. § 371 to Patent Cooperation Treaty application PCT/CN2020/086755, filed Apr. 24, 2020, which claims the benefit of Chinese application CN201910351987.4, filed Apr. 27, 2019. Priority is claimed to these applications and the disclosures of these prior applications are considered part of the disclosure of this application and to the extent allowed the entire contents of the aforementioned applications are incorporated herein by reference.

TECHNICAL FIELD

The present application relates to the field of tumor treatment, and in particular, relates to a protein heterodimer and uses thereof.

BACKGROUND ART

Tumor is a disease that seriously threatens the health of human beings. In recent years, immunotherapy, as a new therapy, has shown great potential in tumor treatment. Cytokine is a very important immune signal in the body, and cytokine fusion protein technology is another popular field for tumor immunotherapy today. This technology is to fuse two or more types of cytokines together by using the genetic engineering technology based on the fact that these cytokines have the same or related functional activities but with different targets respectively. However, the current tumor treatment using the cytokine fusion protein technology is still unsatisfactory, and there is much room for improvement.

SUMMARY OF THE INVENTION

The present application provides a protein heterodimer, comprising a first polypeptide chain and a second polypeptide chain different from the first polypeptide chain, wherein the first polypeptide chain comprises IL12a, and the second polypeptide chain comprises IL12b; the protein heterodimer further comprises IL2 or a functional fragment thereof, GMCSF or a functional fragment thereof, and one or more targeting moieties; and the IL2 or the functional fragment thereof is located in the first polypeptide chain or in the second polypeptide chain, the GMCSF or the functional fragment thereof is located in the first polypeptide chain or in the second polypeptide chain, and the one or more targeting moieties are each independently located in the first polypeptide chain or in the second polypeptide chain.

In some embodiments, the first polypeptide chain and the second polypeptide chain form the heterodimer through an interaction between the IL12a and the IL12b.

In some embodiments, the first polypeptide chain further comprises the IL2 or the functional fragment thereof, and the IL2 or the functional fragment thereof is directly or indirectly linked to the IL12a.

In some embodiments, in the first polypeptide chain of the protein heterodimer, the C-terminal of the IL2 or of the functional fragment thereof is directly or indirectly linked to the N-terminal of the IL12a or of the functional fragment thereof.

In some embodiments, in the first polypeptide chain of the protein heterodimer, the N-terminal of the IL2 or of the functional fragment thereof is directly or indirectly linked to the C-terminal of the IL12a or of the functional fragment thereof.

In some embodiments, the first polypeptide chain further comprises the GMCSF or the functional fragment thereof.

In some embodiments, in the first polypeptide chain of the protein heterodimer, the GMCSF or the functional fragment thereof is directly or indirectly linked to the IL12a or the functional fragment thereof.

In some embodiments, in the first polypeptide chain of the protein heterodimer, the N-terminal of the GMCSF or of the functional fragment thereof is directly or indirectly linked to the C-terminal of the IL12a or of the functional fragment thereof.

In some embodiments, in the first polypeptide chain of the protein heterodimer, the GMCSF or the functional fragment thereof is directly or indirectly linked to the IL2 or the functional fragment thereof.

In some embodiments, in the first polypeptide chain of the protein heterodimer, the N-terminal of the GMCSF or of the functional fragment thereof is directly or indirectly linked to the C-terminal of the IL2 or of the functional fragment thereof.

In some embodiments, the IL2 or the functional fragment thereof, the IL12a or the functional fragment thereof, and the GMCSF or the functional fragment thereof are sequentially comprised in the first polypeptide chain from the N-terminal to the C-terminal.

In some embodiments, the first polypeptide chain further comprises at least one of the targeting moieties.

In some embodiments, the at least one targeting moiety is directly or indirectly linked to the IL12a or the functional fragment thereof.

In some embodiments, the C-terminal of the at least one targeting moiety is directly or indirectly linked to the N-terminal of the IL2 or of the functional fragment thereof.

In some embodiments, the targeting moiety, the IL12a or the functional fragment thereof, the IL2 or the functional fragment thereof, and the GMCSF or the functional fragment thereof are sequentially comprised in the first polypeptide chain of the protein heterodimer from the N-terminal to the C-terminal.

In some embodiments, the second polypeptide chain further comprises at least one of the targeting moieties, and the at least one targeting moiety is directly or indirectly linked to the IL12b.

In some embodiments, the N-terminal of the at least one targeting moiety is directly or indirectly linked to the C-terminal of the IL12b or of the functional fragment thereof.

In some embodiments, the IL2 or the functional fragment thereof, the IL12a or the functional fragment thereof, and the GMCSF or the functional fragment thereof are sequentially comprised in the first polypeptide chain of the protein heterodimer from the N-terminal to the C-terminal; the IL12b or the functional fragment thereof and the targeting moiety.

In some embodiments, the targeting moiety, the IL12a or the functional fragment thereof, the IL2 or the functional fragment thereof, and the GMCSF or the functional fragment thereof are sequentially comprised in the first polypeptide chain of the protein heterodimer from the N-terminal to the C-terminal, and the IL12b or the functional fragment thereof and the targeting moiety are sequentially comprised in the second polypeptide chain from the N-terminal to the C-terminal.

In some embodiments, the IL12a or the functional fragment thereof, the IL12b or the functional fragment thereof, the IL2 or the functional fragment thereof, and the GMCSF or the functional fragment thereof are derived from mammal.

In some embodiments, the IL12a or the functional fragment thereof, the IL12b or the functional fragment thereof, the IL2 or the functional fragment thereof, and the GMCSF or the functional fragment thereof are derived from the same species.

In some embodiments, the same species is human.

In some embodiments, the protein heterodimer comprises a plurality of targeting moieties, which are the same.

In some embodiments, the protein heterodimer comprises a plurality of targeting moieties, at least two of which are different from each other.

In some embodiments, the one or more targeting moieties are capable of specifically binding to a tumor-associated antigen.

In some embodiments, the tumor-associated antigen is selected from the group consisting of: an EDB domain of fibronectin, an EDA domain of fibronectin, and/or a necrotic region.

In some embodiments, the one or more targeting moieties comprise an antibody or an antigen-binding fragment thereof.

In some embodiments, the antigen-binding fragment is selected from the group consisting of Fab, Fab', $F(ab')_2$, $F(ab)_2$, dAb, an isolated complementarity determining region CDR, Fv and scFv.

In some embodiments, the targeting moiety is scFv.

In some embodiments, the targeting moiety comprises an amino acid sequence as set forth in any one in the group consisting of: SEQ ID NOs: 1-3.

In some embodiments, the indirect linking comprises linking via a linker.

In some embodiments, the linker is a peptide linker.

In some embodiments, the one or more targeting moieties are linked to the IL12a and/or the IL12b via the linker.

In some embodiments, the linker comprises a thrombin cleavage site.

In some embodiments, the linker comprises an amino acid sequence as set forth in any one in the group consisting of SEQ ID NOs: 33-35.

In some embodiments, the first polypeptide chain comprises an amino acid sequence as set forth in any one in the group consisting of SEQ ID NOs: 17-23.

In some embodiments, the second polypeptide chain comprises an amino acid sequence as set forth in any one in the group consisting of SEQ ID NOs: 12-16.

In some embodiments, wherein, a) the first polypeptide chain comprises an amino acid sequence as set forth in SEQ ID NO: 17 and the second polypeptide chain comprises an amino acid sequence as set forth in SEQ ID NO: 12; and
b) the first polypeptide chain comprises an amino acid sequence as set forth in SEQ ID NO: 17 and the second polypeptide chain comprises an amino acid sequence as set forth in SEQ ID NO: 13; and
c) the first polypeptide chain comprises an amino acid sequence as set forth in SEQ ID NO: 17 and the second polypeptide chain comprises an amino acid sequence as set forth in SEQ ID NO: 14; and
d) the first polypeptide chain comprises an amino acid sequence as set forth in SEQ ID NO: 18 and the second polypeptide chain comprises an amino acid sequence as set forth in SEQ ID NO: 12; and
e) the first polypeptide chain comprises an amino acid sequence as set forth in SEQ ID NO: 19 and the second polypeptide chain comprises an amino acid sequence as set forth in SEQ ID NO: 13; and
f) the first polypeptide chain comprises an amino acid sequence as set forth in SEQ ID NO: 20 and the second polypeptide chain comprises an amino acid sequence as set forth in SEQ ID NO: 14; and
g) the first polypeptide chain comprises an amino acid sequence as set forth in SEQ ID NO: 21 and the second polypeptide chain comprises an amino acid sequence as set forth in SEQ ID NO: 15; and
h) the first polypeptide chain comprises an amino acid sequence as set forth in SEQ ID NO: 22 and the second polypeptide chain comprises an amino acid sequence as set forth in SEQ ID NO: 15; and
i) the first polypeptide chain comprises an amino acid sequence as set forth in SEQ ID NO: 23 and the second polypeptide chain comprises an amino acid sequence as set forth in SEQ ID NO: 16.

The present application provides a nucleic acid molecule or nucleic acid molecules encoding the protein heterodimer.

In some embodiments, the nucleic acid molecule comprises an amino acid sequence as set forth in any one in the group consisting of SEQ ID NOs: 24-32.

The present application provides a vector comprising the nucleic acid molecule.

The present application provides a cell expressing the encoding the protein heterodimer, or the nucleic acid molecule or the vector.

The present application provides a method for preparing the protein heterodimer, comprising the following step: culturing the cell.

The present application provides a pharmaceutical composition comprising the protein heterodimer.

The present application provides use of the protein heterodimer or the pharmaceutical composition in the preparation of a drug for preventing, alleviating or treating a tumor.

In some embodiments, the tumor comprises a solid tumor.

In some embodiments, the tumor comprises melanoma.

The present application provides a method for preventing, alleviating or treating a tumor, comprising administering the heterodimer and/or the pharmaceutical composition to a subject in need thereof.

Those skilled in the art can easily perceive other aspects and advantages of the present application from the detailed description below. The detailed description below only shows and describes exemplary embodiments of the present application. As will be appreciated by those skilled in the art, the content of the present application enables those skilled in the art to make changes to the disclosed specific embodiments without departing from the spirit and scope of the invention involved in the present application. Correspondingly, the accompanying drawings and the descriptions in the specification of the present application are merely for an exemplary rather than restrictive purpose.

BRIEF DESCRIPTION OF THE DRAWINGS

The specific features of the present invention involved in the present application are listed in the appended claims. The characteristics and advantages of the present invention involved in the present application can be better understood by referring to the exemplary embodiments and the accompanying drawings described in detail below. The accompanying drawings are briefly illustrated as follows:

FIGS. 3-11 show the structures of protein heterodimers of the present application;

DETAILED DESCRIPTION OF THE PREFERRED EMBODIMENTS

Figure 1:
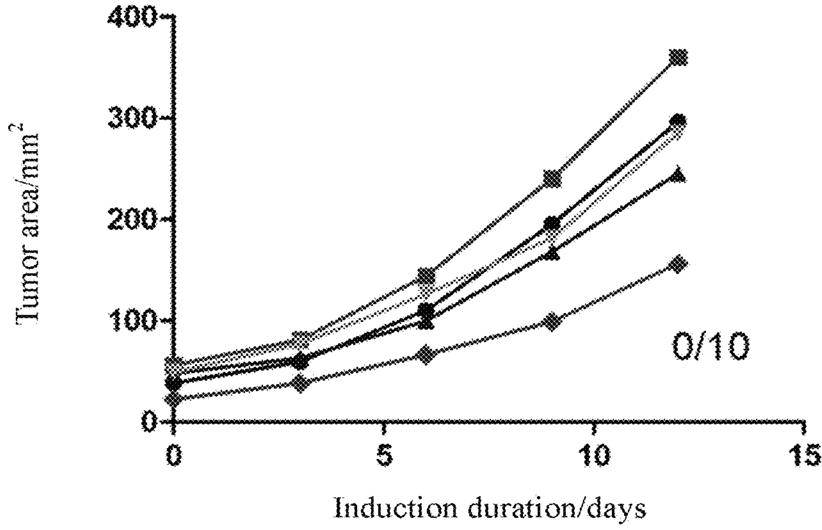
FIG. 1 shows the effect of regulating and expressing GFP on the growth of tumors in mice.

The embodiments of the invention of the present application will be illustrated by specific examples below. Those familiar with this technology can easily understand other advantages and effects of the invention of the present application from the content disclosed in the specification.

In the present application, the term "protein heterodimer" generally refers to a dimer structure composed of two different polypeptide chains. In the present application, the protein heterodimer may include a first polypeptide chain and a second polypeptide chain. The first polypeptide chain is different from the second polypeptide chain, wherein the first polypeptide chain may include IL12a, and the second polypeptide chain may include IL12b.

In the present application, the term "polypeptide chain" generally refers to a chain structure formed by linking a plurality of amino acids to each other and containing a plurality of peptide bonds. In the present application, the "polypeptide chain" may be a "first polypeptide chain" or a "second polypeptide chain", wherein the first polypeptide chain is different from the second polypeptide chain. In the present application, the first polypeptide chain may include IL12a. In some cases, the first polypeptide chain may also include one or more in the group consisting of IL2 or a functional fragment thereof, GMCSF or a functional fragment thereof, and one or more targeting moieties. The second polypeptide chain may include IL12b. In some cases, the first polypeptide chain may also include one or more in the group consisting of: IL2 or a functional fragment thereof, GMCSF or a functional fragment thereof, and one or more targeting moieties.

In the present application, the term "targeting moiety" generally refers to a type of moiety that acts on certain special tissues and cells. For example, the targeting moiety is capable of specifically targeting a tumor-associated antigen. In the present application, the targeting moiety includes an antibody or an antigen-binding fragment thereof.

In the present application, the term "tumor-associated antigen" (TAA) generally refers to an antigen molecule existing on a tumor cell or a normal cell. The tumor-associated antigen may include: an embryonic protein, a glycoprotein antigen and a squamous cell antigen. The tumor-associated antigen may be selected from the group consisting of: an EDB domain of fibronectin, an EDA domain of fibronectin, and a necrotic region.

In the present application, the term "antigen-binding fragment" generally refers to a fragment having an antigen-binding activity. In the present application, the antigen-binding fragment may be selected from the group consisting of Fab, Fab', F(ab')2, F(ab)2, dAb, an isolated complementarity determining region (CDR), Fv and scFv.

In the present application, the term "antibody" is capable of specifically recognizing and/or neutralizing a polypeptide molecule of a specific antigen. A basic four-chain antibody unit is a heterotetrameric glycoprotein, which may be composed of two identical light chains and two identical heavy chains. In the case of IgG, each light chain may be linked to each heavy chain by a covalent disulfide bond, and two heavy chains may be linked to each other by a disulfide bond. Each heavy chain has a variable domain (VH) at the N-terminal, followed by three (for a and y types) or four (for p and F isotypes) constant domains (CH).

In the present application, the terms "IL12a", "IL12b", "IL2", and "GMCSF" may be considered as "cytokines". The "cytokine" generally refers to a class of small molecular proteins synthesized and secreted by stimulating immune cells (such as monocytes, macrophages, T cells, B cells, NK cells, etc.) and certain non-immune cells (such as endothelial cells, epidermal cells, fibroblasts, etc.), showing a broad spectrum of biological activities. The cytokine plays an important role in regulating inter-cellular interaction as well as cell growth and differentiation. In the present application, the cytokine may be one or more selected from the group consisting of: interleukin (IL) and a colony stimulating factor (CSF). The interleukin generally refers to a cytokine produced by lymphocytes, monocytes or other non-mononuclear cells. In the present application, the interleukin may be one or more selected from the group consisting of: IL12 and IL2. In the present application, the colony stimulating factor generally refers to a cytokine capable of stimulating different hematopoietic stem cells to form cell colonies in a semi-solid medium. In the present application, the colony stimulating factor may be a granulocyte macrophage colony stimulating factor (GMCSF).

In the present application, the term "IL12" generally refers to interleukin-12. IL12 may play an important role in regulating inter-cellular interaction, immune regulation, hematopoiesis, and inflammation. An IL12 molecule is generally a heterodimer typically including two subunits, namely, a p40 subunit (40 kd) and a p35 subunit (35 kd) respectively, which are linked together via a disulfide bond. In the present application, IL12 containing the p35 subunit (35 kd) may be represented as IL12a, and IL12 containing the p40 subunit (40 kd) may be represented as IL12b. For example, in murine-derived IL12 (mIL12), the p35 subunit may include an amino acid sequence as set forth in SEQ ID NO: 4, and the p40 subunit may include an amino acid sequence as set forth in SEQ ID NO: 5. For another example, in human-derived IL12 (hIL12), the p35 subunit may include an amino acid sequence as set forth in SEQ ID NO: 6, and the p40 subunit may include an amino acid sequence as set forth in SEQ ID NO: 7.

In the present application, the term "IL2" generally refers to interleukin-2. IL2 plays an important role in regulating inter-cellular interaction, immune regulation, hematopoiesis, and inflammation. For example, murine-derived IL2 (mIL2) may include an amino acid sequence as set forth in SEQ ID NO:8. For another example, human-derived IL2 (hIL2) may include an amino acid sequence as set forth in SEQ ID NO:9.

In the present application, the term "GMCSF" generally refers to a granulocyte macrophage colony stimulating factor. The GMCSF may have 4 α-helix bundle structures. For example, murine-derived GMCSF (mGMCSF) may include an amino acid sequence as set forth in SEQ ID NO:10. For another example, human-derived GMCSF (hGMCSF) may include an amino acid sequence as set forth in SEQ ID NO:11.

In the present application, the term "functional fragment" generally refers to a fragment that retains a certain specific function. For example, a functional fragment of IL2 refers to a fragment that retains the function of IL2. For example, the functional fragment of IL2 may be an IL2 fragment (GenBank: AAA59139.1), and in some cases, the functional fragment of IL2 may also be an IL2 fragment (GenBank: AAA59141.1).

In the present application, the term "directly link" is opposite to the term "indirectly link", and the term "directly link" generally refers to a direct linkage. For example, the direct linkage may be a situation where substances (for example, the same or different cytokines and/or targeting moieties) are directly linked without a spacer. The spacer may be a linker. For example, the linker may be a peptide linker. The term "indirectly link" generally refers to a situation where substances (for example, the same or different cytokines and/or targeting moieties) are not directly linked. For example, the indirectly linking may be a situation where a linkage is performed via a spacer. For example, the C-terminal of IL2 or of the functional fragment thereof is directly linked to or indirectly linked via a linker to the N-terminal of IL12a or of the functional fragment thereof. For another example, the N-terminal of GMCSF or of the functional fragment thereof is directly linked to or indirectly linked via a linker to the C-terminal of IL12a or of the functional fragment thereof.

In the present application, the term "nucleic acid molecule" generally refers to a biological macromolecular compound polymerized from many nucleotides. In terms of different chemical compositions, the nucleic acid molecules may be classified into ribonucleic acids (RNAs for short) and deoxyribonucleic acids (DNAs for short). In the present application, the nucleic acid molecule encodes the protein heterodimer, and may include a nucleotide sequence as set forth in any one of SEQ ID NOs. 24-32.

In the present application, the term "vector" generally refers to a nucleic acid molecule capable of self-replication in a suitable host cell. It transfers an inserted nucleic acid molecule into and/or between host cells. The vector may include a vector mainly for inserting DNA or RNA into cells, a vector mainly for replicating DNA or RNA, and a vector mainly for expressing DNA or RNA transcription and/or translation. The vector may also include a carrier having a variety of the functions defined above. The vector may be a polynucleotide that may be transcribed and translated into a polypeptide when introduced into a suitable host cell. Generally, the vector may produce a desired expression product by culturing a suitable host cell containing the vector.

In the present application, the term "cell" generally refers to an individual cell, a cell line or a cell culture, which may contain or already contains the nucleic acid molecule described in the present application or the vector described in the present application, or is capable of expressing the protein heterodimer described in the present application. The cell may include a progeny of a single host cell. Due to natural, accidental or deliberate mutations, progeny cells and original parent cells may not necessarily be identical in terms of morphology or genome as long as they are capable of expressing the protein heterodimer described in the present application or containing the nucleic acid molecule or vector described in the present application. In the present application, a cell capable of expressing the protein heterodimer described in the present application may be obtained by transfecting a B16 (rtTA) tumor cell or a 293A cell with a virus of the expression vector.

In the present application, the term "tumor" generally refers to or describes a physiological condition of mammals, with the typical feature consisting in the disorder of cell proliferation or survival. For example, the tumor may include a solid tumor. For another example, the tumor may be melanoma.

In the present application, the term "solid tumor" generally refers to a tangible mass that may be diagnosed by clinical examination (such as X-ray photography, CT scanning, B-scan ultrasonography or palpation, etc.). In the present application, the solid tumor may be melanoma.

In the present application, the term "melanoma" generally refers to a pigmented nevus with malignant transformation. The melanoma may develop from a nevus with the properties of a junctional nevus or a compound nevus, with the manifestation of symptoms such as sudden incidence or rapid growth and continuously deepened color of a pigmented nevus.

Protein Heterodimer

In one aspect, the present application provides a protein heterodimer, comprising a first polypeptide chain and a second polypeptide chain different from the first polypeptide chain, wherein the first polypeptide chain comprises IL12a, and the second polypeptide chain comprises IL12b; the protein heterodimer further comprises IL2 or a functional fragment thereof, GMCSF or a functional fragment thereof, and one or more targeting moieties; and the IL2 or the functional fragment thereof is located in the first polypeptide chain or in the second polypeptide chain, the GMCSF or the functional fragment thereof is located in the first polypeptide chain or in the second polypeptide chain, and the one or more targeting moieties are each independently located in the first polypeptide chain or in the second polypeptide chain.

In the present application, the protein heterodimer may be a cytokine fusion protein, where the cytokines, i.e., two or more of IL12, IL2 and GMCSF, are fused together through the gene recombination technology. The protein heterodimer not only may have the unique biological activities of the constituent factors thereof, but also may exert biological functions that are not possessed by a single cytokine through the complementary and synergistic effects of biological activities, and may even produce some new structures and biological functions.

In the present application, the cytokine may be selected from the group consisting of: IL12, IL2 and GMCSF.

In the present application, the protein heterodimer may include one or more targeting moieties, wherein the targeting moieties may be the same or different. In the present application, the targeting moiety in the protein heterodimer includes an antibody or an antigen-binding fragment thereof, wherein the antigen-binding fragment may be selected from the group consisting of: Fab, Fab', F(ab')2, F(ab)2, dAb, an isolated complementarity determining region (CDR), Fv and scFv.

In the present application, the targeting moiety of the protein heterodimer may be selected from the group consisting of: L19$V_L$, L19$V_H$, F8$V_L$, F8$V_H$, NHS76$V_L$, and NHS76$V_H$.

In the present application, the targeting portion of the protein heterodimer may include a sequence as set forth in any one of SEQ ID NOs: 1-3.

In the present application, the indirect linking includes linking that may be performed via a linker. For example, the linker may be a linker peptide. In the present application, the linker may include an amino acid sequence as set forth in any one in the group consisting of: SEQ ID NOs: 33-35.

For example, the cytokines may be linked to each other via the linker. In the present application, the IL12a, IL12b, IL2 and GMCSF may be linked to one another via the linker peptide. For example, the linker peptide may include an amino acid sequence as set forth in SEQ ID NO. 34 or SEQ ID NO. 35.

For example, the cytokine and the targeting moiety may be linked by the linker. In the present application, the targeting moiety of the protein heterodimer may be linked to the IL12a, IL12b, IL2 and GMCSF via the linker peptide. For example, the linker peptide may include an amino acid sequence as set forth in any one of SEQ ID NOs: 33-35.

In the present application, the first polypeptide chain of the protein heterodimer further includes the IL2 or the functional fragment thereof, and the IL2 or the functional fragment thereof is directly or indirectly linked to the IL12a.

In the present application, the C-terminal of the IL2 or of the functional fragment thereof in the first polypeptide chain is directly or indirectly linked to the N-terminal of the IL12a or of the functional fragment thereof.

In the present application, the N-terminal of the IL2 or of the functional fragment thereof in the first polypeptide chain is directly or indirectly linked to the C-terminal of the IL12a or of the functional fragment thereof.

In the present application, the first polypeptide chain of the protein heterodimer further includes the GMCSF or the functional fragment thereof.

In the present application, the GMCSF or the functional fragment thereof in the first polypeptide chain is directly or indirectly linked to the IL12a or the functional fragment thereof.

In the present application, the N-terminal of the GMCSF or of the functional fragment thereof in the first polypeptide chain is directly or indirectly linked to the C-terminal of the IL12a or of the functional fragment thereof.

In the present application, the GMCSF or the functional fragment thereof in the first polypeptide chain is directly or indirectly linked to the IL2 or the functional fragment thereof.

In the present application, the N-terminal of the GMCSF or of the functional fragment thereof in the first polypeptide chain is directly or indirectly linked to the C-terminal of the IL2 or of the functional fragment thereof.

In the present application, the IL2 or the functional fragment thereof, the IL12a or the functional fragment thereof, and the GMCSF or the functional fragment thereof are sequentially included in the first polypeptide chain from the N-terminal to the C-terminal.

In the present application, the first polypeptide chain of the protein heterodimer further includes at least one of the targeting moieties.

In the present application, the at least one targeting moiety in the first polypeptide chain of the protein heterodimer is directly or indirectly linked to the IL12a or the functional fragment thereof.

In the present application, the C-terminal of the at least one targeting moiety in the first polypeptide chain of the protein heterodimer is directly or indirectly linked to the N-terminal of the IL2 or of the functional fragment thereof.

In the present application, the one or more targeting moieties, the IL12a or the functional fragment thereof, the IL2 or the functional fragment thereof, and the GMCSF or the functional fragment thereof are sequentially included in the first polypeptide chain of the protein heterodimer from the N-terminal to the C-terminal.

In the present application, the second polypeptide chain of the protein heterodimer further includes at least one of the targeting moieties, and the at least one targeting moiety is directly or indirectly linked to the IL12b.

In the present application, in the second polypeptide chain of the protein heterodimer, the N-terminal of the at least one targeting moiety is directly or indirectly linked to the C-terminal of the IL12b or of the functional fragment thereof.

In the present application, the IL2 or the functional fragment thereof, the IL12a or the functional fragment thereof, and the GMCSF or the functional fragment thereof are sequentially included in the first polypeptide chain of the protein heterodimer from the N-terminal to the C-terminal, and the IL12b or the functional fragment thereof and the targeting moiety are sequentially included in the second polypeptide chain from the N-terminal to the C-terminal.

In the present application, the targeting moiety, the IL12a or the functional fragment thereof, the IL2 or the functional fragment thereof, and the GMCSF or the functional fragment thereof are sequentially included in the first polypeptide chain of the protein heterodimer from the N-terminal to the C-terminal, and the IL12b or the functional fragment thereof and the targeting moiety are sequentially included in the second polypeptide chain from the N-terminal to the C-terminal.

In the present application, the IL12a or the functional fragment thereof, the IL12b or the functional fragment thereof, the IL2 or the functional fragment thereof, and the GMCSF or the functional fragment thereof in the protein heterodimer are derived from the same species.

In the present application, the IL12a or the functional fragment thereof, the IL12b or the functional fragment thereof, the IL2 or the functional fragment thereof, and the GMCSF or the functional fragment thereof in the protein heterodimer may be derived from human, and the human-derived IL12a, IL12b, IL2 and GMSCF may be written as hIL12a, hIL12b, hIL2 and hGMSCF.

In the present application, the IL12a or the functional fragment thereof, the IL12b or the functional fragment thereof, the IL2 or the functional fragment thereof, and the GMCSF or the functional fragment thereof in the protein heterodimer may be derived from mice, and the murine-derived IL12a, IL12b, IL2 and GMSCF may be written as mIL12a, mIL12b, mIL2 and mGMSCF.

In the present application, the protein heterodimer may include a plurality of targeting moieties, which are the same.

In the present application, the protein heterodimer may include a plurality of targeting moieties, at least two of which are different from each other.

In the present application, the first polypeptide chain may include the IL2 or the functional fragment thereof, and the second polypeptide chain may include the GMCSF or the functional fragment thereof.

In the present application, the first polypeptide chain may include the GMCSF or a functional fragment thereof; and the second polypeptide chain may include the IL2 or the functional fragment thereof.

In the present application, the first polypeptide chain may include a targeting moiety, which may be located at the N-terminal and/or the C-terminal of the first polypeptide chain; and the second polypeptide chain may include a targeting moiety, which may be located at the N-terminal and/or the C-terminal of the second polypeptide chain.

In the present application, the first polypeptide chain of the protein heterodimer may sequentially include the IL12a or the functional fragment thereof, the IL2 or the functional fragment thereof, and the GMCSF or the functional fragment thereof from the N-terminal to the C-terminal, wherein the C-terminal of the IL12a or of the functional fragment thereof is directly or indirectly linked to the N-terminal of the IL2 or of the functional fragment thereof, and the C-terminal of the IL2 or of the functional fragment thereof is directly or indirectly linked to the N-terminal of the GMCSF or of the functional fragment thereof. The first polypeptide chain of the protein heterodimer may sequentially include the targeting moiety, the IL12a or the functional fragment thereof, the IL2 or the functional fragment thereof, and the GMCSF or the functional fragment thereof from the N-terminal to the C-terminal, wherein the C-terminal of the targeting moiety is directly or indirectly linked to the N-terminal of the IL12a or of the functional fragment thereof; the C-terminal of the IL12a or of the functional fragment thereof is directly or indirectly linked to the N-terminal of the IL2 or of the functional fragment thereof; and the C-terminal of the IL2 or of the functional fragment thereof is directly or indirectly linked to the N-terminal of the GMCSF or of the functional fragment thereof.

In the present application, the first polypeptide chain of the protein heterodimer may sequentially include the IL2 or the functional fragment thereof, the IL12a or the functional fragment thereof, and the GMCSF or the functional fragment thereof from the N-terminal to the C-terminal, wherein the C-terminal of the IL2 or of the functional fragment thereof is directly or indirectly linked to the N-terminal of the IL12a or of the functional fragment thereof, and the C-terminal of the IL12a or of the functional fragment thereof is directly or indirectly linked to the N-terminal of the GMCSF or of the functional fragment thereof.

In the present application, the first polypeptide chain of the protein heterodimer may sequentially include the IL12b or the functional fragment thereof and the targeting moiety from the N-terminal to the C-terminal. Herein, the C-terminal of the IL12b or of the functional fragment thereof is directly or indirectly linked to the N-terminal of the targeting moiety.

In the present application, the first polypeptide chain of the protein heterodimer may sequentially include the targeting moiety, the IL12a or the functional fragment thereof, the IL2 or the functional fragment thereof, and the GMCSF or the functional fragment thereof from the N-terminal to the C-terminal; and the second polypeptide chain may sequentially include the IL12b or the functional fragment thereof and the targeting moiety from the N-terminal to the C-terminal. The first polypeptide chain of the protein heterodimer may sequentially include the IL2 or the functional fragment thereof, the IL12a or the functional fragment thereof, and the GMCSF or the functional fragment thereof from the N-terminal to the C-terminal; and the second polypeptide chain may sequentially include the IL12b or the functional fragment thereof and the targeting moiety from the N-terminal to the C-terminal.

In the present application, in the first polypeptide chain of the protein heterodimer, the C-terminal of the targeting moiety may be directly or indirectly linked to the N-terminal of the IL12a or of the functional fragment thereof, the C-terminal of the IL12a or of the functional fragment thereof may be directly or indirectly linked to the N-terminal of the IL2 or of the functional fragment thereof, the C-terminal of the IL2 or of the functional fragment thereof may be directly or indirectly linked to the N-terminal of the GMCSF or of the functional fragment thereof, and in the second polypeptide chain, the C-terminal of the IL12b or of the functional fragment thereof may be directly or indirectly linked to the N-terminal of the targeting moiety. The C-terminal of the IL2 or of the functional fragment thereof may be directly or indirectly linked to the N-terminal of the IL12a or of the functional fragment thereof, the C-terminal of the IL12a or of the functional fragment thereof may be directly or indirectly linked to the N-terminal of the GMCSF or of the functional fragment thereof, and in the second polypeptide chain, the C-terminal of the IL12b or of the functional fragment thereof may be directly or indirectly linked to the N-terminal of the targeting moiety.

The IL12a and IL12b per se may be covalently bonded via disulfide bond. In the present application, the first polypeptide chain and the second polypeptide chain may be bonded by the disulfide bond between the IL12a and the IL12b to form the protein molecule. In some embodiments, a nucleotide sequence encoding a self-cleaving peptide may be included between a nucleotide sequence encoding the first polypeptide chain and a nucleotide sequence encoding the second polypeptide chain. For example, when the expression vector containing the nucleotide sequence above is transcribed and translated, the position of the self-cleavage peptide will be cut to form the protein heterodimer that includes the first polypeptide chain and the second polypeptide chain and is formed via the disulfide bond.

In the present application, the targeting moiety may be selected from: L19$V_L$ (with an amino acid sequence that may be as set forth in SEQ ID NO. 36), L19$V_H$ (with an amino acid sequence that may be as set forth in SEQ ID NO. 37), F8$V_L$ (with an amino acid sequence that may be as set forth in SEQ ID NO. 38), F8$V_H$ (with an amino acid sequence that may be as set forth in SEQ ID NO. 39), NHS76$V_L$ (with an amino acid sequence that may be as set forth in SEQ ID NO. 40), and NHS76$V_H$ (with an amino acid sequence that may be as set forth in SEQ ID NO. 41).

For example, in the protein heterodimer, the C-terminal of the IL12b may be fused to the N-terminal of the L19$V_H$ and the C-terminal of the L19$V_H$ may be fused to the N-terminal of the L19$V_L$ to form a second polypeptide chain, and the C-terminal of the IL2 may be fused to the N-terminal of the IL12a and the C-terminal of the IL12a may be fused to the N-terminal of the GMCSF to form a first polypeptide chain, thereby forming a protein heterodimer IL12b-L19$V_H$-L19$V_L$-IL2-IL12a-GMCSF.

For example, in the protein heterodimer, the C-terminal of the IL12b may be fused to the N-terminal of the F8$V_H$ and the C-terminal of the F8$V_H$ may be fused to the N-terminal of the L19$V_L$ to form a second polypeptide chain, and the C-terminal of the IL2 may be fused to the N-terminal of the IL12a and the C-terminal of the IL12a may be fused to the N-terminal of the GMCSF to form a first polypeptide chain, thereby forming a protein heterodimer IL12b-F8$V_H$-F8$V_L$-IL2-IL12a-GMCSF.

For example, in the protein heterodimer, the C-terminal of the IL12b may be fused to the N-terminal of the NHS76$V_H$ and the C-terminal of the NHS76$V_H$ may be fused to a N-terminal of the NHS76VL to form a second polypeptide chain, and the C-terminal of the IL2 may be fused to the N-terminal of the IL12a and the C-terminal of the IL12a may be fused to the N-terminal of the GMCSF to form a first polypeptide chain, thereby forming a protein heterodimer IL112b-NHS76$V_H$-NHS76$V_L$-IL2-IL12a-GMCSF.

For example, in the protein heterodimer, the C-terminal of the IL12b may be fused to the N-terminal of the L19$V_H$ and the C-terminal of the L19$V_H$ may be fused to the N-terminal of the L19$V_L$ to form a second polypeptide chain; and the C-terminal of the L19$V_H$ may be fused to the N-terminal of the L19$V_L$, the C-terminal of the L19$V_L$ may be fused to the N-terminal of the IL2, the C-terminal of IL2 may be fused to the N-terminal of IL12a, and the C-terminal of the IL12a may be fused to the N terminal of GMCSF to form a first polypeptide chain, thereby forming a protein heterodimer IL12b-L19$V_H$-L19$V_L$-L19$V_H$-L19$V_L$-IL2-IL12a-GMCSF.

For example, in the protein heterodimer, the C-terminal of the IL12b may be fused to the N-terminal of the F8$V_H$, the C-terminal of the F8$V_H$ may be fused to the N-terminal of the F8$V_L$ to form a second polypeptide chain; and the C-terminal of the F8$V_H$ may be fused to the N-terminal of the F8$V_L$, the C-terminal of the F8$V_L$ may be fused to the N-terminal of the IL2, the C-terminal of the IL2 may be fused to the N-terminal of the IL12a, and the C-terminal of the IL12a may be fused to the N-terminal of the GMCSF to form a first polypeptide chain, thereby forming a protein heterodimer IL12b-F8$V_H$-F8$V_L$-F8$V_H$-F8$V_L$-IL2-IL12a-GMCSF.

For example, in the protein heterodimer, the C-terminal of the IL12b may be fused to the N-terminal of the NHS76$V_H$, and the C-terminal of the NHS76$V_H$ may be fused to the N-terminal of the NHS76$V_L$ to form a second polypeptide chain; and the C-terminal of the NHS76$V_H$ may be fused to the N-terminal of the NHS76$V_L$, the C-terminal of the NHS76$V_L$ may be fused to the N-terminal of the IL2, the C-terminal of the IL2 may be fused to the N-terminal of the IL12a, and the C-terminal of the IL12a may be fused to the N-terminal of the GMCSF to form a first polypeptide chain, thereby forming a protein heterodimer IL12b-NHS76$V_H$-NHS76$V_L$-NHS76$V_H$-NHS76$V_L$-IL2-IL12a-GMCSF.

In the present application, the first polypeptide chain may include a sequence as set forth in any one of SEQ ID NOs. 17-23.

In the present application, the second polypeptide chain may include a sequence as set forth in any one of SEQ ID NOs. 12-16.

In the present application, the protein heterodimer may include a sequence as set forth in any one of SEQ ID NOs. 12-23.

For example, in the protein heterodimer, the C-terminal of the mIL12b may be fused to the N-terminal of the L19$V_H$, and the C-terminal of the L19$V_H$ may be fused to the N-terminal of the L19$V_L$ to form a second polypeptide chain (with an amino acid sequence that may be as set forth in SEQ ID NO 12); and the C-terminal of the mIL2 may be fused to the N-terminal of the mIL12a, and the C-terminal of the mIL12a may be fused to the N-terminal of the mGMCSF to form a first polypeptide chain (with an amino acid sequence that may be as set forth in SEQ ID NO. 17), thereby forming a protein heterodimer of mIL12b-L19$V_H$-L19$V_L$-mIL2-mIL12a-mGMCSF.

For example, in the protein heterodimer, the C-terminal of the mIL12b may be fused to the N-terminal of the F8$V_H$, and the C-terminal of the F8$V_H$ may be fused to the N-terminal of the F8$V_L$ to form a second polypeptide chain (with an amino acid sequence that may be as set forth in SEQ ID NO. 13); and the C-terminal of the mIL2 may be fused to the N-terminal of the mIL12a, and the C-terminal of the mIL12a may be fused to the N-terminal of the mGMCSF to form a first polypeptide chain (with an amino acid sequence that may be as set forth in SEQ ID NO. 17), thereby forming a protein heterodimer mIL12b-F8$V_H$-F8$V_L$-mIL2-mIL12a-mGMCSF.

For example, in the protein molecule, the C-terminal of the mIL12b may be fused to the N-terminal of the NHS76$V_H$, and the C-terminal of the NHS76$V_H$ may be fused to the N-terminal of the NHS76$V_L$ to form a second polypeptide chain (with an amino acid sequence that may be as set forth in SEQ ID NO. 14); and the C-terminal of the mIL2 may be fused to the N-terminal of the mIL12a, and the C-terminal of the mIL12a may be fused to the N-terminal of the mGMCSF to form a first polypeptide chain (with an amino acid sequence that may be as set forth in SEQ ID NO. 17), thereby forming a protein heterodimer mIL12b-NHS76$V_H$-NHS76$V_L$-mIL2-mIL12a-mGMCSF.

For example, in the protein molecule, the C-terminal of the mIL12b may be fused to the N-terminal of the L19$V_H$, and the C-terminal of the L19$V_H$ may be fused to the N-terminal of the L19$V_L$ to form a second polypeptide chain (with an amino acid sequence that may be as set forth in SEQ ID NO. 12), and the C-terminal of the L19$V_H$ may be fused to the N-terminal of the L19$V_L$, the C-terminal of the L19$V_L$ may be fused to the N-terminal of the mIL12a, the C-terminal of the mIL12a may be fused to the N-terminal of the mIL2, and the C-terminal of the mIL2 may be fused to the N-terminal of the mGMCSF to form a first polypeptide chain (with an amino acid sequence that may be as set forth in SEQ ID NO. 18), thereby forming a protein heterodimer mIL12b-L19$V_H$-L19$V_L$-L19$V_H$-L19$V_L$-mIL12a-mIL2-mGMCSF.

For example, in the protein molecule, the C-terminal of the mIL12b may be fused to the N-terminal of the F8$V_H$, and the C-terminal of the F8$V_H$ may be fused to the N-terminal of the F8$V_L$ to form a second polypeptide chain (with an amino acid sequence that may be as set forth in SEQ ID NO. 13); and the C-terminal of the F8$V_H$ may be fused to the N-terminal of the F8$V_L$, the C-terminal of the F8$V_L$ may be fused to the N-terminal of the mIL12a, the C-terminal of the mIL12a may be fused to the N-terminal of the mIL2, and the C-terminal of the mIL2 may be fused to the N-terminal of the mGMCSF to form a first polypeptide chain (with an amino acid sequence that may be as set forth in SEQ ID NO. 19), thereby forming a protein heterodimer m L12b-F8$V_H$-F8$V_L$-F8$V_H$-F8$V_L$-mIL12a-mIL2-mGMCSF.

For example, in the protein molecule, the C-terminal of the mIL12b may be fused to the N-terminal of the NHS76$V_H$, and the C-terminal of the NHS76$V_H$ may be fused to the N-terminal of the NHS76$V_L$ to form a second polypeptide chain (with an amino acid sequence that may be as set forth in SEQ ID NO. 14); and the C-terminal of the NHS76$V_H$ may be fused to the N-terminal of the NHS76$V_L$, the C-terminal of the NHS76$V_L$ may be fused to the N-terminal of the mIL12a, the C-terminal of the mIL12a may be fused to the N-terminal of the mIL2, and the C-terminal of the mIL2 may be fused to the N-terminal of the GMCSF to form a first polypeptide chain (with an amino acid sequence that may be as set forth in SEQ ID NO. 20), thereby forming a protein heterodimer mIL12b-NHS76$V_H$-NHS76$V_L$-NHS76$V_H$-NHS76$V_L$-mIL12a-mIL2-mGMCSF.

For example, in the protein molecule, the C-terminal of the hIL12b may be fused to the N-terminal of the F8$V_H$, and the C-terminal of the F8$V_H$ may be fused to the N-terminal of the F8$V_L$ to form a second polypeptide chain (with an amino acid sequence that may be as set forth in SEQ ID NO. 15); and the C-terminal of the hIL2 may be fused to the N-terminal of the hIL12a, and the C-terminal of the hIL12a may be fused to the N-terminal of the hGMCSF to form a first polypeptide chain (with an amino acid sequence that may be as set forth in SEQ ID NO. 21), thereby forming a protein heterodimer hIL12b-F8$V_H$-F8$V_L$-hIL2-hIL12a-hGMCSF.

For example, in the protein molecule, the C-terminal of the hIL12b may be fused to the N-terminal of the F8$V_H$, and the C-terminal of the F8$V_H$ may be fused to the N-terminal of the F8$V_L$, to form a second polypeptide chain (with an amino acid sequence that may be as set forth in SEQ ID NO. 15); and the C-terminal of the F8$V_H$ may be fused to the N-terminal of the F8$V_L$, the C-terminal of the F8$V_L$ may be fused to the N-terminal of the hIL12a, the C-terminal of the hIL12a may be fused to the N-terminal of the hIL2, and the C-terminal of the hIL2 may be fused to the N-terminal of the hGMCSF to form a first polypeptide chain (with an amino acid sequence that may be as set forth in SEQ ID NO. 22), thereby forming a protein heterodimer hIL12b-F8$V_H$-F8$V_L$-F8$V_H$-F8$V_L$-hIL12a-hIL2-hGMCSF.

For example, in the protein molecule, the C-terminal of the hIL12b may be fused to the N-terminal of the NHS76$V_H$, and the C-terminal of the NHS76$V_H$ may be fused to the N-terminal of the NHS76$V_L$ to form a second polypeptide chain (with an amino acid sequence that may be as set forth in SEQ ID NO. 16); and the C-terminal of the NHS76$V_H$ may be fused to the N-terminal of the NHS76$V_L$, the C-terminal of the NHS76$V_L$ may be fused to the N-terminal of the hIL12a, the C-terminal of the hIL12a may be fused to the N-terminal of the hIL2, and the C-terminal of the hIL2 may be fused to the N-terminal of the hGMCSF to form a first polypeptide chain (with an amino acid sequence that may be as set forth in SEQ ID NO. 23), thereby forming a protein heterodimer hIL12b-NHS76$V_H$-NHS76$V_L$-NHS76$V_H$-NHS76$V_L$-hIL12a-hIL2-hGMCSF.

In the present application, the mIL12b-L19$V_H$-L19$V_L$-mIL2-mIL12a-mGMCSF, mIL12b-F8$V_H$-F8$V_L$-mIL2-mIL12a-mGMCSF, mIL12b-NHS76$V_H$-NHS76$V_L$-mIL2-mIL12a-mGMCSF, mIL12b-L19$V_H$-L19$V_L$-L19$V_H$-L19$V_L$-mIL12a-mIL2-mGMCSF, mIL12b-F8$V_H$-F8$V_L$-F8$V_H$-F8$V_L$-mIL12a-mIL2-mGMCSF, mIL12b-NHS76$V_H$-NHS76$V_L$-NHS76$V_H$-NHS76$V_L$-mIL12a-mIL2-mGMCSF, hIL12b-F8$V_H$-F8$V_L$-hIL2-hIL12a-hGMCSF, hIL12b-F8$V_H$-F8$V_L$-F8$V_H$-F8$V_L$-hIL12a-hIL2-hGMCSF and hIL12b-NHS76$V_H$-NHS76$V_L$-NHS76$V_H$-NHS76$V_L$-hIL12a-hIL2-hGMCSF may be sequentially referred to as mIL12bscL19-IL2IL12aGMCSF, mIL12bscF8-IL2IL12aGMCSF, mIL12bscNHS76-IL2IL12aGMCSF, mIL12bscL19-scL19IL12aIL2GMCSF, mIL12bscF8-F8IL12aIL2GMCSF, mIL12bscNHS76-scNHS76IL12aIL2GMCSF, hIL12bscF8-IL2IL12aGMCSF, hIL12bscF8-F8IL12aIL2GMCSF and hIL12bscNHS76-scNHS76IL12aIL2GMCSF for short, respectively.

The protein, polypeptide, and/or amino acid sequence involved in the present application should also be understood to include at least the following range: a variant or homologue that has the same or similar functions as said protein or polypeptide.

In the present application, the variant may be a protein or polypeptide formed by substituting, deleting or adding one or more amino acids in an amino acid sequence of said protein and/or polypeptide (for example, the protein molecule). For example, the functional variant may include a protein or polypeptide with amino acid changes induced by substituting, deleting, and/or inserting at least one amino acid, for example, 1-30, 1-20, or 1-10 amino acids, and for another example, 1, 2, 3, 4, or 5 amino acids. The functional variant may substantially maintain the biological properties of said protein or polypeptide before the changes (for example, substitution, deletion, or addition). For example, the functional variant may maintain at least 60%, 70%, 80%, 90%, or 100% of the biological activities of said protein or polypeptide before the changes.

In the present application, the homologue may be a protein or polypeptide that has at least about 80% (for example, at least about 85%, about 90%, about 91%, about 92%, about 93%, about 94%, about 95%, about 96%, about 97%, about 98%, about 99% or higher) sequence homology with the amino acid sequence of said protein and/or polypeptide (for example, the protein molecule).

In the present application, the homology generally refers to the similarity, resemblance or association between two or more sequences. The "percentage of sequence homology" may be calculated in the following way: comparing two sequences to be aligned in a comparison window, determining in the two sequences the number of positions at which identical nucleic acid bases (for example, A, T, C, G) or identical amino acid residues (for example, Ala, Pro, Ser, Thr, Gly, Val, Leu, Ile, Phe, Tyr, Trp, Lys, Arg, His, Asp, Glu, Asn, Gln, Cys, and Met) exist to acquire the number of matching positions; and dividing the number of matching positions by the total number of positions in the comparison window (i.e., the window size), and multiplying a result by 100 to produce the sequence homology percentage. The alignment for determining the sequence homology percentage may be achieved in a variety of ways known in the art, for example, by using publicly available computer software such as BLAST, BLAST-2, ALIGN or Megalign (DNASTAR) software. Those skilled in the art may determine appropriate parameters for sequence alignment, including any algorithm required to implement the maximum alignment undergoing comparison, within a full-length sequence range or within a target sequence region. The homology may also be determined by the following methods: FASTA and BLAST. For the description of the FASTA algorithm, a reference may be made to W. R. Pearson and D. J. Lipman, "Improved Tools for Biological Sequence Comparison", Proc. Natl. Acad. Sci.), 85: 2444-2448, 1988; and D. J. Lipman and W. R. Pearson, "Rapid and Sensitive Protein Similarity Searches", Science, 227: 1435-1441, 1989. For the description of the BLAST algorithm, a reference may be made to S. Altschul, W. Gish, W. Miller, E. W. Myers and D. Lipman, "Basic Local Alignment Search Tool", J. Mol. Biol., 215: 403-410, 1990.

In another aspect, the present application provides a nucleic acid molecule encoding the defined protein molecule.

In the present application, the nucleic acid molecule may be selected from any one of nucleotide sequences as set forth in the group consisting of: SEQ ID NOs. 24-32.

In another aspect, the present application provides a vector including the defined nucleic acid molecule.

In the present application, methods for constructing vectors and plasmids, such as methods for inserting genes encoding proteins into vectors and plasmids or methods for introducing plasmids into host cells, are well known to those ordinarily skilled in the art and have been described in many publications, including Sambrook, J., Fritsch, E. F. and Maniais, T. (1989) Molecular Cloning: A Laboratory Manual, 2nd edition, Cold spring Harbor Laboratory Press.

In another aspect, the present application provides a cell expressing said protein molecule, or containing said nucleic acid molecule, or containing said vector.

In the present application, the cell may be used to treat a tumor. In the present application, the tumor may include a solid tumor. For example, the tumor may include melanoma.

In another aspect, the present application provides a method for preparing said protein molecule, including the following step: culturing said cell.

In the present application, the method may be performed in a situation that the protein molecule may be expressed.

In another aspect, the present application provides a pharmaceutical composition including said protein molecule.

In the present application, the pharmaceutical composition may also include a pharmaceutically acceptable carrier. For example, the pharmaceutically acceptable carrier may include a buffer, an antioxidant, a preservative, a low molecular weight polypeptide, a protein, a hydrophilic polymer, an amino acid, a sugar, a chelating agent, a counterion, a metal complex and/or a non-ionic surfactant, etc. For example, the pharmaceutically acceptable carrier may include an excipient. For example, the excipient may be selected from the group consisting of: starch, dextrin, sucrose, lactose, magnesium stearate, calcium sulfate, carboxymethyl, talcum powder, calcium alginate gel, chitosan and nano microspheres, etc. For example, the pharmaceutically acceptable carrier may also be selected from the group consisting of: a pH regulator, an osmotic pressure regulator, a solubilizer and an bacteriostatic agent.

In the present application, the pharmaceutical composition may be formulated for oral administration, intravenous administration, intramuscular administration, in situ administration at a tumor site, inhalation, rectal administration, vaginal administration, transdermal administration, or administration via a subcutaneous depot.

In the present application, the pharmaceutical composition may be used to inhibit tumor growth. For example, the pharmaceutical composition of the present application may inhibit or delay the development or progression of a disease, may reduce the size of a tumor (or even substantially eliminate the tumor) by promoting the expression of cytokines, and/or may alleviate and/or stabilize a disease state.

In the present application, the pharmaceutical composition may include a therapeutically effective amount of the protein molecule, the nucleic acid molecule, the vector and/or the host cell. therapeutically effective amount is a dose required to prevent and/or treat (at least partially treat) a disorder or condition (such as cancer) and/or any complications thereof in a subject suffering from or at risk of developing the disorder or condition.

In another aspect, the present application provides uses of the protein molecule, the pharmaceutical composition, the nucleic acid molecule, the carrier and/or the cell in the preparation of an anti-tumor drug.

The present application provides the protein molecule, the pharmaceutical composition, the nucleic acid molecule, the vector and/or the cell for treating tumors.

The present application provides a method for alleviating or treating a tumor, which may include administering the protein molecule, the pharmaceutical composition, the nucleic acid molecule, the vector and/or the cell to a subject in need thereof.

In the present application, methods for administration may include oral administration, intravenous administration, intramuscular administration, in situ administration at a tumor site, inhalation, rectal administration, vaginal administration, transdermal administration or administration via a subcutaneous depot.

In the present application, the tumor may include a solid tumor. For example, the tumor may include melanoma.

The present application further comprises the following embodiments.

1. A protein heterodimer, comprising a first polypeptide chain and a second polypeptide chain different from the first polypeptide chain, wherein the first polypeptide chain comprises IL12a, and the second polypeptide chain comprises IL12b;
   - the protein heterodimer further comprises IL2 or a functional fragment thereof, GMCSF or a functional fragment thereof, and one or more targeting moieties; and
   - the IL2 or the functional fragment thereof is located in the first polypeptide chain or in the second polypeptide chain, the GMCSF or the functional fragment thereof is located in the first polypeptide chain or in the second polypeptide chain, and the one or more targeting moieties are each independently located in the first polypeptide chain or in the second polypeptide chain.
2. The protein heterodimer according to Embodiment 1, wherein the first polypeptide chain and the second polypeptide chain form the heterodimer through an interaction between the IL12a and the IL12b.
3. The protein heterodimer according to any one of Embodiments 1-2, wherein the first polypeptide chain further comprises the IL2 or the functional fragment thereof, and the IL2 or the functional fragment thereof is directly or indirectly linked to the IL12a.
4. The protein heterodimer according to any one of Embodiments 1-3, wherein in the first polypeptide chain, the C-terminal of the IL2 or of the functional fragment thereof is directly or indirectly linked to the N-terminal of the IL12a or of the functional fragment thereof.
5. The protein heterodimer according to any one of Embodiments 1-3, wherein in the first polypeptide chain, the N-terminal of the IL2 or of the functional fragment thereof is directly or indirectly linked to the C-terminal of the IL12a or of the functional fragment thereof.
6. The protein heterodimer according to any one of Embodiments 1-5, wherein the first polypeptide chain further comprises the GMCSF or the functional fragment thereof.
7. The protein heterodimer according to any one of Embodiments 1-6, wherein in the first polypeptide chain, the GMCSF or the functional fragment thereof is directly or indirectly linked to the IL12a or the functional fragment thereof.
8. The protein heterodimer according to Embodiment 7, wherein in the first polypeptide chain, the N-terminal of the GMCSF or of the functional fragment thereof is directly or indirectly linked to the C-terminal of the IL12a or of the functional fragment thereof.
9. The protein heterodimer according to any one of Embodiments 1-6, wherein in the first polypeptide chain, the GMCSF or the functional fragment thereof is directly or indirectly linked to the IL2 or the functional fragment thereof.
10. The protein heterodimer according to Embodiment 9, wherein in the first polypeptide chain, the N-terminal of the GMCSF or of the functional fragment thereof is directly or indirectly linked to the C-terminal of the IL2 or of the functional fragment thereof.
11. The protein heterodimer according to any one of Embodiments 1-10, wherein the IL2 or the functional fragment thereof, the IL12a or the functional fragment thereof, and the GMCSF or the functional fragment thereof are sequentially comprised in the first polypeptide chain from the N-terminal to the C-terminal.
12. The protein heterodimer according to any one of Embodiments 1-11, wherein the first polypeptide chain further comprises at least one of the targeting moieties.
13. The protein heterodimer according to any Embodiment 12, wherein in the first polypeptide chain, the at least one targeting moiety is directly or indirectly linked to the IL12a or the functional fragment thereof.
14. The protein heterodimer according to any one of Embodiments 12-13, wherein the C-terminal of the at least one targeting moiety is directly or indirectly linked to the N-terminal of the IL2 or of the functional fragment thereof.

15. The protein heterodimer according to any one of Embodiments 12-14, wherein the one or more targeting moieties, the IL12a or the functional fragment thereof, the IL2 or the functional fragment thereof, and the GMCSF or the functional fragment thereof are sequentially comprised in the first polypeptide chain from the N-terminal to the C-terminal.
16. The protein heterodimer according to any one of Embodiments 1-15, wherein the second polypeptide chain further comprises at least one of the one or more targeting moieties, and the at least one targeting moiety is directly or indirectly linked to the IL12b.
17. The protein heterodimer according to any one of Embodiment 16, wherein the N-terminal of the at least one targeting moiety is directly or indirectly linked to the C-terminal of the IL12b or of the functional fragment thereof.
18. The protein heterodimer according to any one of Embodiments 1-17, wherein the IL2 or the functional fragment thereof, the IL12a or the functional fragment thereof, and the GMCSF or the functional fragment thereof are sequentially comprised in the first polypeptide chain from the N-terminal to the C-terminal, and the IL12b or the functional fragment thereof and the one or more targeting moieties are sequentially comprised in the second polypeptide chain from the N-terminal to the C-terminal, or,
19. The protein heterodimer according to any one of Embodiments 1-17, wherein the IL2 or the functional fragment thereof, the IL12a or the functional fragment thereof, and the GMCSF or the functional fragment thereof are sequentially comprised in the first polypeptide chain from the N-terminal to the C-terminal, and the IL12b or the functional fragment thereof and the one or more targeting moieties are sequentially comprised in the second polypeptide chain from the N-terminal to the C-terminal.
20. The protein heterodimer according to any one of Embodiments 1-19, wherein the IL12a or the functional fragment thereof, the IL12b or the functional fragment thereof, the IL2 or the functional fragment thereof, and the GMCSF or the functional fragment thereof are derived from mammal.
21. The protein heterodimer according to any one of Embodiments 1-20, wherein the IL12a or the functional fragment thereof, the IL12b or the functional fragment thereof, the IL2 or the functional fragment thereof, and the GMCSF or the functional fragment thereof are derived from the same species.
22. The protein heterodimer according to Embodiment 21, wherein the same species is human.
23. The protein heterodimer according to any one of Embodiments 1-22 wherein the protein heterodimer comprises a plurality of targeting moieties, which are the same.
24. The protein heterodimer according to any one of Embodiments 1-22, wherein the protein heterodimer comprises a plurality of targeting moieties, at least two of which are different from each other.
25. The protein heterodimer according to any one of Embodiments 1-24, wherein the one or more targeting moieties are capable of specifically targeting a tumor-associated antigen.
26. The protein heterodimer according to Embodiment 25, wherein the tumor-associated antigen is selected from the group consisting of an EDB domain of fibronectin, an EDA domain of fibronectin, and/or a necrotic region.
27. The protein heterodimer according to any one of Embodiments 1-26, wherein the one or more targeting moieties comprise an antibody or an antigen-binding fragment thereof.
28. The protein heterodimer according to Embodiment 27, wherein the antigen-binding fragment is selected from the group consisting of. Fab, Fab', F(ab')2, F(ab)2, dAb, an isolated complementarity determining region CDR, Fv and scFv.
29. The protein heterodimer according to any one of Embodiments 1-28, wherein the one or more targeting moieties are scFV
30. The protein heterodimer according to any one of Embodiments 1-29, wherein the one or more targeting moieties comprise an amino acid sequence as set forth in any one in the group consisting of: SEQ ID NOs: 1-3.
31. The protein heterodimer according to any one of Embodiments 3-30, wherein the indirect linking comprises linking via a linker.
32. The protein heterodimer according to Embodiment 31, wherein the linker is a peptide linker.
33. The protein heterodimer according to any one of Embodiments 31-32, wherein the one or more targeting moieties are linked to the IL12a and/or the IL12b via the linker.
34. The protein heterodimer according to Embodiment 33, wherein the linker comprises a thrombin cleavage site.
35. The protein heterodimer according to any one of Embodiments 31-34, wherein the linker comprises an amino acid sequence as set forth in any one in the group consisting of: SEQ ID NOs: 33-35.
36. The protein heterodimer according to any one of Embodiments 1-35, wherein the first polypeptide chain comprises an amino acid sequence as set forth in any one in the group consisting of: SEQ ID NOs: 17-23.
37. The protein heterodimer according to any one of Embodiments 1-36, wherein the second polypeptide chain comprises an amino acid sequence as set forth in any one in the group consisting of: SEQ ID NOs: 12-16.
38. The protein heterodimer according to any one of Embodiments 1-37, wherein
   a) the first polypeptide chain comprises an amino acid sequence as set forth in SEQ ID NO: 17 and the second polypeptide chain comprises an amino acid sequence as set forth in SEQ ID NO: 12; and
   b) the first polypeptide chain comprises an amino acid sequence as set forth in SEQ ID NO: 17 and the second polypeptide chain comprises an amino acid sequence as set forth in SEQ ID NO: 13; and
   c) the first polypeptide chain comprises an amino acid sequence as set forth in SEQ ID NO: 17 and the second polypeptide chain comprises an amino acid sequence as set forth in SEQ ID NO: 14; and
   d) the first polypeptide chain comprises an amino acid sequence as set forth in SEQ ID NO: 18 and the second polypeptide chain comprises an amino acid sequence as set forth in SEQ ID NO: 12; and
   e) the first polypeptide chain comprises an amino acid sequence as set forth in SEQ ID NO: 19 and the second polypeptide chain comprises an amino acid sequence as set forth in SEQ ID NO: 13; and
   f) the first polypeptide chain comprises an amino acid sequence as set forth in SEQ ID NO: 20 and the second polypeptide chain comprises an amino acid sequence as set forth in SEQ ID NO: 14; and g) the first polypeptide chain comprises an amino acid sequence as set forth in SEQ ID NO: 21 and the second polypeptide chain comprises an amino acid sequence as set forth in SEQ ID NO: 15; and h) the first polypeptide chain comprises an amino acid sequence as set forth in SEQ ID NO: 22 and the second polypeptide chain comprises an amino acid sequence as set forth in SEQ ID NO: 15; and i) the first polypeptide chain comprises an amino acid sequence as set forth in SEQ ID NO: 23 and the second polypeptide chain comprises an amino acid sequence as set forth in SEQ ID NO: 16.

39. A nucleic acid molecule or nucleic acid molecules encoding the protein heterodimer according to any one of Embodiments 1-38.

40. The nucleic acid molecule according to Embodiment 39, comprising an amino acid sequence as set forth in any one in the group consisting of: SEQ ID NOs: 24-32.

41. A vector, comprising the nucleotide molecule according to any one of Embodiments 39-40.

42. A cell expressing the protein heterodimer according to any one of nucleic acid molecules 1-38, or comprising the nucleic acid molecule or nucleic acid molecules according to Embodiments 39-40, or the vector according to Embodiment 41.

43. A method for preparing the protein heterodimer according to any one of Embodiments 1-38, comprising the following step: culturing the cell according to Embodiment 42.

44. A pharmaceutical composition, comprising the protein heterodimer according to any one of Embodiments 1-38.

45. Use of the heterodimer according to any one of Embodiments 1-38 and/or the pharmaceutical composition according to Embodiment 44 in the preparation of a drug for preventing, alleviating or treating a tumor.

46. The use according to Embodiment 45, wherein the tumor comprises a solid tumor.

47. The use according to any one of Embodiments 45-46, wherein the tumor comprises melanoma.

Not wishing to be bound by any particular theory, the following examples are merely to illustrate the fusion protein, preparation methods and uses etc. according to the present application, and are not intended to limit the scope of the present invention.

EXAMPLES

Example 1 Preparation of Tumor Cells Expressing Regulatable Proteins 1.1 Construction of First Expression Vector pLentis-CMV-rtTA-IRES-Bsd A DNA sequence or rtTA (GenBank: ALK44378.1) with sites BamHI and EcoRI at both ends were synthesized, and a synthesized product was linked to a pUC57 vector. The pUC57 vector linked to the rtTA was enzyme-digested, with an enzyme digestion system as follows: 6 μg of pUC57 vector plasmid linked to the rtTA, 4 μl of enzyme-digestion buffer, 1 μl of BamHI, and 1 μl of EcoRI were added with water to a total volume of 40 μl, and let stand at 37° C. for 12 hours. An EP tube was taken out and added with 4.4 μl of 10× loading buffer; electrophoresis was performed by using 1% agarose gel; and after the electrophoresis, a rtTA fragment was recovered for later use.

In the EP tube, enzyme digestion was performed on the pLentis-CMV-IRES-Bsd vector, with an enzyme digestion system as follows: 2 μg of pLentis-CMV-IRES-Bsd vector plasmid, 3 μl of enzyme digestion buffer, 1 μl of BamHI and 1 μl of XhoI were added with water to a total volume of 30 μl, and let stand at 37° C. for 12 hours. The EP tube was taken out and added with 3.3 μl of 10× loading buffer; electrophoresis was performed by using 1% agarose gel; and after the electrophoresis, a PTRE-MCS-PGK-PURO vector fragment was recovered for later use.

The pLentis-CMV-IRES-Bsd was linked to the rtTA, with a system as follows: 2 μl of pLentis-CMV-IRES-Bsd, 2 μl of rtTA, 1 μl of ligase buffer, 0.5 μl of T4DNA ligase, and 4.5 μl of water were held at room temperature for linking for 4 hours. Then, the linking system was subjected to competent *Escherichia coli* transformation. On the second day, colonies were picked from the transformed plate, placed in an LB medium, and cultured overnight in a shaker at 37° C. Plasmids were extracted from cultured bacteria by using a plasmid extraction kit. Whether the rtTA fragments were successfully linked into the pLentis-CMV-IRES-Bsd vector was identified by enzyme digestion. Then, the correct vector was sent for sequencing to determine that the first expression vector pLentis-CMV-rtTA-IRES-Bsd was successfully constructed.

1.2 Preparation of Virus of First Expression Vector pLentis-CMV-rtTA-IRES-Bsd

1) The cultured 293FT cells were digested, counted and then plated into a 10 cm culture dish at $3\times10^6$ cells/well, where the volume of culture solution was 10 ml.

2) In the evening of the second day, cellular states were observed, and transfection was performed if the cellular states were in a good condition. Chloroquine was added to the culture plate to a final concentration of 25 μM. A test tube was taken and added with sterile water and the following plasmids (5 μg of pMD2.G+15 μg of pSPAX2+20 μg of pLentis-CMV-rtTA-IRES-Bsd), until the total volume reached 1045 μl. Then 155 μl of 2MCaCl2 was added and mixed well. Finally, 1200 μl of 2×HBS was added by dripping over shaking. After the dripping was completed, a resulting mixture was quickly added to cell culture wells and gently shaken and mixed well.

3) In the morning of the third day, cellular states were observed, and the medium was changed to 10 ml of fresh DMEM medium.

4) In the morning of the fifth day, cellular states were observed. Supernatant in the culture dish was collected and filtered with a 0.45 μm filter, then placed in a high-speed centrifuge tube, and centrifuged at 50,000 g for 2 hours. The supernatant was carefully discarded, and the liquid was sucked to dryness with absorbent paper as much as possible. Then, 500 μl of HBSS was used for resuspension and precipitation. Precipitates were dissolved for 2 hours, then dispensed into small tubes, and stored at −70° C. to obtain the virus of the first expression vector pLentis-CMV-rtTA-IRES-Bsd.

1.3 Infection of B16 Tumor Cells Using the Virus of the First Expression Vector pLentis-CMV-rtTA-IRES-Bsd The cultured mouse melanoma cells B16 were digested, inoculated into a 6-well plate at $10^5$ cells/well, with a culture volume of 1 ml. After 24 hours, 10 μl of the virus of the first expression vector pLentis-CMV-rtTA-IRES-Bsd was added. After the resulting mixture was incubated in an incubator for 24 hours, supernatant was discarded and replaced with fresh medium to continue culturing. After the cells grew all over, the cells were transferred to a culture flask. Blasticidin was added at a concentration suitable for these cells to continue culturing. The medium was changed every two days, and the concentration of the blasticidin was kept at 8 μg/ml. After one week of screening, the survived cells were cells that stably expressed the regulator protein, and these cells were named as B16 (rtTA).

Example 2 Effect of Induced Expression of Green Fluorescent Protein (GFP) on Tumor Growth 2.1 Construction of Regulatable Expression Vector Encoding Green Fluorescent Protein (GFP)

A PCR reaction was conducted with a GFP gene as a template by using primers to amplify GFP genes, where PCR conditions were as listed in the instructions of the PrimeStarHS DNA polymerase. After agarose gel electrophoresis was performed for the PCR, the gel was extracted with a gel extraction kit. Then, enzyme digestion was performed by using BamHI and EcoRI, with an enzyme digestion system as follows: 30 μg of PCR product, 4 μl of digestion buffer, 1 μl of BamHI and 1 μl of EcoRI were added with water until the total volume reached 40 μl, and then let stand at 37° C. for 12 hours. An EP tube was taken out and added with 4.4 μl of 10× loading buffer; electrophoresis was performed by using 1% agarose gel; and after the electrophoresis, a GFP gene fragment was recovered for later use.

Enzyme digestion was performed on a regulatable expression vector, with a system as follows: 2 μg of pLentis-PTRE-MCS-PGK-PURO plasmid, 3 μl of enzyme digestion buffer, 1 μl of BamHI and 1 μl of EcoRI were added with water to a total volume of 30 μl, and let stand at 37° C. for 12 hours. An EP tube was taken out and added with 3.3 μl of 10× loading buffer; electrophoresis was performed by using 1% agarose gel; and after the electrophoresis, a fragment was recovered for later use. The pLentis-PTRE-MCS-PGK-PURO was linked to the GFP, with a linking system including: 2 μl of pLentis-PTRE-MCS-PGK-PURO, 2 μl of GFP, 1 μl of ligase buffer, 0.5 μl of T4DNA ligase, and 4.5 μl of water. The mixture was left at room temperature for linkage for 4 hours. Then, the linking system was subjected to competent *Escherichia coli* transformation. On the second day, colonies were picked from the transformed plate, placed in an LB medium, and cultured overnight in a shaker at 37° C. Plasmids were extracted from cultured bacteria by using a plasmid extraction kit. Whether the fragment was successfully linked into the vector was identified by enzyme digestion. Then, the correct vector was sent for sequencing to determine that the second expression vector pLentis-CMV-rtTA-IRES-Bsd was successfully constructed.

2.2 Preparation of Cells Regulating and Expressing GFP

A virus of a GFP-expressing vector was prepared with a method the same as that for preparing the virus of the first expression vector, to obtain a virus of a second expression vector pLentis-PTRE-GFP-PGK-PURO.

The cultured tumor cells B16 (rtTA) were digested, inoculated into a 6-well plate at $10^5$ cells/well, with a culture volume of 1 ml. After 24 hours, 10 μl of the virus of the second regulatable expression vector pLentis-PTRE-GFP-PGK-PURO was added. After the resulting mixture was continuously incubated in an incubator for 24 hours, supernatant was discarded and replaced with fresh medium to continue culturing. After the cells grew all over, the cells were transferred to a culture flask. Puromycin was added at a final concentration of 3 μg/ml. After the culturing was continued for three days, the survived cells were cells capable of regulating and expressing GFP, which were named as B16 (rtTA)-GFP.

2.3 Effect of Regulated Expression of GFP on Tumor Growth

Figure 2:
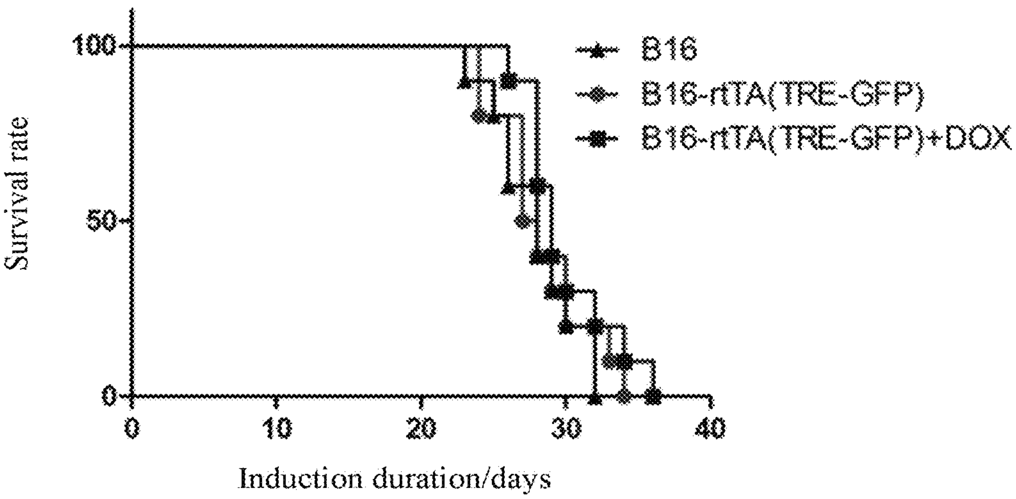
FIG. 2 shows the survival rate of mice in each group.

The cells B16(rtTA)-GFP in a logarithmic growth phase were digested, diluted with HBSS to $2\times10^6$ cells/ml, and injected into the right backs of a total of 10 C57BL/6 female mice being 8-10 weeks old at 50 μl/mouse by using a 1 ml syringe. After tumors grew, the mice were fed with water containing 2 g/L doxycycline, and the tumor growth in the mice was recorded, as shown in FIG. 1. The results showed that the induced expression of GFP had no inhibitory effect on tumor growth (in FIG. 1, each broken line represented the tumor area in one mouse). The survival curve of each group of mice was shown in FIG. 2.

Example 3 Design of Protein Heterodimer

The following protein heterodimers were designed: mIL12bscL19-IL2IL12aGMCSF, mIL12bscF8-IL2IL12aGMCSF, mIL12bscNHS76-IL2IL12aGMCSF, mIL12bscL19-scL19IL12aIL2GMCSF, mIL12bscF8-scF8IL12aIL2GMCSF, mIL12bscNHS76-scNHS76IL12aIL2GMCSF, hIL12bscF8-IL2IL12aGMCSF, hIL12bscF8-scF8IL12aIL2GMCSF, hIL12bscNHS76-scNHS76IL12aIL2GMCSF. The structures of the protein heterodimers above were shown in the figures (FIG. 3 to FIG. 11).

For example, FIG. 3 shows the structure of a protein heterodimer mIL12bscL19-IL2IL12aGMCSF, where “m” in the formula represents that the cytokines are derived from mice. The protein heterodimer includes a first polypeptide chain and a second polypeptide chain different from the first polypeptide chain. In the second polypeptide chain, mIL12bscL19 represents the sequential inclusion of interleukin IL12b and the targeting moieties $L19V_H$ and $L19V_L$ from the N-terminal to the C-terminal, and the targeting moieties $L19V_H$ and $L19V_L$ located at the C-terminal of the second polypeptide chain may be represented by scL19. In the first polypeptide chain, IL2IL12aGMCSF represents the sequential inclusion of interleukin IL2, interleukin IL12a and granulocyte macrophage colony stimulating factor (GMCSF) from the N-terminal to the C-terminal.

For example, FIG. 4 shows the structure of a protein heterodimer mIL12bscF8-IL2IL12aGMCSF, where “m” in the formula represents that the cytokines are derived from mice. The protein heterodimer includes a first polypeptide chain and a second polypeptide chain different from the first polypeptide chain. In the second polypeptide chain, mIL12bscF8 represents the sequential inclusion of interleukin IL12b and the targeting moieties $F8V_H$ and $F8V_L$ from the N-terminal to the C-terminal, and the targeting moieties $F8V_H$ and $F8V_L$ located at the C-terminal of the second polypeptide chain may be represented by scF8. In the first polypeptide chain, IL2IL12aGMCSF represents the sequential inclusion of interleukin IL2, interleukin IL12a and granulocyte macrophage colony stimulating factor (GMCSF) from the N-terminal to the C-terminal.

For example, FIG. 5 shows the structure of a protein heterodimer mIL12bscNHS76-IL2IL12aGMCSF, where “m” in the formula represents that the cytokines are derived from mice. The protein heterodimer includes a first polypeptide chain and a second polypeptide chain different from the first polypeptide chain. In the second polypeptide chain, mIL12bscNHS76 represents the sequential inclusion of interleukin IL12b and the targeting moieties $NHS76V_H$ and $NHS76V_L$ from the N-terminal to the C-terminal, and the targeting moieties $NHS76V_H$ and $NHS76V_L$ located at the C-terminal of the second polypeptide chain may be represented by scNHS76. In the first polypeptide chain, IL2IL12aGMCSF represents the sequential inclusion of interleukin IL2, interleukin IL12a and granulocyte macrophage colony stimulating factor (GMCSF) from the N-terminal to the C-terminal.

For example, FIG. 6 shows the structure of a protein heterodimer mIL12bscL19-scL19IL12aIL2GMCSF, where "m" in the formula represents that the cytokines are derived from mice. The protein heterodimer includes a first polypeptide chain and a second polypeptide chain different from the first polypeptide chain. In the second polypeptide chain, mIL12bscL19 represents the sequential inclusion of interleukin IL12b and the targeting moieties $L19V_H$ and $L19V_L$ from the N-terminal to the C-terminal, and the targeting moieties $L19V_H$ and $L19V_L$ located at the C-terminal of the second polypeptide chain may be represented by bscL19. In the first polypeptide chain, scL19IL12aIL2GMCSF represents the sequential inclusion of the targeting moieties $L19V_H$ and $L19V_L$, interleukin IL12a, interleukin IL2 and the granulocyte macrophage colony stimulating factor (GMCSF) from the N-terminal to the C-terminal, where the targeting moieties $L19V_H$ and $L19V_L$ located at the N-terminal of the first polypeptide chain may be represented by scL19. For example, FIG. 9 shows the structure of a protein heterodimer hIL12bscF8-IL2IL12aGMCSF, where "h" in the formula represents that the cytokines are derived from humans. The protein heterodimer includes a first polypeptide chain and a second polypeptide chain different from the first polypeptide chain. In the second polypeptide chain, hIL12bscF8 represents the sequential inclusion of interleukin IL12b and the targeting moieties $F8V_H$ and $F8V_L$ from the N-terminal to the C-terminal, and the targeting moieties $F8V_H$ and $F8V_L$ located at the C-terminal of the second polypeptide chain may be represented by scF8. In the first polypeptide chain, IL2IL12aGMCSF represents the sequential inclusion of interleukin IL2, interleukin IL12a and granulocyte macrophage colony stimulating factor (GMCSF) from the N-terminal to the C-terminal.

For example, FIG. 10 shows the structure of a protein heterodimer hIL12bscF8-scF8IL12aIL2GMCSF, where "h" in the formula represents that the cytokines are derived from humans. The protein heterodimer includes a first polypeptide chain and a second polypeptide chain different from the first polypeptide chain. In the second polypeptide chain, hIL12bscF8 represents the sequential inclusion of interleukin IL12b and the targeting moieties $F8V_H$ and $F8V_L$ from the N-terminal to the C-terminal, and the targeting moieties $F8V_H$ and $F8V_L$ located at the C-terminal of the second polypeptide chain may be represented by scF8. In the first polypeptide chain, scF8IL12aIL2GMCSF represents the sequential inclusion of the targeting moieties $F8V_H$ and $F8V_L$, interleukin IL12a, interleukin IL2 and the granulocyte macrophage colony stimulating factor (GMCSF) from the N-terminal to the C-terminal, where the targeting moieties $F8V_H$ and $F8V_L$, located at the N-terminal of the first polypeptide chain may be represented by scF8.

Example 4 Effect of Induced Expression of mIL12bscF8-IL2IL12aGMCSF on Tumor Growth 4.1 Construction of Regulatable Expression Vector mIL12bscF8-IL2IL12aGMCSF A gene coding sequence of mIL12bscF8-IL2IL12aGMCSF with BamHI, BglII and XhoI, EcoRI restriction enzyme sites on both ends were synthesized. Then, enzyme digestion was performed by using BamHI or BglII and XhoI or EcoRI, with an enzyme digestion system as follows: 5 μg of mIL12bscF8-IL2IL12aGMCSF plasmid, 4 μl of enzyme digestion buffer, 1 μl of BamHI and 1 μl of XhoI were added with water to a total volume of 40 μl, and let stand at 37° C. for 12 hours. An EP tube was taken out and added with 4.4 μl of 10× loading buffer; electrophoresis was performed by using 1% agarose gel; and after the electrophoresis, an mIL12bscF8-IL2IL12aGMCSF gene fragment was recovered for later use.

The protein heterodimer mIL12bscF8-IL2IL12aGMCSF includes the amino acid sequences as set forth in SEQ ID NO. 13 and SEQ ID NO. 17, and a nucleotide sequence encoding the mIL12bscF8-IL2IL12aGMCSF is as set forth in SEQ ID NO. 25.

Enzyme digestion was performed on a regulatable expression vector pLentis-PTRE-MCS-PGK-PURO, with an enzyme digestion system as follows: 2 μg of pLentis-PTRE-MCS-PGK-PURO vector plasmid, 3 μl of enzyme digestion buffer, 1 μl of BamHI and 1 μl of XhoI were added with water to a total volume of 30 μl, and let stand at 37° C. for 12 hours. The EP tube was taken out and added with 3.3 μl of 10× loading buffer; electrophoresis was performed by using 1% agarose gel; and after the electrophoresis, a pLentis-PTRE-MCS-PGK-PURO vector fragment was recovered for later use.

The pLentis-PTRE-MCS-PGK-PURO was linked to the mIL12bscF8-IL2IL12aGMCSF, with a linking system including: 2 μl of pLentis-PTRE-MCS-PGK-PURO, 2 μl of mIL12bscF8-IL2IL12aGMCSF, 1 μl of ligase buffer, 0.5 μl of T4DNA ligase, and 4.5 μl of water. The mixture was left at room temperature for linkage for 4 hours. Then, the linking system was subjected to competent *Escherichia coli* transformation. On the second day, colonies were picked from the transformed plate, placed in an LB medium, and cultured overnight in a shaker at 37° C. Plasmids were extracted from cultured bacteria by using a plasmid extraction kit. Whether the fragment was successfully linked into the vector was identified by enzyme digestion. Then, the correct vector was sent for sequencing to determine that the second expression vector pLentis-PTRE-mIL12bscF8-IL2IL12aGMCSF-PGK-PURO was successfully constructed.

4.2 Preparation of Cells Capable of Regulating and Expressing mIL12bscF8-IL2IL12aGMCSF A virus of an mIL12bscF8-IL2IL12aGMCSF-expressing vector was prepared with a method the same as that for preparing the virus of the first expression vector, to obtain a virus of a second expression vector pLentis-PTRE-mIL12bscF8-IL2IL12aGMCSF-PGK-PURO.

The cultured tumor cells B16 (rtTA) were digested, inoculated into a 6-well plate at $10^5$ cells/well, with a culture volume of 1 ml. After 24 hours, 10 μl of the virus of the second regulatable expression vector pLentis-PTRE-mIL12bscF8-IL2IL12aGMCSF-PGK-PURO was added. After the resulting mixture was continuously incubated in an incubator for 24 hours, supernatant was discarded and replaced with fresh medium to continue culturing. After the cells grew all over, the cells were transferred to a culture flask. Puromycin was added at a final concentration of 3 μg/ml. After the culturing was continued for three days, the survived cells were cells capable of regulating and expressing mIL12bscF8-IL2IL12aGMCSF, which were named as B16(rtTA)-mIL12bscF8-IL2IL12aGMCSF.

Figure 12:
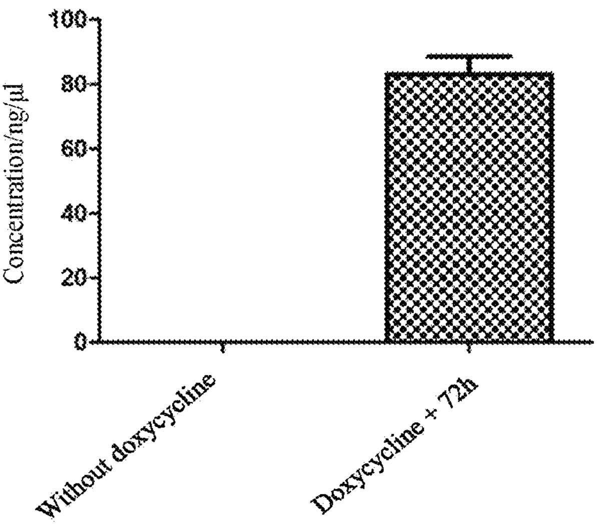
FIG. 12 shows the expression of a protein heterodimer mIL12bscF8-IL2IL12aGMCSF in an in vitro assay.

4.3 In Vitro Assay of the Effect of Induced Expression of mIL12bscF8-IL2IL12aGMCSF B16 (rtTA) mIL12bscF8-IL2IL12aGMCSF cells were plated into a 24-well plate at $5\times10^4$ per well. After 24 hours, 100 ng/ml doxycycline (DOX) was added to the wells. The culture was continued for 72 hours, and the supernatant was collected. The expression quantity of the protein heterodimer in the supernatant was detected by using a mouse IL12p70 ELISA kit, where the operations were conducted according to the instructions of the kit. Wells without DOX induction were used as controls. As shown in FIG. 12, the added DOX induced the expression of the protein heterodimer mIL12bscF8-IL2IL12aGMCSF.

4.4 Effect of Induced Expression of mIL12bscF8-IL2IL12aGMCSF on Tumor Growth.

Figure 13:
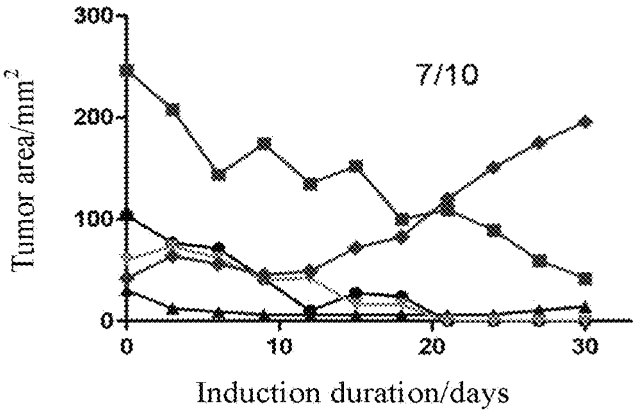
FIG. 13 shows the tumor regression in mice induced by a protein heterodimer mIL12bscF8-IL2IL12aGMCSF.

The cells B16(rtTA)-mIL12bscF8-IL2IL12aGMCSF in a logarithmic growth phase were digested, diluted with HBSS to $2\times10^6$ cells/ml, and injected into the right backs of a total of 10 C57BL/6 female mice being 8-10 weeks old at 50 μl/mouse by using a 1 ml syringe. After tumors grew, the mice were fed with water containing 2 g/L doxycycline, and the tumor growth and tumor clearance rate in the mice were recorded, with the number of tumor-cleared mice/the total number of mice=7/10, as shown in FIG. 13. mIL12bscF8-IL2IL12aGMCSF can induce tumor regression in some mice.

Example 5 Effect of Induced Expression of mIL12bscF8-scF8IL12aIL2GMCSF on Tumor Growth 5.1 Construction of Regulatable Expression Vector mIL12bscF8-scF8IL12aIL2GMCSF A gene coding sequence of mIL12bscF8-scF8IL12aIL2GMCSF with BamHI, BglII and XhoI, EcoRI restriction enzyme sites on both ends were synthesized. Then, enzyme digestion was performed by using BamHI or BglII and XhoI or EcoRl, with an enzyme digestion system as follows: 5 μg of mIL12bscF8-scF8IL12aIL2GMCSF plasmid, 4 μl of enzyme digestion buffer, 1 μl of BamHI and 1 μl of XhoI were added with water to a total volume of 4 μl, and let stand at 37° C. for 12 hours. An EP tube was taken out and added with 4.4 μl of 10× loading buffer; electrophoresis was performed by using 1% agarose gel; and after the electrophoresis, a mIL12bscF8-scF8IL12aIL2GMCSF gene fragment was recovered for later use.

The protein heterodimer mIL12bscF8-scF8IL12aIL2GMCSF includes the amino acid sequences as set forth in SEQ ID NO. 13 and SEQ ID NO. 19, and a nucleotide sequence encoding the mIL12bscF8-scF8IL12aIL2GMCSF is as set forth in SEQ ID NO. 28.

Enzyme digestion was performed on a regulatable expression vector pLentis-PTRE-MCS-PGK-PURO, with an enzyme digestion system as follows: 2 μg of pLentis-PTRE-MCS-PGK-PURO vector plasmid, 3 μl of enzyme digestion buffer, 1 μl of BamHI and 1 μl of XhoI were added with water to a total volume of 30 μl, and let stand at 37° C. for 12 hours. The EP tube was taken out and added with 3.3 μl of 10× loading buffer; electrophoresis was performed by using 1% agarose gel; and after the electrophoresis, a pLentis-PTRE-MCS-PGK-PURO vector fragment was recovered for later use.

The pLentis-PTRE-MCS-PGK-PURO was linked to the mIL12bscF8-scF8IL12aIL2GMCSF, with a linking system including: 2 μl of pLentis-PTRE-MCS-PGK-PURO, 2 μl of mIL12bscF8-scF8IL12aIL2GMCSF, 1 μl of ligase buffer, 0.5 μl of T4DNA ligase, and 4.5 μl of water. The mixture was left at room temperature for linkage for 4 hours. Then, the linking system was subjected to competent *Escherichia coli* transformation. On the second day, colonies were picked from the transformed plate, placed in an LB medium, and cultured overnight in a shaker at 37° C. Plasmids were extracted from cultured bacteria by using a plasmid extraction kit. Whether the fragment was successfully linked into the vector was identified by enzyme digestion. Then, the correct vector was sent for sequencing to determine that the second expression vector pLentis-PTRE-mIL12bscF8-scF8IL12aIL2GMCSF-PGK-PURO was successfully constructed.

5.2 Preparation of Cells Capable of Regulating and Expressing mIL12bscF8-scF8IL12aIL2GMCSF A virus of an mIL12bscF8-scF8IL12aIL2GMCSF-expressing vector was prepared with a method the same as that for preparing the virus of the first expression vector, to obtain a virus of a second expression vector pLentis-PTRE-mIL12bscF8-IL2IL12aGMCSF-PGK-PURO.

The cultured tumor cells B16 (rtTA) were digested, inoculated into a 6-well plate at $10^5$ cells/well, with a culture volume of 1 ml. After 24 hours, 10 μl of the virus of the second regulatable expression vector pLentis-PTRE-mIL12bscF8-scF8IL12aIL2GMCSF-PGK-PURO was added. After the resulting mixture was continuously incubated in an incubator for 24 hours, supernatant was discarded and replaced with fresh medium to continue culturing. After the cells grew all over, the cells were transferred to a culture flask. Puromycin was added at a final concentration of 3 μg/ml. After the culturing was continued for three days, the survived cells were cells capable of regulating and expressing mIL12bscF8-scF8IL12aIL2GMCSF, which were named as B16(rtTA)-mIL12bscF8-scF8IL12aIL2GMCSF.

5.3 Effect of Induced Expression of mIL12bscF8-scF8IL12aIL2GMCSF on Tumor Growth.

Figure 14:
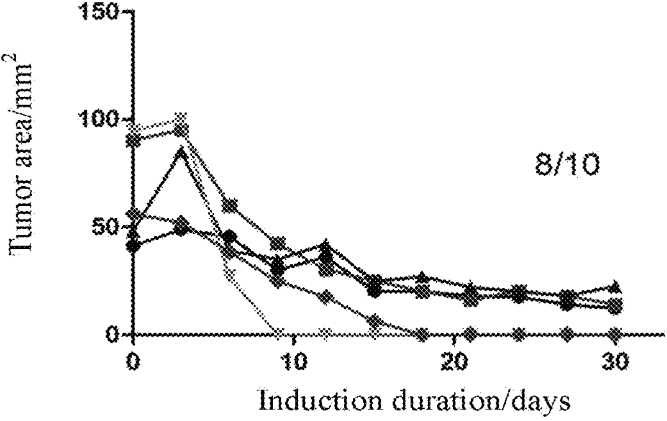
FIG. 14 shows the tumor regression in mice induced by a protein heterodimer mIL12bscF8-scF8IL12aIL2GMCSF.

The cells B16(rtTA)-mIL12bscF8-scF8IL12aIL2GMCSF in a logarithmic growth phase were digested, diluted with HBSS to $2\times10^6$ cells/ml, and injected into the right backs of a total of 10 C57BL/6 female mice being 8-10 weeks old at 50 μl/mouse by using a 1 ml syringe. After tumors grew, the mice were fed with water containing 2 g/L doxycycline, and the tumor growth and tumor clearance rate in the mice were recorded, with the number of tumor-cleared mice/the total number of mice=8/10, as shown in FIG. 14. mIL12bscF8-scF8IL12aIL2GMCSF can induce tumor regression in some mice.

Example 6 Construction of Cells Expressing hIL12bscF8-IL2IL12aGMCSF, hIL12bscF8-scF8IL12aIL2GMCSF, and hIL12bscNHS76-scNHS76IL12aIL2GMCSF 6.1 Construction of Vector Capable of Regulating and Expressing Target Gene In the EP tube, enzyme digestion was performed on the pLentis-CMV-MCS-TRES-PURO vector, with a system as follows: 2 μg of pLentis-CMV-MCS-IRES-PURO vector plasmid, 3 μl of enzyme digestion buffer, 1 μl of BamHI and 1 μl of XhoI were added with water to a total volume of 30 μl, and let stand at 37° C. for 12 hours. The EP tube was taken out and added with 3.3 μl of 10× loading buffer; electrophoresis was performed by using 1% agarose gel; and after the electrophoresis, a pLentis-CMV-MCS-IRES-PURO vector fragment was recovered for later use.

The DNA sequences of hIL12bscF8-IL2IL12aGMCSF, hIL12bscF8-scF8IL12aIL2GMCSF, and hIL12bscNHS76- scNHS76IL12aIL2GMCSF were synthesized respectively, where during the synthesis, the restriction enzyme site BamHI or BglII was added to a 5'-terminal, and the restriction enzyme site XhoI or EcoRI was added to a 3'-terminal. The synthesized plasmid with the target gene was enzyme-digested, with a system as follows: 5 kg of plasmid, 4 μl of enzyme-digestion buffer, 1 μl of BamHI, and 1 μl of XhoI were added with water to a total volume of 40 μl, and let stand at 37° C. for 12 hours. An EP tube was taken out and added with 4.4 μl of 10× loading buffer; electrophoresis was performed by using 1% agarose gel; and after the electrophoresis, a mIL2IL12aIL12bGMCSF gene fragment was recovered for later use.

The protein heterodimer hIL12bscF8-IL2IL12aGMCSF includes the amino acid sequences as set forth in SEQ ID NO. 15 and SEQ ID NO. 21, and a nucleotide sequence encoding the hIL12bscF8-IL2IL12aGMCSF is as set forth in SEQ ID NO. 30.

The protein heterodimer hIL12bscF8-scF8IL12aIL2GMCSF includes the amino acid sequences as set forth in SEQ ID NO. 15 and SEQ ID NO. 22, and a nucleotide sequence encoding the hIL12bscF8-scF8IL12aIL2GMCSF is as set forth in SEQ ID NO. 31.

The protein heterodimer hIL12bscNHS76-scNHS76IL12aIL2GMCSF includes the amino acid sequences as set forth in SEQ ID NO. 16 and SEQ ID NO. 23, and a nucleotide sequence encoding the hIL12bscNHS76-scNHS76IL12aIL2GMCSF is as set forth in SEQ ID NO. 32.

The pLentis-CMV-MCS-TRES-PURO was linked to the hIL12bscF8-IL2IL12aGMCSF, the hIL12bscF8-scF8IL12aIL2GMCSF, and the hIL12bscNHS76-scNHS76IL12aIL2GMCSF respectively, with a linking system including: 2 μl of pLentis-CMV-MCS-IRES-PURO, 2 μl of gene fragment, 1 μl of ligase buffer, 0.5 μl of T4DNA ligase, and 4.5 μl of water. The mixture was left at room temperature for linkage for 4 hours. Then, the linking system was subjected to competent *Escherichia coli* transformation. On the second day, colonies were picked from the transformed plate, placed in an LB medium, and cultured overnight in a shaker at 37° C. Plasmids were extracted from cultured bacteria by using a plasmid extraction kit. Whether the fragments were successfully linked into the vector was identified by enzyme digestion. Then, the correct vectors were sent for sequencing to determine that the construction was successful, thereby obtaining the vector pLentis-CMV-hIL12bscF8-IL2IL12aGMCSF-IRES-PURO, the vector pLentis-CMV-hIL12bscF8-scF8IL12aIL2GMCSF-IRES-PURO, and the vector pLentis-CMV-hIL12bscNHS76-scNHS76IL12aIL2GMCSF-IRES-PURO, which expressed the target gene.

6.2 Preparation of Virus of Expression Vector

1) The cultured 293FT cells were digested, counted and then plated into a 10 cm culture dish at $3\times10^6$ cells/well, where the volume of culture solution was 10 ml, and a total of five plates were spread.
2) In the evening of the second day, cellular states were observed, and transfection was performed if the cellular states were good. Chloroquine was added to the culture plates to a final concentration of 25 μM. A test tube was taken and added with sterile water and the following plasmids (6 μg of pMD2.G+15 μg of pSPAX2+20 kg of expression vector), until the total volume reached 1045 μl. Then 155 μl of 2M $CaCl_2$) was added and mixed well. Finally, 1200 μl of 2×HBS was added by dripping over shaking. After the dripping was completed, a resulting mixture was quickly added to cell culture wells and gently shaken and mixed well.
3) In the morning of the third day, cellular states were observed, and the medium was changed to 10 ml of fresh DMEM medium.
4) In the morning of the fifth day, cellular states were observed. Supernatant in the culture dish was collected and filtered with a 0.45 km filter, then placed in a high-speed centrifuge tube, and centrifuged at 50,000 g for 2 hours. The supernatant was carefully discarded, and the liquid was sucked to dryness with absorbent paper as much as possible. Then, 200 μl of HBSS was used for resuspension and precipitation. Precipitates were dissolved for 2 hours, then dispensed into small tubes, and stored at −70° C.

6.3 Transfection of 293A Cells with Expression Virus

The cultured 293A cells were digested, inoculated into a 6-well plate at $10^5$ cells/well, with a culture volume of 1 ml. After 24 hours, 10 μl of the virus expressing the above target gene was added. After the resulting mixture was continuously incubated in an incubator for 24 hours, supernatant was discarded and replaced with fresh medium to continue culturing. After the cells grew all over, the cells were transferred to a culture flask. Puromycin was added at a final concentration of 3 μg/ml. The culturing was continued by changing the medium every two days, where the concentration of the puromycin was maintained. After one week of screening, the survived cells were cells stably expressing the cytokines, and these cells were named as 293A(hIL12bscF8-IL2IL12aGMCSF), 293A(hIL12bscF8-scF8IL12aIL2GMCSF), and 293A(hIL12bscNHS76-scNHS76IL12aIL2GMCSF), respectively.

Figure 15:
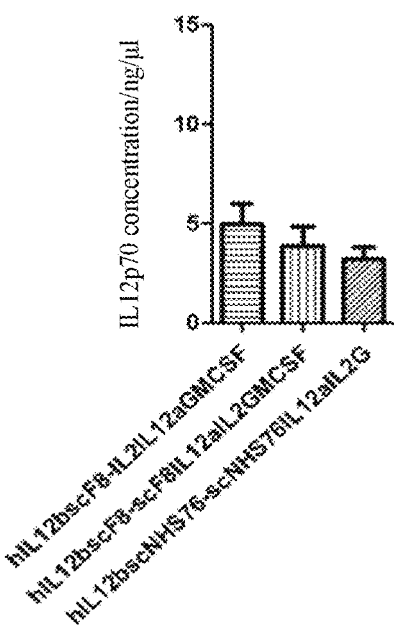
FIG. 15 shows the successful expression of the protein heterodimer of the present application.

The constructed expression cells were plated into a 24-well plate at $5\times10^4$ per well, and cultured for 96 hours. The supernatant was collected. The expression of the protein heterodimer in the supernatant was detected by using a human IL12p70 ELISA kit, where the operations were conducted according to the instructions of the kit. As shown in FIG. 15, these cells are capable of producing a large amount of IL12p70, and the cells expressing the protein heterodimers were successfully constructed.

The foregoing detailed description is provided by way of explanation and examples, and is not intended to limit the scope of the appended claims. Various changes of the embodiments listed in the present application until now are obvious to those of ordinary skill in the art, and should be kept within the scope of the appended claims and equivalents thereof.

The invention claimed is:

1. A protein heterodimer, comprising a first polypeptide chain and a second polypeptide chain different from said first polypeptide chain, wherein said first polypeptide chain comprises interleukin 12(a) (IL12), and said second polypeptide chain comprises interleukin 12b (IL12b);

said protein heterodimer further comprises interleukin-2 (IL2), granulocyte macrophage colony stimulating factor (GMCSF), and one or more targeting moieties; and said IL2 is located in said first polypeptide chain, said GMCSF is located in said first polypeptide chain, and said one or more targeting moieties are each independently located in said first polypeptide chain or in said second polypeptide chain;

wherein said IL2, said IL12a and said GMCSF are sequentially comprised in said first polypeptide chain from the N-terminal to the C-terminal, and said IL12b and one of said one or more targeting moieties are sequentially comprised in said second polypeptide chain from the N-terminal to the C-terminal; or wherein one of said one or more targeting moieties, said IL12a, said IL2 and said GMCSF are sequentially comprised in said first polypeptide chain from the N-terminal to the C-terminal, and said IL12b and one of said one or more targeting moieties are sequentially comprised in said second polypeptide chain from the N-terminal to the C-terminal;

wherein any one of said one or more targeting moieties comprises the amino acid sequence as set forth in any one in the group consisting of: SEQ ID NOs: 1-3.

2. The protein heterodimer of claim 1, wherein a) said first polypeptide chain comprises the amino acid sequence as set forth in SEQ ID NO: 17 and said second polypeptide chain comprises the amino acid sequence as set forth in SEQ ID NO: 12;

b) said first polypeptide chain comprises the amino acid sequence as set forth in SEQ ID NO: 17 and said second polypeptide chain comprises the amino acid sequence as set forth in SEQ ID NO: 13;

c) said first polypeptide chain comprises the amino acid sequence as set forth in SEQ ID NO: 17 and said second polypeptide chain comprises the amino acid sequence as set forth in SEQ ID NO: 14, d) said first polypeptide chain comprises the amino acid sequence as set forth in SEQ ID NO: 18 and said second polypeptide chain comprises the amino acid sequence as set forth in SEQ ID NO: 12:

e) said first polypeptide chain comprises the amino acid sequence as set forth in SEQ ID NO: 19 and said second polypeptide chain comprises the amino acid sequence as set forth in SEQ ID NO: 13;

f) said first polypeptide chain comprises the amino acid sequence as set forth in SEQ ID NO: 20 and said second polypeptide chain comprises the amino acid sequence as set forth in SEQ ID NO: 14;

g) said first polypeptide chain comprises the amino acid sequence as set forth in SEQ ID NO: 21 and said second polypeptide chain comprises the amino acid sequence as set forth in SEQ ID NO: 15;

h) said first polypeptide chain comprises the amino acid sequence as set forth in SEQ ID NO: 22 and said second polypeptide chain comprises the amino acid sequence as set forth in SEQ ID NO: 15; or i) said first polypeptide chain comprises the amino acid sequence as set forth in SEQ ID NO: 23 and said second polypeptide chain comprises the amino acid sequence as set forth in SEQ ID NO: 16.

3. A pharmaceutical composition, comprising the protein heterodimer of claim 1.

* * * * *